US011046932B2

(12) United States Patent
Lienkamp et al.

(10) Patent No.: US 11,046,932 B2
(45) Date of Patent: Jun. 29, 2021

(54) METHOD OF PRODUCING RENAL CELLS FROM DIFFERENTIATED CELLS

(71) Applicant: Albert-Ludwigs-Universitaet Freiburg, Freiburg (DE)

(72) Inventors: Soeren Lienkamp, Freiburg (DE); Michael Kaminski, Freiburg (DE); Sebastian Arnold, Freiburg (DE); Gerd Walz, Freiburg (DE)

(73) Assignee: Albert-Ludwigs-Universitaet Freiburg, Freiburg (DE)

( * ) Notice: Subject to any disclaimer, the term of this patent is extended or adjusted under 35 U.S.C. 154(b) by 324 days.

(21) Appl. No.: 16/072,459

(22) PCT Filed: Jan. 25, 2017

(86) PCT No.: PCT/EP2017/051504
§ 371 (c)(1),
(2) Date: Jul. 24, 2018

(87) PCT Pub. No.: WO2017/129598
PCT Pub. Date: Aug. 3, 2017

(65) Prior Publication Data
US 2019/0071646 A1   Mar. 7, 2019

(30) Foreign Application Priority Data

Jan. 25, 2016 (EP) .................... 16152655
Aug. 23, 2016 (EP) .................... 16185290

(51) Int. Cl.
| *C12N 5/071* | (2010.01) |
| *A01K 67/027* | (2006.01) |
| *C12N 15/62* | (2006.01) |
| *C12N 15/85* | (2006.01) |
| *C12N 5/077* | (2010.01) |
| *A01K 67/00* | (2006.01) |

(52) U.S. Cl.
CPC .......... *C12N 5/0686* (2013.01); *A01K 67/027* (2013.01); *C12N 5/0656* (2013.01); *C12N 15/62* (2013.01); *C12N 15/8509* (2013.01); *A01K 67/00* (2013.01); *C12N 2501/60* (2013.01); *C12N 2506/1307* (2013.01); *C12N 2510/00* (2013.01); *C12N 2513/00* (2013.01); *G01N 2500/10* (2013.01)

(58) Field of Classification Search
None
See application file for complete search history.

(56) References Cited

U.S. PATENT DOCUMENTS

| 2012/0101001 A1* | 4/2012 | Suthanthiran | ........ C12Q 1/6883 506/9 |
| 2015/0284689 A1 | 10/2015 | Nigam | |

FOREIGN PATENT DOCUMENTS

| EP | 2 532 741 A1 | 12/2012 |
| WO | WO 2015/056756 A1 | 4/2015 |

OTHER PUBLICATIONS

Shibazaki, et al. (2008) "Cyst formation and activation of the extracellular regulated kinase pathway after kidney specific inactivation of Pkd1", Human Molecular Genetics, 17(11): 1505-16. (Year: 2008).*
Norman, Jill, "Fibrosis and Progression of Autosomal Dominant Polycystic Kidney Disease (ADPKD)", (Jun. 21, 2011), *Biochemica et Biophysica ACTA*, vol. 1812, No. 10, pp. 1327-1336.
O'Neill, A.C. et al., "Human Kidney Cell Reprogramming: Applications for Disease Modeling and Personalized Medicine", (Aug. 15, 2013), *Journal of the American Society of Nephrology*, vol. 24, No. 9, pp. 1347-1356.
Martovetsky, Gleb et al., "Cellular and Developmental Strategies Aimed at Kidney Tissue Engineering", (May 19, 2014), *Nephron Experimental Nephrology*, vol. 126, No. 2, pp. 101-106.
Piontek, K.B., "A Functional Floxed Allele of Pkd1 that can be Condionally Inactivated In Vivo", (Dec. 1, 2004), *Journal of the American Society of Nephrology*, vol. 15, No. 12, pp. 3035-3043.
Martovetsky, Gleb et al., "Hepatocyte Nuclear Factors 4 and 1 Regulate Kidney Developmental Expression of Drug-Metabolizing Enzymes and Drug Transporters", (Dec. 1, 2013), *Molecular Pharmacology*, vol. 84, No. 6, pp. 808-823.
Schmidt-Ott, K.M. et al., "Beta-Catenin/TCF/Lef Controls a Differentiation-Associated Transcriptional Program in Renal Epithelial Progenitors", (Sep. 1, 2007), *Development*, vol. 134, No. 17, pp. 3177-3190.
Guo-Xia, Tong et al., "Expression of PAX8 in Normal and Neoplastic Renal Tissues: An Immunohistochemical Study", (Jun. 12, 2009), *Modern Pathology*, vol. 22, No. 9, pp. 1218-1227.
Hedry, Caroline et al., "Direct Transcriptional Reprogramming of Adult Cells to Embryonic Nephron Progenitors", (Sep. 1, 2013), *Journal of the American Society of Nephrology*, vol. 24, No. 9, pp. 1424-1434.
Bruce, S.J. et al., "In Vitro Differentiation of Murine Embryonic Stem Cells Toward a Renal Lineage", (Jun. 1, 2007), *Differentiation*, vol. 75, No. 5, pp. 337-349.
Liu, Tao et al., "Induction of Hepatocyte-Like Cells from Mouse Embryonic Stem Cells by Lentivirus-Mediated Constitutive Expression of Foxa2/Hnf4a", (Sep. 13, 2013), *Journal of Cellular Biochemistry*, vol. 114, No. 11, pp. 2531-2541.

* cited by examiner

*Primary Examiner* — Robert M Kelly
(74) *Attorney, Agent, or Firm* — Smith Patent, LLC; Chalin A. Smith

(57) ABSTRACT

The present invention relates to a method for producing renal cells, comprising overexpressing Hnf1b and Pax8, and optionally Hnf4a and/or Emx2 in differentiated cells.

25 Claims, 38 Drawing Sheets

Specification includes a Sequence Listing.

| | E12 | E13 | E14 | E15 | E17 |
|---|---|---|---|---|---|
| *Emx2* | ub | te | te | te | te |
| *Esrrb* | - | - | - | - | te |
| *Foxc1* | mm | rv/g, nm, str | rv/g, nm, str | rv/g, nm, str | rv/g, nm, te |
| *Foxi1* | - | te | te | te | te |
| *Gata3* | ub | te | te | te | te |
| *Hnf1a* | - | - | te | te | te |
| *Hnf1b* | ub | te | rv/g, te | rv/g, te | rv/g, te |
| *Hnf4a* | - | rv/g | rv/g, te | rv/g, te | rv/g, te |
| *Hoxd9* | ub, mm | nm, str, te | nm, str, te | nm, str, te | str, te |
| *Hoxd11* | mm | nm, str | nm, str, te | nm, str, te | nm, str, te |
| *Lhx1* | ub | rv/g, te | rv/g, te | rv/g, te | rv/g, te |
| *Pax2* | ub, mm | rv/g, nm, te | rv/g, nm, te | rv/g, nm, te | rv/g, nm, te |
| *Pax8* | ub, mm | rv/g, nm, te | rv/g, nm, te | rv/g, nm, te | rv/g, nm, te |
| *Pou3f3* | ub | rv/g, te | rv/g, te | rv/g, te | rv/g, te |
| *Sall1* | mm | nm | rv/g, nm, te | rv/g, nm, te | rv/g, nm, te |
| *Tcf21* | mm | str | str, rv/g | str, rv/g | str, rv/g |
| *Tfap2a* | ub | te | te | te | te |
| *Tfap2b* | ub | rv/g, te | rv/g, te | rv/g, te | rv/g, te |
| *Tfcp2l1* | ub | te | rv/g, te | rv/g, te | rv/g, te |
| *Wt1* | mm | rv/g, nm | rv/g, nm | rv/g, nm | rv/g, nm |

-      no expression
- ub      ureteric bud, E12
- mm      metanephric mesenchyme, E12
- rv/g      renal vesicle/glomerulus, E13-E17
- nm      nephrogenic mesenchyme, E13-E17
- str      stroma/interstitium, E13-E17
- te      tubule epithelium, E13-E17

Figure 12b (left) and c (right)
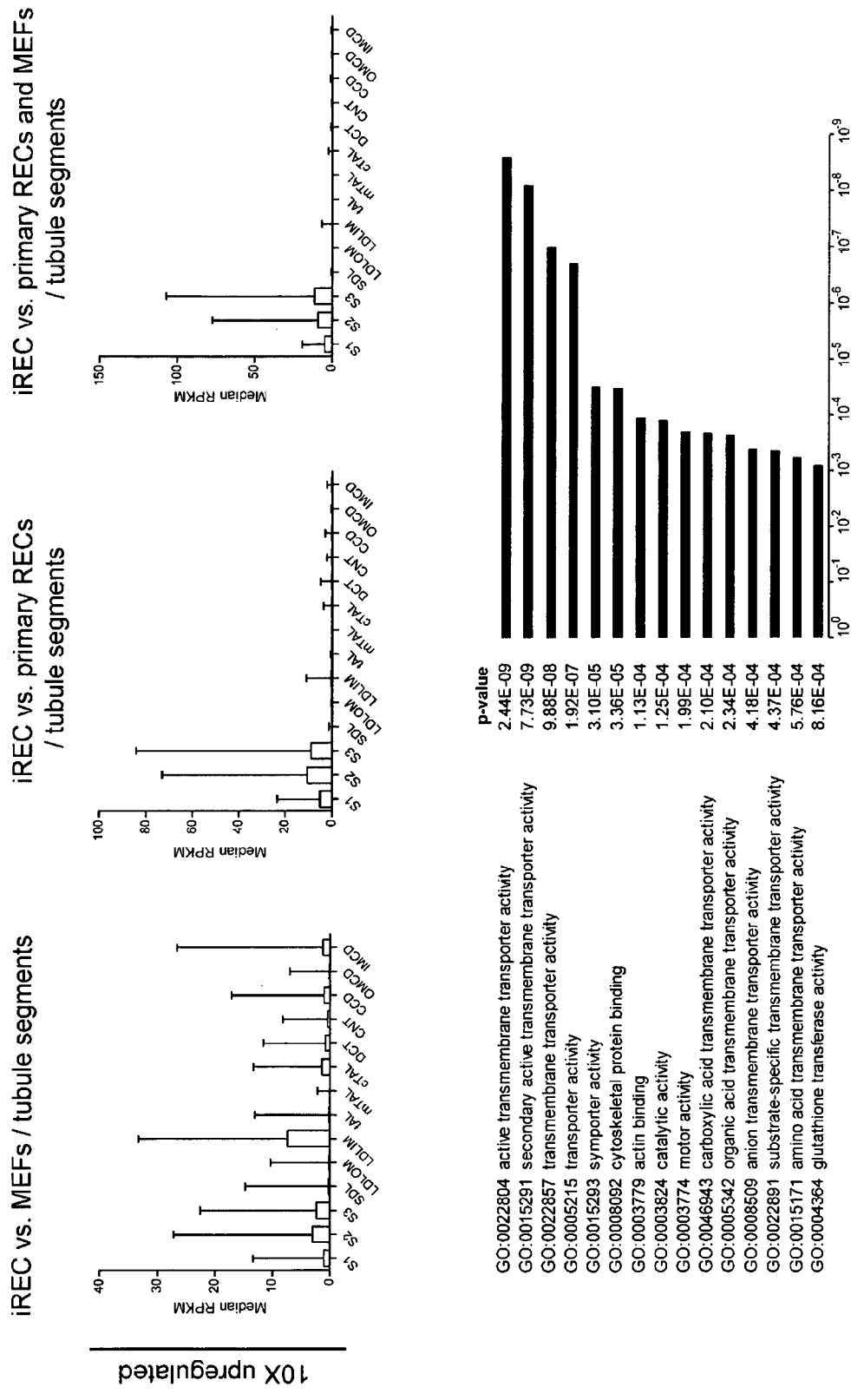

a b h i j a  b c d e a b c

SEQUENCE LISTING

<160> NUMBER OF SEQ ID NOS: 68

<210> SEQ ID NO 1
<211> LENGTH: 2908
<212> TYPE: DNA
<213> ORGANISM: Homo sapiens

<400> SEQUENCE: 1

```
cgggcgccgc aggagcgagt gagctgggag cgaggggcga aggcgcggag aagcccggcc      60
gcccggtggg cggcagaagg ctcagccgag gcggcggcgc cgactccgtt ccactctcgg     120
cccggatcca ggcctccggg ttcccaggcg ctcacctccc tctgacgcac tttaaagagt     180 ctccccccctt ccacctcagg gcgagtaata gcgaccaatc atcaagccat ttaccaggct     240
tcggaggaag ctgtttatgt gatccccgca ctaattaggc tcatgaacta acaaatcgtt     300
tgcacaactt gtgaagaagc gaacacttcc atggattgtc cttggactta gggcgccctg     360
cccgcctttt gcagaggaga aaaaactttt ttttttttt gcctcccccg agaactttcc     420 cccttctcc tccctgcctc taactccgat cccccacgc catctcgcca aaaaaaaaa     480 aaaaaaaaa aagaaaaaa aagaaaaaa aagaaaaaa aattacccca atccacgcct     540
gcaaattctt ctggaaggat tttccccccct ctcttcaggt tgggcgcgtt tggtgcaaga     600
ttctcgggat cctcggcttt gcctctccct ctccctcccc cctcctttcc ttttccttt     660 cctttccttt ctttcttcct ttccttcccc ccaccccac cccaccccca aacaaacgag     720
tccccaattc tcgtccgtcc tcgccgcggg cagcgggcgg cggaggcagc gtgcggcggt     780
cgccaggagc tgggagccca gggcgcccgc tcctcggcgc agcatgttcc agccggcgcc     840
caagcgctgc ttcaccatcg agtcgctggt ggccaaggac agtccctgc ccgcctcgcg     900 ctccgaggac cccatccgtc ccgcggcact cagctacgct aactccagcc ccataaatcc     960
```

| | |
|---|---|
| gttcctcaac ggcttccact cggccgccgc cgccgccgcc ggtaggggcg tctactccaa | 1020 |
| cccggacttg gtgttcgccg aggcggtctc gcacccgccc aaccccgccg tgccagtgca | 1080 |
| cccggtgccg ccgccgcacg ccctggccgc ccacccccta ccctcctcgc actcgccaca | 1140 |
| cccctattc gcctcgcagc agcgggatcc gtccaccttc taccctggc tcatccaccg | 1200 |
| ctaccgatat ctgggtcatc gcttccaagg gaacgacact agccccgaga gtttccttt | 1260 |
| gcacaacgcg ctggcccgaa agcccaagcg gatccgaacc gccttctccc cgtcccagct | 1320 |
| tctaaggctg gaacacgcct ttgagaagaa tcactacgtg gtgggcgccg aaaggaagca | 1380 |
| gctggcacac agcctcagcc tcacggaaac tcaggtaaaa gtatggtttc agaaccgaag | 1440 |
| aacaaagttc aaaaggcaga agctggagga agaaggctca gattcgcaac aaaagaaaaa | 1500 |
| agggacgcac catattaacc ggtggagaat cgccaccaag caggcgagtc cggaggaaat | 1560 |
| agacgtgacc tcagatgatt aaaaacataa acctaacccc acagaaacgg acaacatgga | 1620 |
| gcaaaagaga cagggagagg tggagaagga aaaaacccta caaacaaaa acaaaccgca | 1680 |
| tacacgttca ccgagaaagg gagagggaat cggagggagc agcggaatgc ggcgaagact | 1740 |
| ctggacagcg agggcacagg gtcccaaacc gaggccgcgc caagatggca gaggatggag | 1800 |
| gctccttcat caacaagcga ccctcgtcta aagaggcagc tgagtgagag acacagagag | 1860 |
| aaggagaaag agggagggag agagagaaag agagagaaag agagagagag agagagagag | 1920 |
| agaaagctga acgtgcactc tgacaagggg agctgtcaat caaacaccaa accggggaga | 1980 |
| caagatgatt ggcaggtatt ccgtttatca cagtccactt aaaaaatgat gatgatgata | 2040 |
| aaaaccacga cccaaccagg cacaggactt ttttgttttt tgcacttcgc tgtgtttccc | 2100 |
| ccccatcttt aaaataatt agtaataaaa aacaaaaatt ccatatctag ccccatccca | 2160 |
| cacctgtttc aaatccttga aatgcatgta gcagttgttg ggcgaatggt gtttaaagac | 2220 |
| cgaaaatgaa ttgtaatttt cttttccttt taaagacagg ttctgtgtgc tttttatttt | 2280 |
| gattttttt cccaagaaat gtgcagtctg taaacacttt ttgataccct ctgatgtcaa | 2340 |
| agtgattgtg caagctaaat gaagtaggct cagcgatagt ggtcctctta cagagaaacg | 2400 |
| gggagcagga cgacgggggg gctggggtg gcggggagg gtgcccacaa aaagaatcag | 2460 |
| gacttgtact gggaaaaaaa cccctaaatt aattatattt cttggacatt ccctttccta | 2520 |
| acatcctgag gcttaaaacc ctgatgcaaa cttctccttt cagtggttgg agaaattggc | 2580 |
| cgagttcaac cattcactgc aatgcctatt ccaaacttta aatctatcta ttgcaaaacc | 2640 |
| tgaaggacta tagttagcgg ggatgatgtt aagtgtggcc aagcgcacgg cggcaagttt | 2700 |
| tcaagcactg agtttctatt ccaagatcat agacttacta aagagagtga caaatgcttc | 2760 |
| cttaatgtct tctataccag aatgtaaata tttttgtgtt ttgtgttaat tgttagaat | 2820 |
| tctaacacac tatatacttc caagaagtat gtcaatgtca atattttgtc aataaagatt | 2880 |
| tatcaatatg ccctcaaaaa aaaaaaaa | 2908 |

<210> SEQ ID NO 2
<211> LENGTH: 2818
<212> TYPE: DNA
<213> ORGANISM: Homo sapiens

<400> SEQUENCE: 2

| | |
|---|---|
| atcatggcaa gttagaagtt ttctgactcc tttcggagga gcctccggga ccccggggag | 60 |
| taacaggtgt ctggaggctg aagggtggag gggttcctgg atttgggt tgcttgtgaa | 120 |
| actcccctcc accctcctct ctcgcaccca cccaccccct caccccttc tttttccgtc | 180 |

```
cttggaaaat ggtgtccaag ctcacgtcgc tccagcaaga actcctgagc gccctgctga    240
gctccggggt caccaaggag gtgctggttc aggccttgga ggagttgctg ccatccccga    300 acttcgggt  gaagctggag acgctgcccc tgtccctgg  cagcggggcc gagcccgaca    360
ccaagccggt cttccatact ctcaccaacg gccacgccaa gggccgcttg tccggcgacg    420
agggctccga ggacggcgac gactatgaca cacctcccat cctcaaggag ctgcaggcgc    480
tcaacaccga ggaggcggcg gagcagcggg cggaggtgga ccggatgctc agtgaggacc    540
cttggagggc tgctaaaatg atcaagggtt acatgcagca acacaacatc ccccagaggg    600
aggtggtcga tgtcaccggc ctgaaccagt cgcacctctc ccagcatctc aacaagggca    660
cccctatgaa gacccagaag cgtgccgctc tgtacacctg gtacgtcaga aagcaacgag    720
agatcctccg acaattcaac cagacagtcc agagttctgg aaatatgaca gacaaaagca    780
gtcaggatca gctgctgttt ctctttccag agttcagtca acagagccat gggcctgggc    840
agtccgatga tgcctgctct gagcccacca acaagaagat gcgccgcaac cggttcaaat    900
gggggcccgc gtcccagcaa atcttgtacc aggcctacga tcggcaaaag aaccccagca    960
aggaagagag agaggcctta gtggaggaat gcaacagggc agaatgtttg cagcgagggg   1020
tgtccccctc caaagcccac ggcctgggct ccaacttggt cactgaggtc cgtgtctaca   1080
actggtttgc aaaccgcagg aaggaggagg cattccggca aaagctggcc atggacgcct   1140
atagctccaa ccagactcac agcctgaacc ctctgctctc ccacggctcc cccaccacc   1200 agcccagctc ctctcctcca aacaagctgt caggagtgcg ctacagccag cagggaaaca   1260
atgagatcac ttcctcctca caatcagtc  accatggcaa cagcgccatg gtgaccagcc   1320
agtcggtttt acagcaagtc tccccagcca gcctggaccc aggccacaat ctcctctcac   1380
ctgatggtaa aatgatctca gtctcaggag gaggtttgcc cccagtcagc accttgacga   1440
atatccacag cctctcccac cataatcccc agcaatctca aaacctcatc atgcaccccc   1500
tctctggagt catggcaatt gcacaaagcc tcaacacctc ccaagcacag agtgtccctg   1560
tcatcaacag tgtggccggc agcctggcag ccctgcagcc cgtccagttc tcccagcagc   1620
tgcacagccc tcaccagcag cccctcatgc agcagagccc aggcagccac atggcccagc   1680 agccccttcat ggcagctgtg actcagctgc agaactcaca catgtacgca cacaagcagg   1740
aaccccccca gtattcccac acctcccggt ttccatctgc aatggtggtc acagatacca   1800
gcagcatcag tacactcacc aacatgtctt caagtaaaca gtgtcctcta caagcctggt   1860
gatgcccaca caccacttac ttcgtgcgca acaacaagga ccctgttttc cacaccatca   1920
ccctctgggc agctgtcatg gaaaagccca gtgacctgac cagcacctgc gagaggtccc   1980
tgcttacctg acggacgtcc tgctggcacc tcagacaatc cactctcagg aggcgcagcc   2040
cgaagcccag tttcccttct atgcagtatt gccacaatgc ctctcccacg atgtcaagga   2100
ctcctgtctg tcctggaggt gggagacaag gaacctccga agaggaagca agaaagccgt   2160
actgtctatg ttgtgatcct tcatcgaaca aactgatgcg aaaacttgaa tctgttactg   2220
aaatgaggag agaaggacat gtgctattga actgagccaa acacactgta aatatccaca   2280
gactccctcc cctgccccca tcccaaatga tcttgagatt tctttttaaag aagtaaattt   2340 gtccaatggc tgtaaactat aaactactgt aattaagtgc aatttcccct ctgtgtcctc   2400
tcccctctgc cctgtatata atactaaagt gtcattagt  tttctttgta aaggtcagag   2460
tcaaaatttc aaaagtgatc tgtccctct  cccctcatgg agaaacatcc taagtgggaa   2520
```

| | |
|---|---|
| gtgaagcccc ttgtcctctc ccgcgggcct ggacacttat ggggacagca taccttggac | 2580 |
| tgactaccag ctaactccag tctcctgaca ttaagacaca cctctggatc cctggagggg | 2640 |
| ctgaatgtag tgtgtcagag taacatgcca gcttcctgtg gccaggagc tcagccgtgc | 2700 |
| actccctaag aaaccccagg gcagggaaac tggctgtttg atagcagaag aaaaagttgc | 2760 |
| agtctcagaa agccttccat taaaacaatt tattttatca ctaaaaaaaa aaaaaaaa | 2818 |

<210> SEQ ID NO 3
<211> LENGTH: 4737
<212> TYPE: DNA
<213> ORGANISM: Homo sapiens

<400> SEQUENCE: 3

| | |
|---|---|
| ggtttgaaag gaaggcagag agggcactgg gaggaggcag tgggagggcg gagggcgggg | 60 |
| gccttcgggg tgggcgccca gggtagggca ggtggccgcg gcgtggaggc agggagaatg | 120 |
| cgactctcca aaaccctcgt cgacatggac atggccgact acagtgctgc actggaccca | 180 |
| gcctacacca ccctggaatt tgagaatgtg caggtgttga cgatgggcaa tgacacgtcc | 240 |
| ccatcagaag gcaccaacct caacgcgccc aacagcctgg gtgtcagcgc cctgtgtgcc | 300 |
| atctgcgggg accgggccac gggcaaacac tacggtgcct cgagctgtga cggctgcaag | 360 |
| ggcttcttcc ggaggagcgt gcggaagaac cacatgtact cctgcagatt tagccggcag | 420 |
| tgcgtggtgg acaaagacaa gaggaaccag tgccgctact gcaggctcaa gaaatgcttc | 480 |
| cgggctggca tgaagaagga agccgtccag aatgagcggg accggatcag cactcgaagg | 540 |
| tcaagctatg aggacagcag cctgccctcc atcaatgcgc tcctgcaggc ggaggtcctg | 600 |
| tcccgacaga tcacctcccc cgtctccggg atcaacggcg acattcgggc gaagaagatt | 660 |
| gccagcatcg cagatgtgtg tgagtccatg aaggagcagc tgctggttct cgttgagtgg | 720 |
| gccaagtaca tcccagcttt ctgcgagctc ccctggacg accaggtggc cctgctcaga | 780 |
| gcccatgctg gcgagcacct gctgctcgga gccaccaaga gatccatggt gttcaaggac | 840 |
| gtgctgctcc taggcaatga ctacattgtc cctcggcact gcccggagct ggcggagatg | 900 |
| agccgggtgt ccatacgcat cccttgacga gctggtgctg cccttccagga gctgcagatc | 960 |
| gatgacaatg agtatgccta cctcaaagcc atcatcttct ttgacccaga tgccaagggg | 1020 |
| ctgagcgatc cagggaagat caagcggctg cgttcccagg tgcaggtgag cttggaggac | 1080 |
| tacatcaacg accgccagta tgactcgcgt ggccgctttg agagctgctg ctgctgctg | 1140 |
| cccaccttgc agagcatcac ctggcagatg atcgagcaga tccagttcat caagctcttc | 1200 |
| ggcatggcca agattgacaa cctgttgcag gagatgctgc tgggagggtc ccccagcgat | 1260 |
| gcaccccatg cccaccaccc cctgcaccct cacctgatgc aggaacatat gggaaccaac | 1320 |
| gtcatcgttg ccaacacaat gcccactcac ctcagcaacg acagatgtg tgagtggccc | 1380 |
| cgacccaggg acaggcagc caccctgag accccacagc cctcaccgcc aggtggctca | 1440 |
| gggtctgagc cctataagct cctgccggga ccgtcgcca caatcgtcaa gcccctctct | 1500 |
| gccatccccc agccgaccat caccaagcag gaagttatct agcaagccgc tggggcttgg | 1560 |
| gggctccact ggctccccc agccccctaa gagagcacct ggtgatcacg tggtcacggc | 1620 |
| aaaggaagac gtgatgccag gaccagtccc agagcaggaa tgggaaggat gaagggcccg | 1680 |
| agaacatggc ctaagggcca catcccactg ccacccttga cgccctgctc tggataacaa | 1740 |
| gactttgact tggggagacc tctactgcct tggacaactt ttctcatgtt gaagccactg | 1800 |
| ccttcacctt caccttcatc catgtccaac ccccgacttc atcccaaagg acagccgcct | 1860 |

```
ggagatgact tgaggcctta cttaaaccca gctcccttct tccctagcct ggtgcttctc    1920
ctctcctagc ccctgtcatg gtgtccagac agagccctgt gaggctgggt ccaattgtgg    1980
cacttggggc accttgctcc tccttctgct gctgccccca cctctgctgc ctccctctgc    2040
tgtcaccttg ctcagccatc ccgtcttctc aacaccacc tctccagagg ccaaggaggc     2100
cttggaaacg attcccccag tcattctggg aacatgttgt aagcactgac tgggaccagg    2160
caccaggcag ggtctagaag gctgtggtga gggaagacgc ctttctcctc caacccaacc    2220
tcatcctcct tcttcaggga cttgggtggg tacttgggtg aggatccctg aaggccttca    2280
acccgagaaa acaaacccag gttggcgact gcaacaggaa cttggagtgg agaggaaaag    2340
catcagaaag aggcagacca tccaccaggc ctttgagaaa gggtagaatt ctggctggta    2400
gagcaggtga gatgggacat tccaaagaac agcctgagcc aaggcctagt ggtagtaaga    2460
atctagcaag aattgaggaa gaatggtgtg ggagagggat gatgaagaga gagagggcct    2520
gctggagagc atagggtctg gaacaccagg ctgaggtcct gatcagcttc aaggagtatg    2580
cagggagctg ggcttccaga aaatgaacac agcagttctg cagaggacgg gaggctggaa    2640
gctgggaggt caggtggggt ggatgatata atgcgggtga gagtaatgag gcttggggct    2700
ggagaggaca agatgggtaa accctcacat cagagtgaca tccaggagga ataagctccc    2760
agggcctgtc tcaagctctt ccttactccc aggcactgtc ttaaggcatc tgacatgcat    2820
catctcattt aatcctccct tcctccctat taacctagag attgttttg ttttttattc     2880 tcctcctccc tccccgccct cacccgcccc actccctcct aacctagaga ttgttacaga    2940
agctgaaatt gcgttctaag aggtgaagtg atttttttc tgaaactcac acaactagga     3000
agtggctgag tcaggacttg aacccaggtc tccctggatc agaacaggag ctcttaacta    3060
cagtggctga atagcttctc caaaggctcc ctgtgttctc accgtgatca agttgagggg    3120
cttccggctc ccttctacag cctcagaaac cagactcgtt cttctgggaa ccctgcccac    3180
tcccaggacc aagattggcc tgaggctgca ctaaaattca cttagggtcg agcatcctgt    3240
ttgctgataa atattaagga gaattcatga ctcttgacag cttttctctc ttcactcccc    3300
aagtcaaggg gaggggtggc aggggtctgt ttcctggaag tcaggctcat ctggcctgtt    3360
ggcatggggg tgggacagtg tgcacagtgt gggggcaggg gagggctaag caggcctggg    3420
tttgagggct gctccggaga ccgtcactcc aggtgcattc tggaagcatt agaccccagg    3480
atggagcgac cagcatgtca tccatgtgga atcttggtgg ctttgaggac attctggaaa    3540
atgccactga ccagtgtgaa caaaagggat gtgttatggg gctggaggtg tgattaggta    3600
ggagggaaac tgttggaccg actcctgccc cctgctcaac actgacccct ctgagtggtt    3660
ggaggcagtg ccccagtgcc cagaaatccc accattagtg attgtttttt atgagaaaga    3720
ggcgtggaga agtattgggg caatgtgtca gggaggaatc accacatccc tacggcagtc    3780
ccagccaagc ccccaatccc agcggagact gtgccctgct cagagctccc aagccttccc    3840
ccaccacctc actcaagtgc ccctgaaatc cctgccagac ggctcagcct ggtctgcggt    3900
aaggcaggga ggctggaacc atttctgggc attgtggtca ttcccactgt gttcctccac    3960
ctcctccctc cagcgttgct cagacctctg tcttgggaga aaggttgaga taagaatgtc    4020
ccatggagtg ccgtgggcaa cagtggccct tcatgggaac aatctgttgg agcaggggt     4080 cagttctctg ctgggaatct acccctttct ggaggagaaa cccattccac cttaataact    4140
ttattgtaat gtgagaaaca caaaacaaag tttactttt tgactctaag ctgacatgat     4200
```

| | |
|---|---:|
| attagaaaat ctctcgctct cttttttttt tttttttttt ttttttggcta cttgagttgt | 4260 |
| ggtcctaaaa cataaaatct gatggacaaa cagagggttg ctgggggggac aagcgtgggc | 4320 |
| acaatttccc caccaagaca ccctgatctt caggcgggtc tcaggagctt ctaaaaatcc | 4380 |
| gcatggctct cctgagagtg gacagaggag aggagagggt cagaaatgaa cgctcttcta | 4440 |
| tttcttgtca ttaccaagcc aattactttt gccaattttt tctgtgatct gccctgatta | 4500 |
| agatgaattg tgaaatttac atcaagcaat tatcaaagcg ggctgggtcc catcagaacg | 4560 |
| acccacatct ttctgtgggt gtgaatgtca ttaggtcttg cgctgacccc tgagccccca | 4620 |
| tcactgccgc ctgatggggc aaagaaacaa aaaacatttc ttactcttct gtgttttaac | 4680 |
| aaaagtttat aaaacaaaat aaatggcgca tatgttttct aaaaaaaaaa aaaaaaa | 4737 |

<210> SEQ ID NO 4
<211> LENGTH: 2698
<212> TYPE: DNA
<213> ORGANISM: Homo sapiens

<400> SEQUENCE: 4

| | |
|---|---:|
| cttcagaagg aggagagaca ccgggcccag ggcaccctcg cgggcggacc caagcagtga | 60 |
| gggcctgcag ccggccggcc agggcagcgg caggcgcggc ccggacctac gggaggaagc | 120 |
| cccgagccct cggcgggctg cgagcgactc cccggcgatg cctcacaact ccatcagatc | 180 |
| tggccatgga gggctgaacc agctggggagg ggcctttgtg aatggcagac tctgccggaa | 240 |
| agtggtccgc cagcgcatcg tagacctggc ccaccagggt gtaaggccct gcgacatctc | 300 |
| tcgccagctc cgcgtcagcc atggctgcgt cagcaagatc cttggcaggt actacgagac | 360 |
| tggcagcatc cggcctggag tgatagggggg ctccaagccc aaggtggcca ccccaaggt | 420 |
| ggtggagaag attgggggact acaaacgcca gaaccctacc atgtttgcct gggagatccg | 480 |
| agaccggctc ctggctgagg gcgtctgtga caatgacact gtgcccagtg tcagctccat | 540 |
| taatagaatc atccggacca agtgcagca accattcaac ctccctatgg acagctgcgt | 600 |
| ggccaccaag tccctgagtc ccggacacac gctgatcccc agctcagctg taactccccc | 660 |
| ggagtcaccc cagtcggatt ccctgggctc cacctactcc atcaatgggc tcctgggcat | 720 |
| cgctcagcct ggcagcgaca agaggaaaat ggatgacagt gatcaggata gctgccgact | 780 |
| aagcattgac tcacagagca gcagcagcgg accccgaaag caccttcgca cggatgcctt | 840 |
| cagccagcac caccctcgagc cgctcgagtg cccatttgag cggcagcact acccagaggc | 900 |
| ctatgcctcc cccagccaca ccaaaggcga gcagggcctc tacccgctgc ccttgctcaa | 960 |
| cagcaccctg gacgacggga aggccaccct gacccccttcc aacacgccac tggggcgcaa | 1020 |
| cctctcgact caccagacct accccgtggt ggcagatcct cactcacccct tcgccataaa | 1080 |
| gcaggaaacc cccgaggtgt ccagttctag ctccacccct tcctctttat ctagctccgc | 1140 |
| cttttttggat ctgcagcaag tcggctccgg ggtcccgccc ttcaatgcct ttccccatgc | 1200 |
| tgcctccgtg tacgggcagt tcacgggcca ggccctcctc tcaggcgag agatggtggg | 1260 |
| gcccacgctg cccggatacc acccccacat ccccaccagc ggacagggca gctatgcctc | 1320 |
| ctctgccatc gcaggcatgg tggcaggaag tgaatactct ggcaatgcct atggccacac | 1380 |
| ccctactcc tcctacagcg aggcctggcg cttccccaac tccagcttgc tgagttcccc | 1440 |
| atattattac agttccacat caaggccgag tgcaccgccc accactgcca cggcctttga | 1500 |
| ccatctgtat ttgccatggg gacagtggga gcgactgagc aacaggagga ctcagcctgg | 1560 |
| gacaggcccc agagagtcac acaaaggaat ctttatttat tacatgaaaa ataaccacaa | 1620 |

-continued

```
gtccagcatt gcggcacact ccctgtgtgg ttaatttaat gaaccatgaa agacaggatg    1680
accttggaca aggccaaact gtcctccaag actccttaat gaggggcagg agtcccaggg    1740
aaagagaacc atgccatgct gaaaaagaca aaattgaaga agaaatgtag cccccagccg    1800
gtacccacca aaggagagaa gaagcaatag ccgaggaact tgggggatg gcgaatggtt     1860 cctgcccggg cccaagggt gcacagggca cctccatggc tccattatta acacaactct     1920
agcaattatg gaccataagc acttccctcc agcccacaag tcacagcctg gtgccgaggc    1980
tctcctcacc agccacccag ggagtcacct ccctcagcct cccgcctgcc ccacacggag    2040
gctctggctg tcctctttct ccactccatt tgcttggctc tttctacacc tccctcttgg    2100
gcatgggctg agggctggag cgagtccctc agaaattcca ccaggctgtc agctgacctc    2160
ttttgcctgc tgctgtgaag gtatagcacc accccaggtc ctcctgcagt gcggcatccc    2220
cttggcagct gccgtcagcc aggccagccc cagggagctt aaaacagaca ttccacaggg    2280
cctgggcccc tgggaggtga ggtgtggtgt gcggcttcac ccagggcaga acaaggcaga    2340
atcgcaggaa acccgcttcc ccttcctgac agctcctgcc aagccaaatg tgcttcctgc    2400
agctcacgcc caccagctac tgaagggacc caaggcaccc cctgaagcca gcgatagagg    2460
gtccctctct gctccccagc agctcctgcc cccaaggcct gactgtatat actgtcaatg    2520
aaactttgtt tgggtcaagc ttccttcttt ctacccccca gactttggcc tctgagtgaa    2580
atgtctctct ttgccctgtg gggcttctct ccttgatgct tctttctttt tttaaagaca    2640
acctgccatt accacatgac tcaataaacc attgctcttc aaaaaaaaaa aaaaaaa      2698
```

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
ctatggggtt gcatcatgtg aa                                             22

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cgtctgcgct ttgtgatctc                                                20

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
gacctgaccg agttgcctaa t                                              21

<210> SEQ ID NO 8
<211> LENGTH: 20
<212> TYPE: DNA
<213> ORGANISM: Artificial Sequence
<220> FEATURE:

```
<223> OTHER INFORMATION: Primer

<400> SEQUENCE: 8
ccggctcttt cagaatgggt                                                        20

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
cccatcctgg accgtttcc                                                         19

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
cgcttggaga gatgccctg                                                         19

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
gcttgatgtg ctacaaaagc tg                                                     22

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
cgtggtgatg gttgaatgtc c                                                      21

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
aagcccggag tgattggtg                                                         19

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
caggcgaaca tagtcgggtt                                                        20
```

```
<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gctggagaat cggaagctag g                                              21

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
aaaacgacac ggatgatgct c                                              21

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gtgcagcgta agcgagagat                                                20

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
ggatggcgat aatgtgctgt tg                                             22

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gtgtggattc ccttgggctt t                                              21

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
cacaacgaac acctgcttgg                                                20

<210> SEQ ID NO 21
<211> LENGTH: 21
<212> TYPE: DNA
<213> ORGANISM: Artificial Sequence
<220> FEATURE:
<223> OTHER INFORMATION: Primer
```

```
<400> SEQUENCE: 21
tttgtcatca tcggcctctg t                                              21

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
cccgtccaat ctctgagcag                                                20

<210> SEQ ID NO 23
<211> LENGTH: 18
<212> TYPE: DNA
<213> ORGANISM: Artificial Sequence
<220> FEATURE:
<223> OTHER INFORMATION: Primer

<400> SEQUENCE: 23
acacttgtgg gcattctc                                                  18

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gcagtcatta tcaccatcac                                                20

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
tgctttgcct gtttcctctc a                                              21

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
atgtcatcac agaaccgttt cat                                            23

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
ccaaggacca cccgtatatg a                                              21

<210> SEQ ID NO 28
<211> LENGTH: 22
```

```
<212> TYPE: DNA
<213> ORGANISM: Artificial Sequence
<220> FEATURE:
<223> OTHER INFORMATION: Primer

<400> SEQUENCE: 28
ctttgattgg cagggattgt ct                                             22

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
aaagcagcat gaggtcgtgg                                                20

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
actgaagcac gtcaggtaat g                                              21

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
gccgattgaa gactttgagg                                                20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ctacggcact taccgtcacc                                                20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
aagtacatcc tctattctca                                                20

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
```

```
attctgatct gtcactgt                                                    18

<210> SEQ ID NO 35
<211> LENGTH: 19
<212> TYPE: DNA
<213> ORGANISM: Artificial Sequence
<220> FEATURE:
<223> OTHER INFORMATION: Primer

<400> SEQUENCE: 35
gcaacggaga ttaataacc                                                   19

<210> SEQ ID NO 36
<211> LENGTH: 19
<212> TYPE: DNA
<213> ORGANISM: Artificial Sequence
<220> FEATURE:
<223> OTHER INFORMATION: Primer

<400> SEQUENCE: 36
tcatagaact cagcaaact                                                   19

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
ataccaacta caggtcac                                                    18

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
gtcattctca tctttcacat                                                  20

<210> SEQ ID NO 39
<211> LENGTH: 19
<212> TYPE: DNA
<213> ORGANISM: Artificial Sequence
<220> FEATURE:
<223> OTHER INFORMATION: Primer

<400> SEQUENCE: 39
ccttcttggg tatggaatc                                                   19

<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
cactgtgttg gcatagag                                                    18

<210> SEQ ID NO 41
<211> LENGTH: 22
<212> TYPE: DNA
<213> ORGANISM: Artificial Sequence
```

```
<220> FEATURE:
<223> OTHER INFORMATION: Primer

<400> SEQUENCE: 41
agaacaatcc agactagcag ca                                              22

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
gggaacttca catcacagct c                                               21

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
aacacctcaa caagggcact c                                               21

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
ccccacttga aacggttcct                                                 20

<210> SEQ ID NO 45
<211> LENGTH: 22
<212> TYPE: DNA
<213> ORGANISM: Artificial Sequence
<220> FEATURE:
<223> OTHER INFORMATION: Primer

<400> SEQUENCE: 45
gactttggac catgaagacc ag                                              22

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
gcccagacgg aagtttctta tt                                              22

<210> SEQ ID NO 47
<211> LENGTH: 23
<212> TYPE: DNA
<213> ORGANISM: Artificial Sequence
<220> FEATURE:
<223> OTHER INFORMATION: Primer

<400> SEQUENCE: 47
cgtttaagca gaacgagaat ggg                                             23
```

<210> SEQ ID NO 48
<211> LENGTH: 23
<212> TYPE: DNA
<213> ORGANISM: Artificial Sequence
<220> FEATURE:
<223> OTHER INFORMATION: Primer

<400> SEQUENCE: 48
tttcatagga cggctggtat ttc                                          23

<210> SEQ ID NO 49
<211> LENGTH: 22
<212> TYPE: DNA
<213> ORGANISM: Artificial Sequence
<220> FEATURE:
<223> OTHER INFORMATION: Primer

<400> SEQUENCE: 49
agaatgacaa cgtgcctatc tg                                           22

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
gctgacagtc tagtcacttc agt                                          23

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
ataacctgct ctgagcgagt g                                            21

<210> SEQ ID NO 52
<211> LENGTH: 22
<212> TYPE: DNA
<213> ORGANISM: Artificial Sequence
<220> FEATURE:
<223> OTHER INFORMATION: Primer

<400> SEQUENCE: 52
tgcagtccgc aaactttac ta                                            22

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
ctggggagat ccgaggctat                                              20

<210> SEQ ID NO 54
<211> LENGTH: 21
<212> TYPE: DNA
<213> ORGANISM: Artificial Sequence
<220> FEATURE:
<223> OTHER INFORMATION: Primer -continued

```
<400> SEQUENCE: 54
gatgacggtc cgcttgtttt c                                              21

<210> SEQ ID NO 55
<211> LENGTH: 21
<212> TYPE: DNA
<213> ORGANISM: Artificial Sequence
<220> FEATURE:
<223> OTHER INFORMATION: Primer

<400> SEQUENCE: 55
ggcctgctat aacaccagtc a                                              21

<210> SEQ ID NO 56
<211> LENGTH: 23
<212> TYPE: DNA
<213> ORGANISM: Artificial Sequence
<220> FEATURE:
<223> OTHER INFORMATION: Primer

<400> SEQUENCE: 56
actcattgtg caagcatatc tca                                            23

<210> SEQ ID NO 57
<211> LENGTH: 23
<212> TYPE: DNA
<213> ORGANISM: Artificial Sequence
<220> FEATURE:
<223> OTHER INFORMATION: Primer

<400> SEQUENCE: 57
tctgttcctt tcgctatgga ttg                                            23

<210> SEQ ID NO 58
<211> LENGTH: 21
<212> TYPE: DNA
<213> ORGANISM: Artificial Sequence
<220> FEATURE:
<223> OTHER INFORMATION: Primer

<400> SEQUENCE: 58
ttgggcaaac catgtggatc t                                              21

<210> SEQ ID NO 59
<211> LENGTH: 22
<212> TYPE: DNA
<213> ORGANISM: Artificial Sequence
<220> FEATURE:
<223> OTHER INFORMATION: Primer

<400> SEQUENCE: 59
tctgggtatc ggaaagcaag cc                                             22

<210> SEQ ID NO 60
<211> LENGTH: 22
<212> TYPE: DNA
<213> ORGANISM: Artificial Sequence
<220> FEATURE:
<223> OTHER INFORMATION: Primer

<400> SEQUENCE: 60
gtgcacttcc tcaggcatct tg                                             22

<210> SEQ ID NO 61
```

```
<211> LENGTH: 19
<212> TYPE: DNA
<213> ORGANISM: Artificial Sequence
<220> FEATURE:
<223> OTHER INFORMATION: Primer p16 Forward

<400> SEQUENCE: 61
cggtcgtacc ccgattcag                                                    19

<210> SEQ ID NO 62
<211> LENGTH: 22
<212> TYPE: DNA
<213> ORGANISM: Artificial Sequence
<220> FEATURE:
<223> OTHER INFORMATION: Primer p16 reverse

<400> SEQUENCE: 62
gcaccgtagt tgagcagaag ag                                                22

<210> SEQ ID NO 63
<211> LENGTH: 25
<212> TYPE: DNA
<213> ORGANISM: Artificial Sequence
<220> FEATURE:
<223> OTHER INFORMATION: primer

<400> SEQUENCE: 63
caccgtgcct ggagcaggac gaaag                                             25

<210> SEQ ID NO 64
<211> LENGTH: 25
<212> TYPE: DNA
<213> ORGANISM: Artificial Sequence
<220> FEATURE:
<223> OTHER INFORMATION: primer

<400> SEQUENCE: 64
caccgtgcct ggagcaggac gaaag                                             25

<210> SEQ ID NO 65
<211> LENGTH: 20
<212> TYPE: DNA
<213> ORGANISM: Artificial Sequence
<220> FEATURE:
<223> OTHER INFORMATION: primer

<400> SEQUENCE: 65
gccatggtta actccagacg                                                   20

<210> SEQ ID NO 66
<211> LENGTH: 18
<212> TYPE: DNA
<213> ORGANISM: Artificial Sequence
<220> FEATURE:
<223> OTHER INFORMATION: primer

<400> SEQUENCE: 66
gcgcaggcag ttgtcaag                                                     18

<210> SEQ ID NO 67
<211> LENGTH: 23
<212> TYPE: DNA
<213> ORGANISM: Artificial Sequence
<220> FEATURE:
<223> OTHER INFORMATION: sequence shown in Fig. 16c

<400> SEQUENCE: 67
```

```
ccgctttcgt cctgctccag gca                                              23

<210> SEQ ID NO 68
<211> LENGTH: 65
<212> TYPE: DNA
<213> ORGANISM: Artificial Sequence
<220> FEATURE:
<223> OTHER INFORMATION: sequencing result of Fig. 16c

<400> SEQUENCE: 68
cggccggagc ctcggcctcg ccgtctcctc cgctttcgtc ctgctccggg caagcgtgga    60
gccgc                                                                  65
```

METHOD OF PRODUCING RENAL CELLS FROM DIFFERENTIATED CELLS

PRIORITY

This application corresponds to the national phase of International Application No. PCT/EP2017/051504 filed Jan. 25, 2017, which, in turn, claims priority to European Patent Application No. 16.152655.3 filed Jan. 25, 2016 and European Patent Application No. 16.185290.0 filed Aug. 23, 2016, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Jun. 19, 2018, is named LNK_190US_SL_ST25.txt and is 29,346 bytes in size.

BACKGROUND

End-stage renal disease is a major public health burden with a growing incidence of 100,000 new cases per year in the US[1]. Therefore, the in vitro generation of renal cells represents a major challenge for kidney disease related research and regenerative medicine.

A number of studies have directed pluripotent cells towards a renal cell fate in vitro. Embryonic stem cells or induced pluripotent cells (iPSCs) that were cultured in the presence of defined growth factor cocktails or chemical compounds acquired renal cell characteristics[2-6]. These multistep protocols aimed to recapitulate the path of renal embryonic differentiation[3, 6] and generated self-organizing kidney-like organoids that contained segmented nephrons[2, 4], which were surrounded by endothelial cells and renal interstitium[5]. In a different approach, bone-marrow-derived mesenchymal stem cells were conditioned by cell-free extracts from a proximal tubule cell line to form tubule-like cells in vitro[7]. However, all of these approaches depend on the availability of pluri- or multipotent stem cell populations, and include intricate differentiation protocols. In addition, the use of human ESCs raises ethical concerns, and the tumorigenic risk of iPSC-derived cells currently limits their clinical use[8].

Direct reprogramming is an alternative approach to generate desired cell types in vitro[9]. Differentiated cells, such as fibroblasts, can be reprogrammed by defined transcription factors into organ-specific cell types bypassing a pluripotent stage. Fibroblasts have been directly reprogrammed to neurons[10], oligodendrocytes[11, 12], cardiomyocytes[13], hepatocytes[14-16] or Sertoli cells[17], but not yet to any renal cell type. Previously, the expression of six transcription factors, Six1, Six2, Osr1, Eya1, Hoxa11, Snai2, in combination with valproic acid treatment induces de-differentiation of a proximal tubule cell line into a precursor state[18]. However, this approach requires viable renal tubule cells, thus limiting its use in the majority of clinical settings of kidney disease. Direct reprogramming of fibroblasts towards a mature renal cell type has not been reported to date.

SUMMARY OF THE INVENTION

The inventors identified four transcription factors—Emx2, Hnf1b, Hnf4a and Pax8—that, in certain combinations, convert embryonic and adult fibroblasts to induced renal tubular epithelial cells, which were termed iRECs. Reprogrammed iRECs resemble primary tubular cells in their mRNA-expression profile and show morphological and functional features of kidney tubule epithelia. They integrate into kidney organoids and form tubular structures in a decellularized kidney scaffold.

The present invention therefore relates to the following embodiments (1) to (33):

(1) A method for producing renal cells, comprising overexpressing Hnf1b and Pax8 in differentiated cells.

(2) The method of item (1), further comprising overexpressing Emx2 and/or Hnf4a in said differentiated cells.

(3) The method of item (1) or (2), comprising overexpressing Emx2, Hnf1b and Pax8 in said differentiated cells.

(4) The method of item (1) or (2), comprising overexpressing Hnf4a, Hnf1b and Pax8 in said differentiated cells.

(5) The method of any one of the preceding item, comprising overexpressing Emx2, Hnf4a, Hnf1b and Pax8 in said differentiated cells.

(6) The method of any one of items (1) to (5), wherein the renal cells are renal tubular cells.

(7) The method of any one of items (1) to (5), wherein the renal cells are renal tubular epithelial cells.

(8) The method of any one of the preceding items, wherein the differentiated cells are mammalian cells.

(9) The method of any one of the preceding items, wherein the differentiated cells are human cells.

(10) The method of any one of the preceding items, wherein the differentiated cells are fibroblasts.

(11) The method of item (10), wherein the fibroblasts are embryonic fibroblasts.

(12) The method of item (10), wherein the fibroblasts are adult fibroblasts.

(13) The method of any one of the preceding items, wherein the differentiated cells were obtained from a non-human animal having a modification of a gene associated with a disorder affecting the kidney.

(14) The method of item (13), wherein said disorder affecting the kidney is selected from the group consisting of conditions affecting the renal tubules, transport deficiencies such as Bartter syndrome, metabolic syndromes affecting renal tubules such as cytinosis, ciliopathies such as nephronophthisis, end stage renal disease, cystic kidney disease, polycystic kidney disease, CAKUT, renal cystic diseases, interstitial diseases, tumorous kidney diseases, renal tubular diseases, metabolic diseases, and nephrolithiasis.

(15) The method of item (13) or (14), wherein said gene is Pkd1 or Pkd2.

(16) The method of any one of items (13) to (15), wherein said modification is a constitutive or conditional knockout of said gene.

(17) The method of any one of the preceding items, wherein said overexpressing comprises (a) providing one or more nucleic acids encoding Hnf1b and Pax8 and optionally Emx2 and/or Hnf4a; (b) introducing said one or more nucleic acids into the differentiated cells so as to obtain transduced or transfected cells; and (c) culturing said transduced or transfected cells under conditions that allow overexpression of Hnf1b, and Pax8 and optionally of Emx2 and/or Hnf4a.

(18) The method of item (17), wherein said one or more nucleic acids are plasmids or vectors comprising a nucleotide sequence encoding Emx2, Hnf1b, Hnf4a, Pax8 or a combination thereof, operably linked to a promoter capable of inducing overexpression of the encoded genes.

(19) The method of any one of the preceding items, wherein said Emx2 comprises the nucleotide sequence as shown in SEQ ID NO:1 or a functional fragment thereof.
(20) The method of any one of the preceding items, wherein said Hnf1b comprises the nucleotide sequence as shown in SEQ ID NO:2 or a functional fragment thereof.
(21) The method of any one of the preceding items, wherein said Hnf4a comprises the nucleotide sequence as shown in SEQ ID NO:3 or a functional fragment thereof.
(22) The method of any one of the preceding items, wherein said Pax8 comprises the nucleotide sequence as shown in SEQ ID NO:4 or a functional fragment thereof.
(23) The method of any one of the preceding items, further comprising modifying in said differentiated cells or in said renal cells at least one gene associated with a disorder affecting the kidney.
(24) The method of item (23), wherein said modifying comprises disrupting said gene associated with a disorder affecting the kidney.
(25) The method of item (23) or (24), wherein said disorder affecting the kidney is selected from the group consisting of conditions affecting the renal tubules, transport deficiencies such as Bartter syndrome, metabolic syndromes affecting renal tubules such as cytinosis, ciliopathies such as nephronophthisis, end stage renal disease, cystic kidney disease, polycystic kidney disease, CAKUT, Renal cystic diseases, interstitial diseases, tumorous kidney diseases, renal tubular diseases, metabolic diseases, and nephrolithiasis.
(26) The method of any one of items (23) to (25), wherein said gene is Pkd1 or Pkd2.
(27) A renal cell obtainable by the method of any one of the preceding items.
(28) The renal cell of item (27), having a modification in at least one gene associated with a disorder affecting the kidney.
(29) The renal cell of item (28), wherein said modification is a constitutive or conditional knockout of said gene.
(30) The renal cell of item (28) or (29), wherein said disorder affecting the kidney is selected from the group consisting of conditions affecting the renal tubules, transport deficiencies such as Bartter syndrome, metabolic syndromes affecting renal tubules such as cytinosis, ciliopathies such as nephronophthisis, end stage renal disease, cystic kidney disease, polycystic kidney disease, CAKUT, renal cystic diseases, interstitial diseases, tumorous kidney diseases, renal tubular diseases, metabolic diseases, and nephrolithiasis.
(31) The renal cell of any one of items (28) to (30), wherein said gene is Pkd1 or Pkd2.
(32) The use of the renal cell of any one of items (27) to (31) for nephrotoxicity testing, pharmacological screening or disease modeling.
(33) The use of item (32), wherein said disease modeling comprises modeling a disorder affecting the kidney, selected from the group consisting of conditions affecting the renal tubules, transport deficiencies such as Bartter syndrome, metabolic syndromes affecting renal tubules such as cytinosis, ciliopathies such as nephronophthisis, end stage renal disease, cystic kidney disease, polycystic kidney disease, CAKUT, renal cystic diseases, interstitial diseases, tumorous kidney diseases, renal tubular diseases, metabolic diseases, and nephrolithiasis.

Error bars: SEM, Significant differences were assessed by Student's unpaired t-test, n=3, * p<0.001,  p<0.01, * p<0.05. Scale bars, 50 µm (a,e), 1 cm (b), 100 µm (c).

Figure 4:
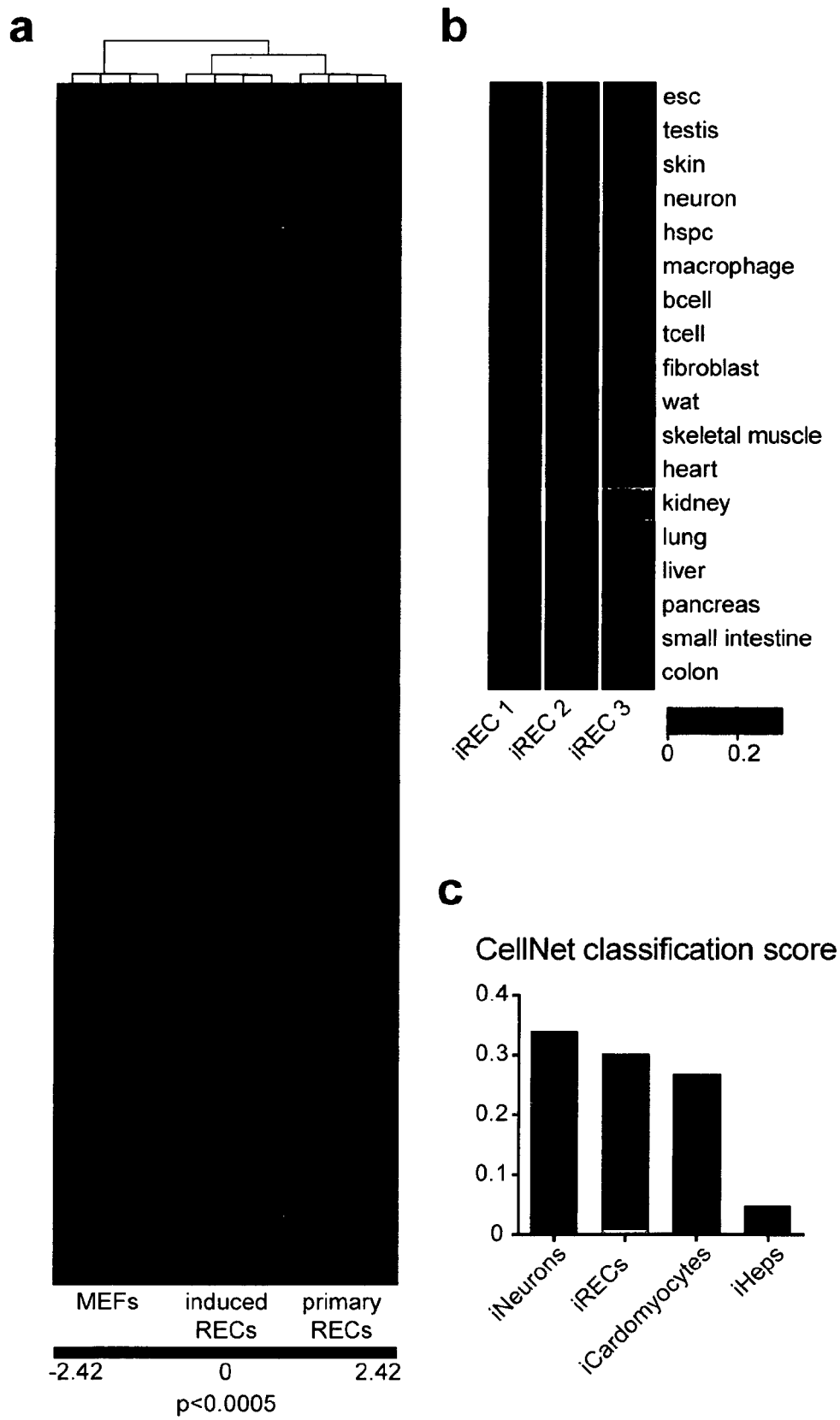
Figure 4:
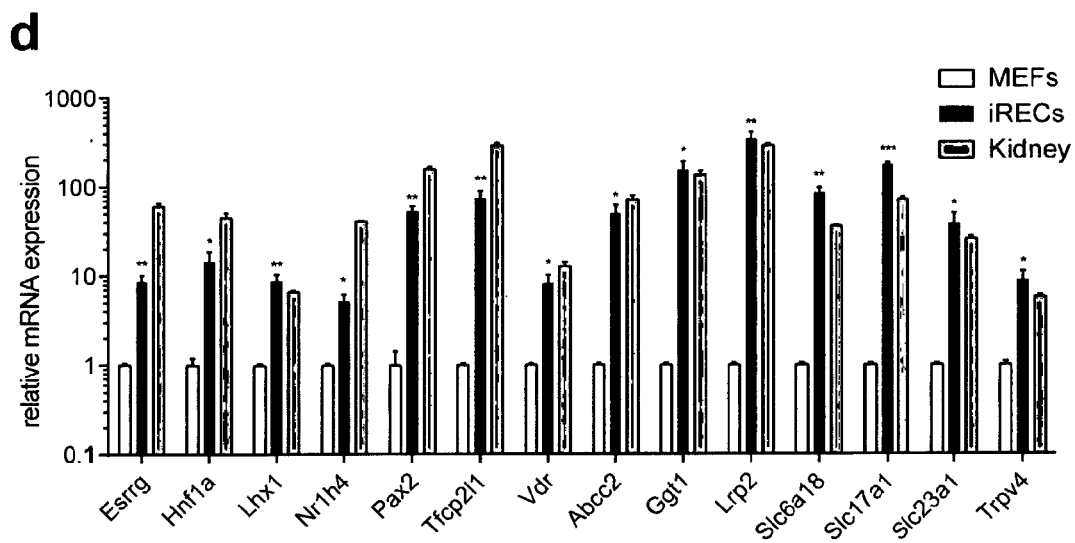
Figure 4:
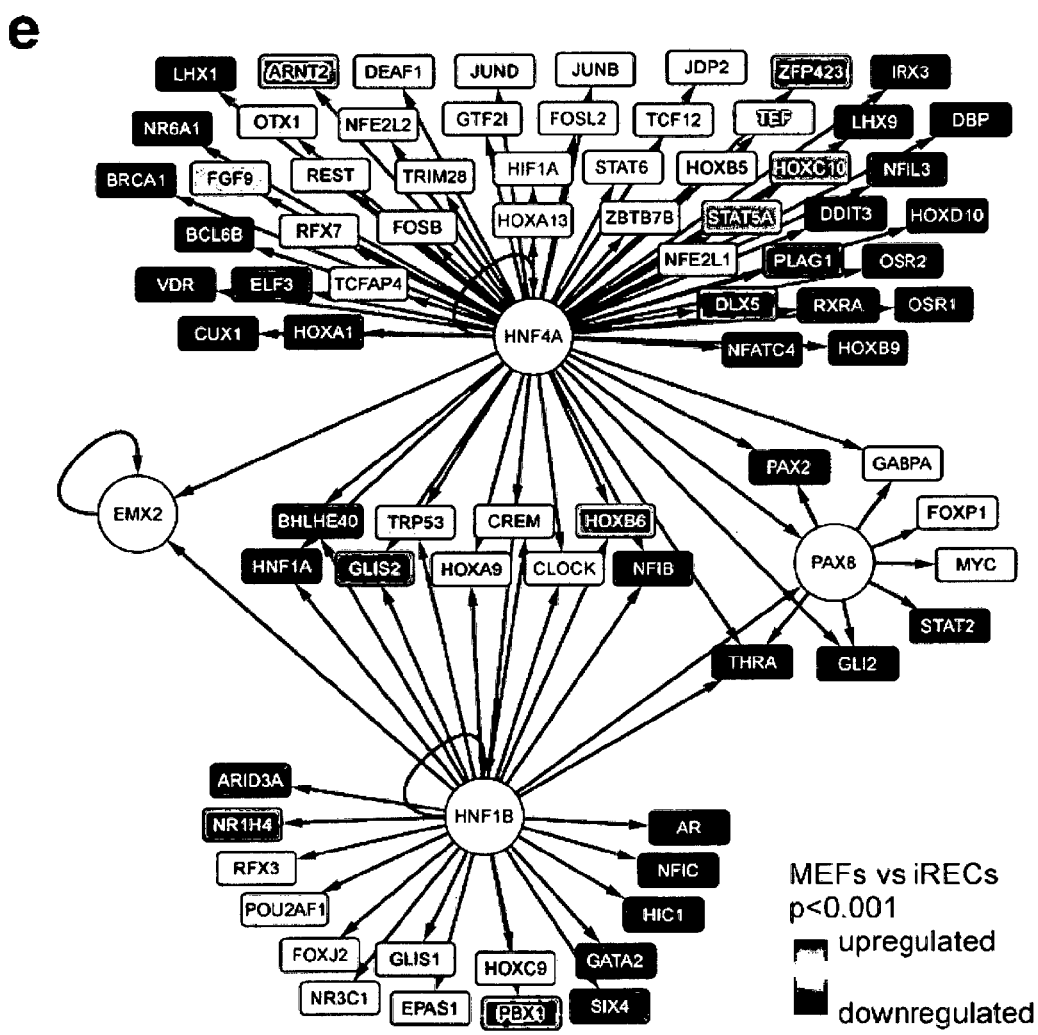
Figure 4:
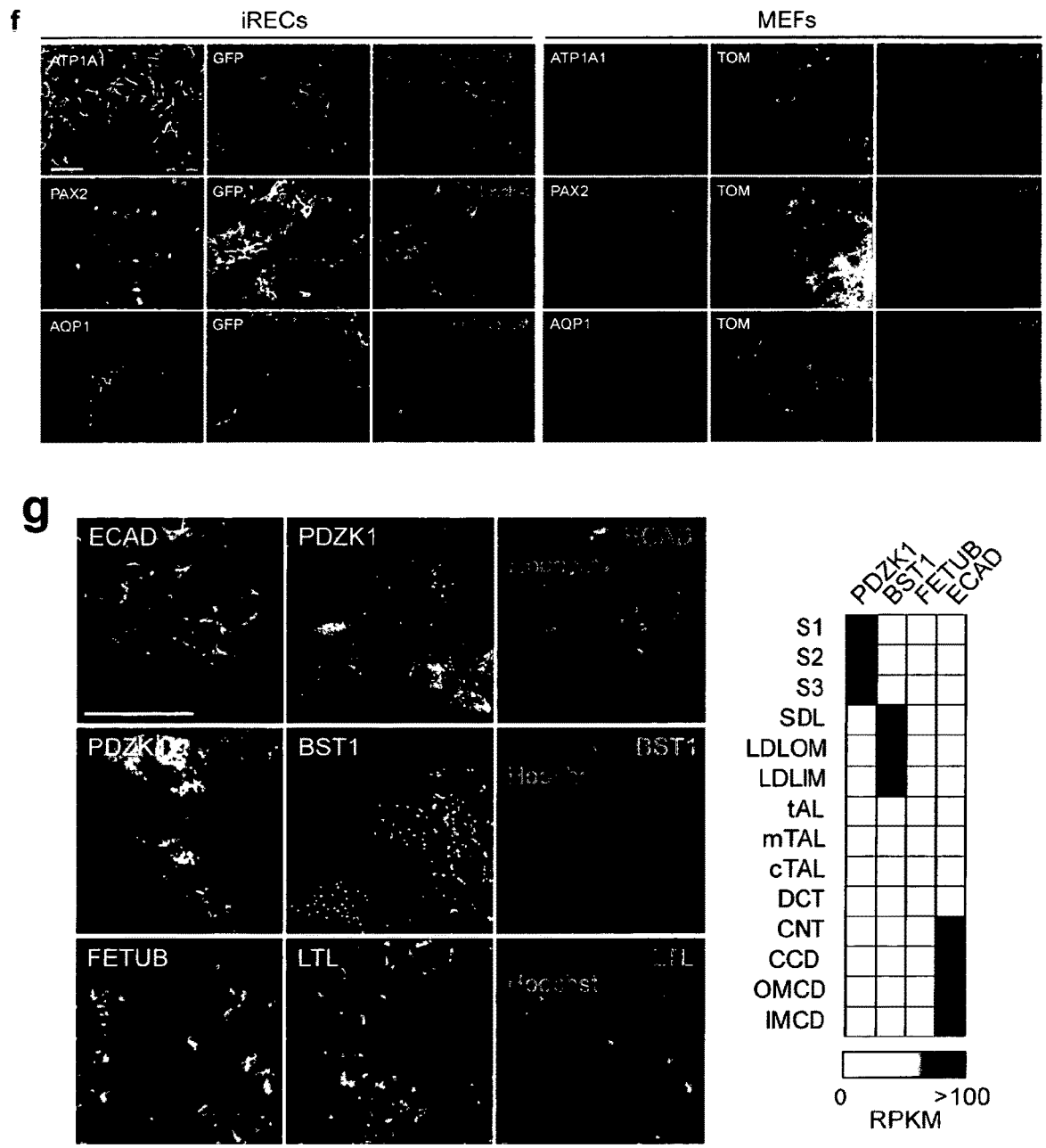
Figure 4:
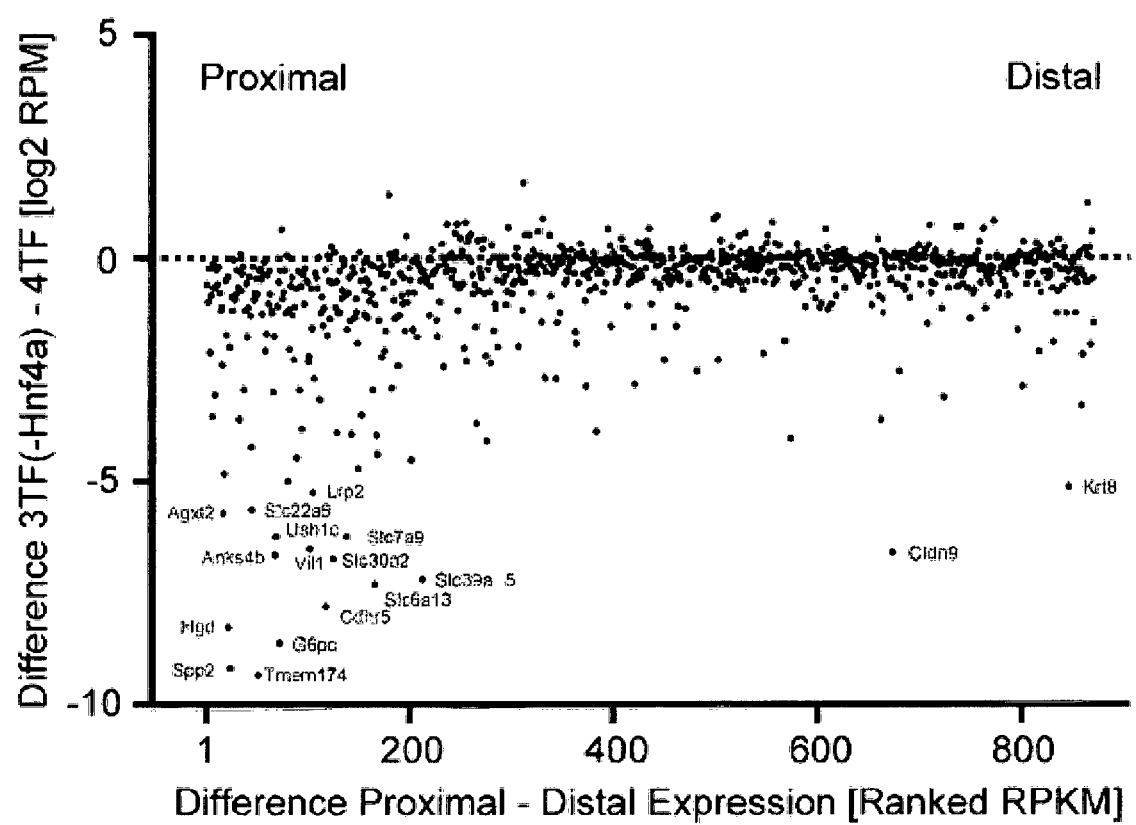

FIG. 4: iRECs resemble primary renal epithelial cells in their global gene expression pattern.
(a) Hierarchical clustering and heatmap image of cDNA microarray data comparing gene expression profiles of MEFs, iRECs and reporter positive primary RECs isolated by cell sorting for GFP from Ksp-Cre; mTOM/mGFP kidneys (n=4 for each group). Blue indicates downregulation, red indicates upregulation. Clustering was performed for 1.5-fold up/downregulated genes of iRECs vs. MEFs (p<0.0005). (b) CellNet-generated heatmap with each row representing the indicated cell type or tissue and each column representing one of three independently reprogrammed iREC cultures. Values representing the classification score are color-coded (black to green). (c) Classification scores of previously published directly reprogrammed cell types and iRECs as determined by CellNet[34]. (d) Relative mRNA expression levels of renal marker genes in MEFs, iRECs, and whole kidney lysates as determined by qRT-PCR. Significant differences were assessed by Student's unpaired t-test, n=3, * p<0.001,  p<0.01, * p<0.05; Error bars: SEM. (e) Transcriptional circuitry network of predicted target genes of iREC reprogramming factors (yellow circles). Blue indicates down-regulation, red indicates upregulation. (f) Immunofluorescence staining of the indicated renal tubular proteins in iRECs and MEFs. (g) Immunostaining of iRECs for proteins with nephron segment restricted expression (left panel) and table illustrating the expression pattern along the different nephron segments (right panel)[39]; S1, first segment of the proximal tubule; S2, second segment of the proximal tubule; S3, third segment of the proximal tubule; SDL, short descending limb of the loop of Henle; LDLOM, long descending limb of the loop of Henle in the outer medulla; LDLIM, long descending limb of the loop of Henle in the inner medulla; tAL, thin ascending limb of the loop of Henle; mTAL, medullary thick ascending limb of the loop of Henle; cTAL, cortical thick ascending limb of the loop of Henle; DCT, distal convoluted tubule; CNT, connecting tubule; CCD, cortical collecting duct; OMCD, outer medullary collecting duct; IMCD, inner medullary collecting duct. (h) RNA-Seq expression analysis of differentially upregulated genes (0TF vs. 4TF, unsorted) after omission of Hnf4a from the 4TF reprogramming cocktail. X axis: genes ranked according to their proximal to distal expression pattern. Y axis: Difference in $\log_2$ RPM expression of 3TF (minus Hnf4a) to 4TF treated cells. Scale bars, 50 µm (f,g).

Figure 5:
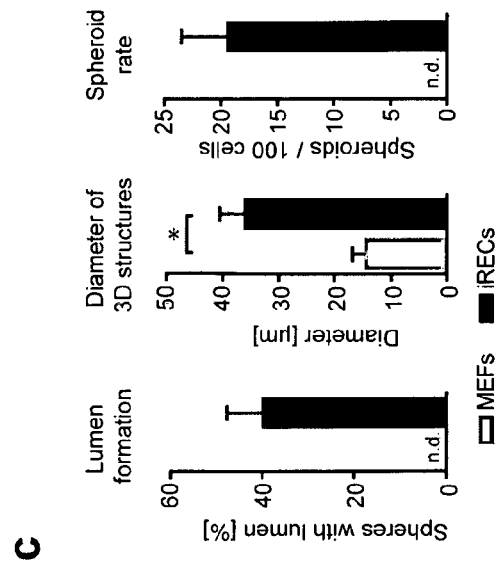
Figure 5:
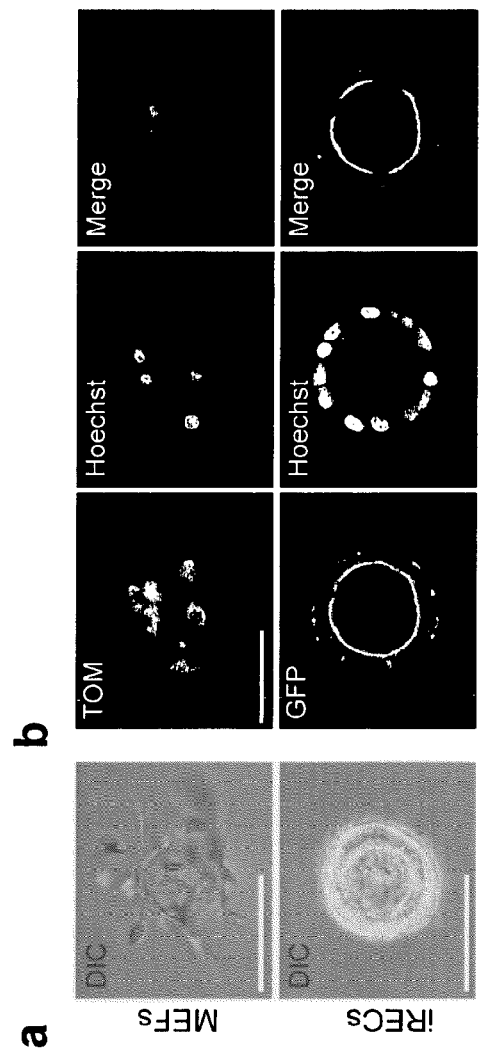
Figure 5:
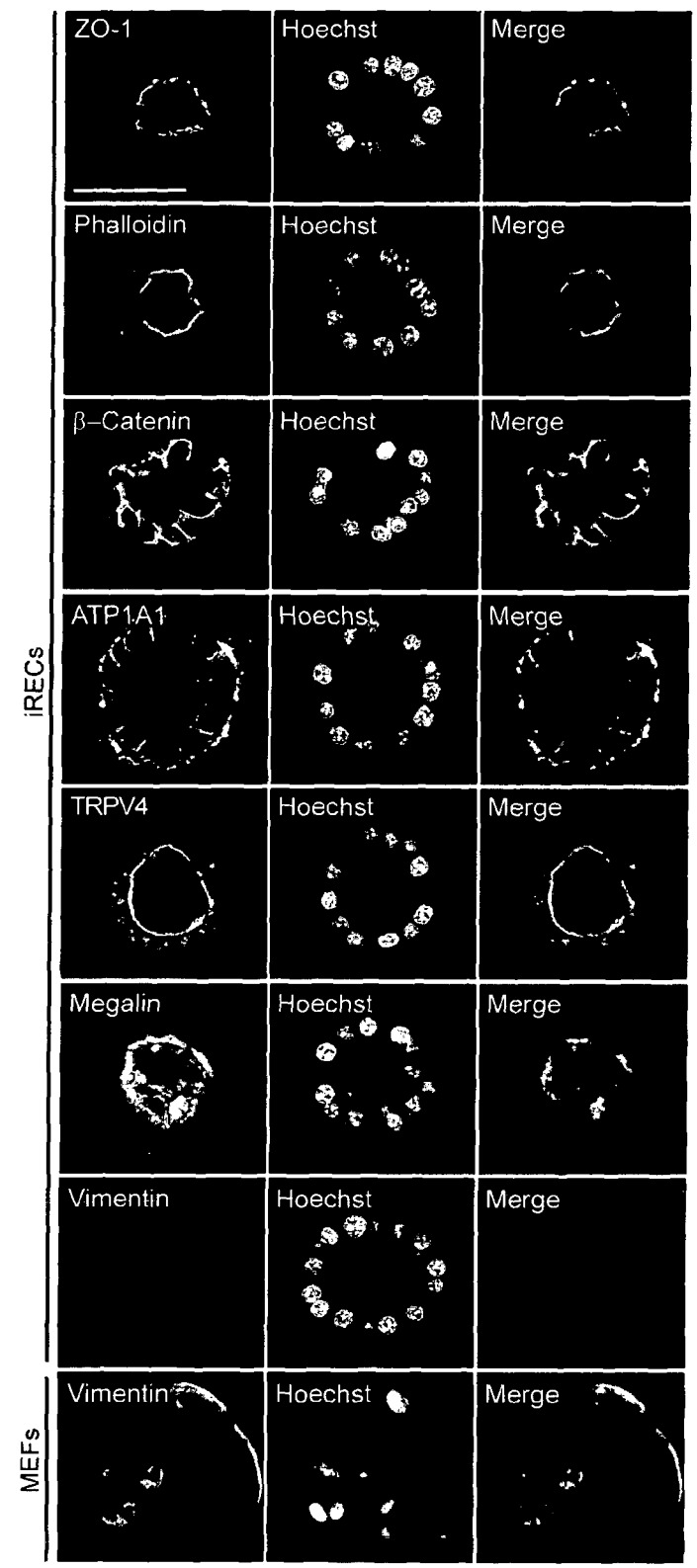
Figure 5:
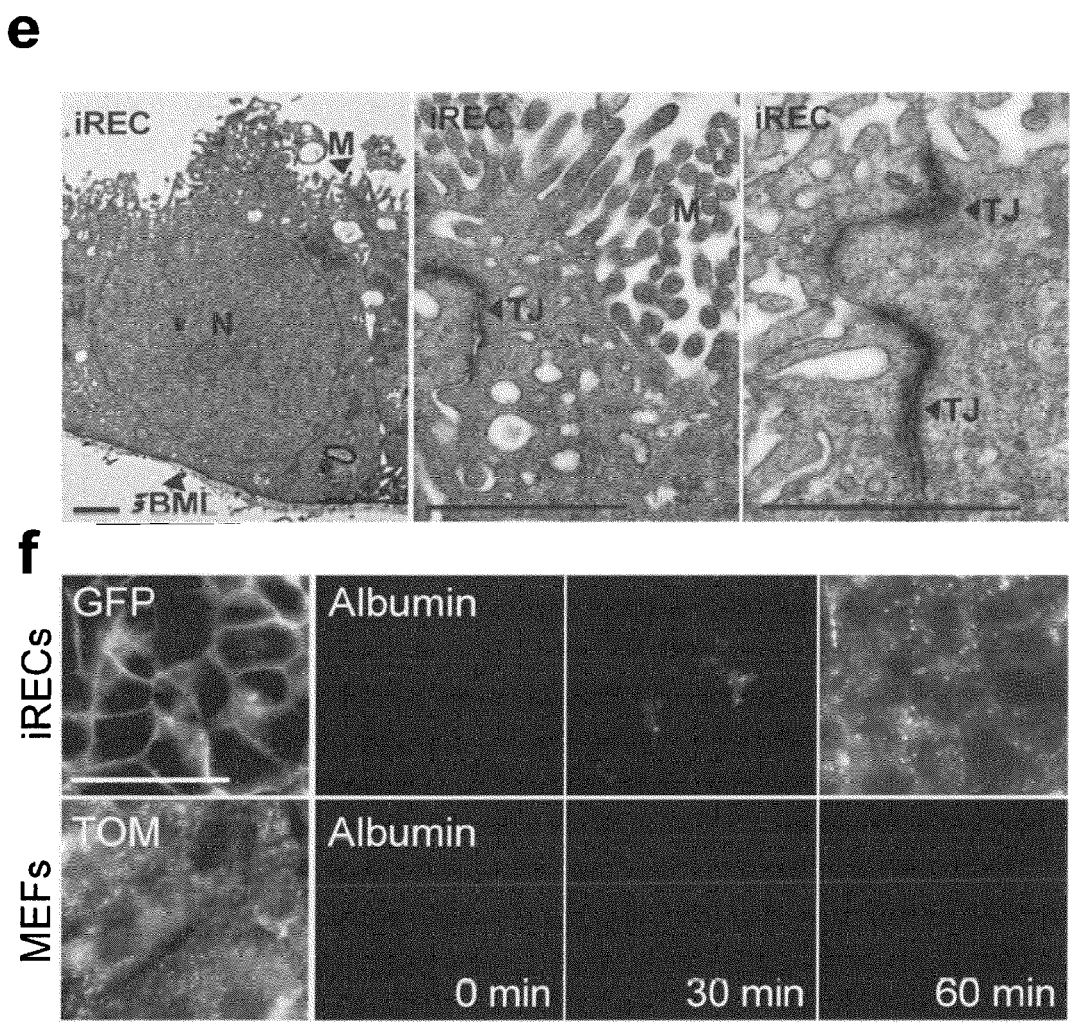
Figure 5:
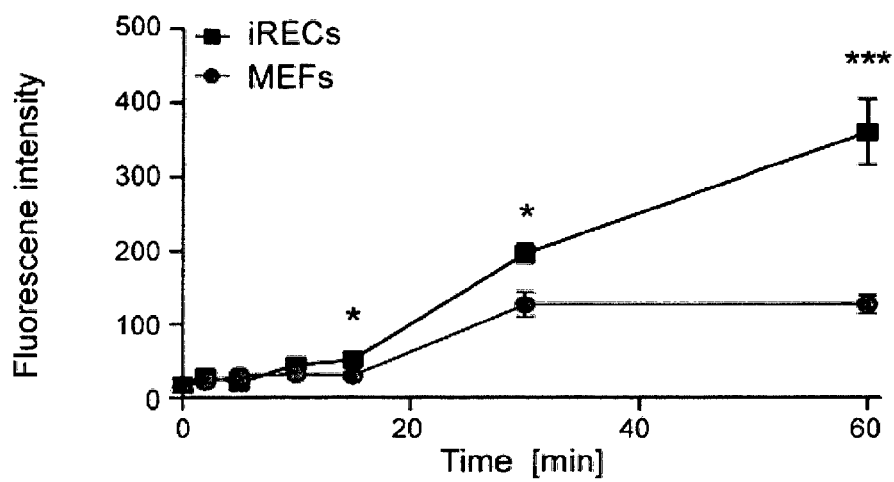
Figure 5:
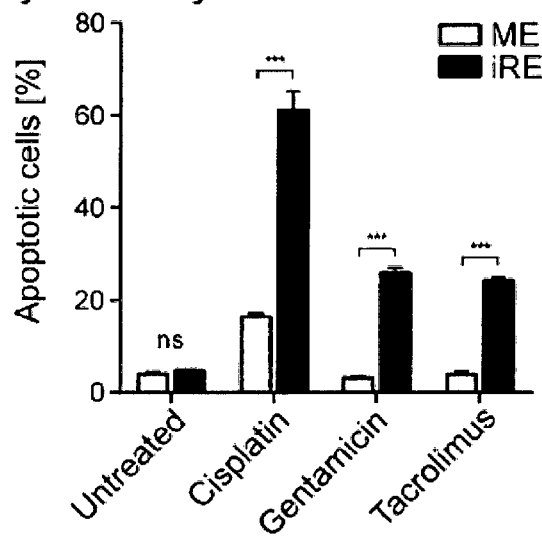
Figure 5:
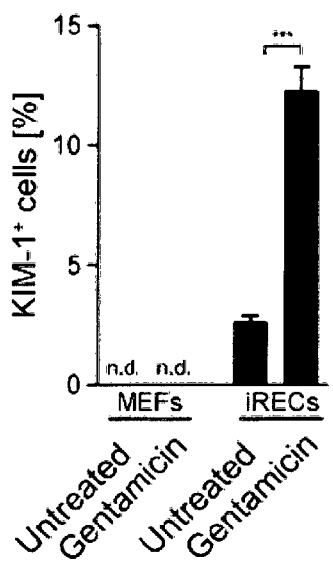
Figure 5:
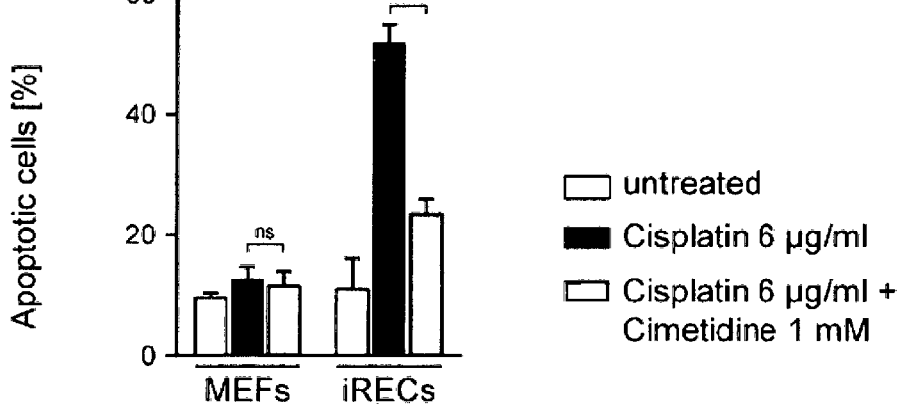

FIG. 5: iRECs show functional properties of renal tubular epithelial cells.
(a) Differential interference contrast (DIC) images of MEFs and iRECs grown in 3D Matrigel. (b) Confocal live-cell imaging of tomato red (TOM) expressing MEFs and GFP expressing iRECs grown in 3D Matrigel. Nuclei stained with Hoechst. (c) Quantification of lumen formation (%), maximum diameter (µm) of 3D structures and number of spheroids per 100 cells seeded; n.d.=not detectable. (d) Immunostaining of the indicated proteins in iRECs and MEFs grown in 3D Matrigel. Nuclei were stained with Hoechst. Representative confocal images show planes of maximum diameter of the spheres. (e) Transmission electron microscopy images of iRECs grown in 3D Matrigel. TJ: tight junction; M: microvilli; BML: basement membrane like matrix; N: nucleus. (f) Representative images of MEFs and iRECs incubated with alexa-647 labeled albumin for the indicated time-periods. (g) Quantification of albumin uptake in MEFs and iRECs over a 60 min time course. (h) Quantification of apoptotic cells (%) in cisplatin (6 µg/ml), gentamicin (1 mg/ml), or tacrolimus (40 µM) treated MEFs and iRECs or untreated controls. (i) Analysis of KIM-1$^+$ MEFs and iRECs by flow cytometry after treatment with gentamicin (1 mg/ml). (j) Percentage of apoptotic cells in untreated, cisplatin only treated or cisplatin and cimetidine treated MEFs and iRECs. Error bars: SEM, Student's unpaired t-test, n=3, * p<0.001,  p<0.01, * p<0.05; Scale bars, 50 µm (a,b,d,f), 500 nm (e).

Figure 6:
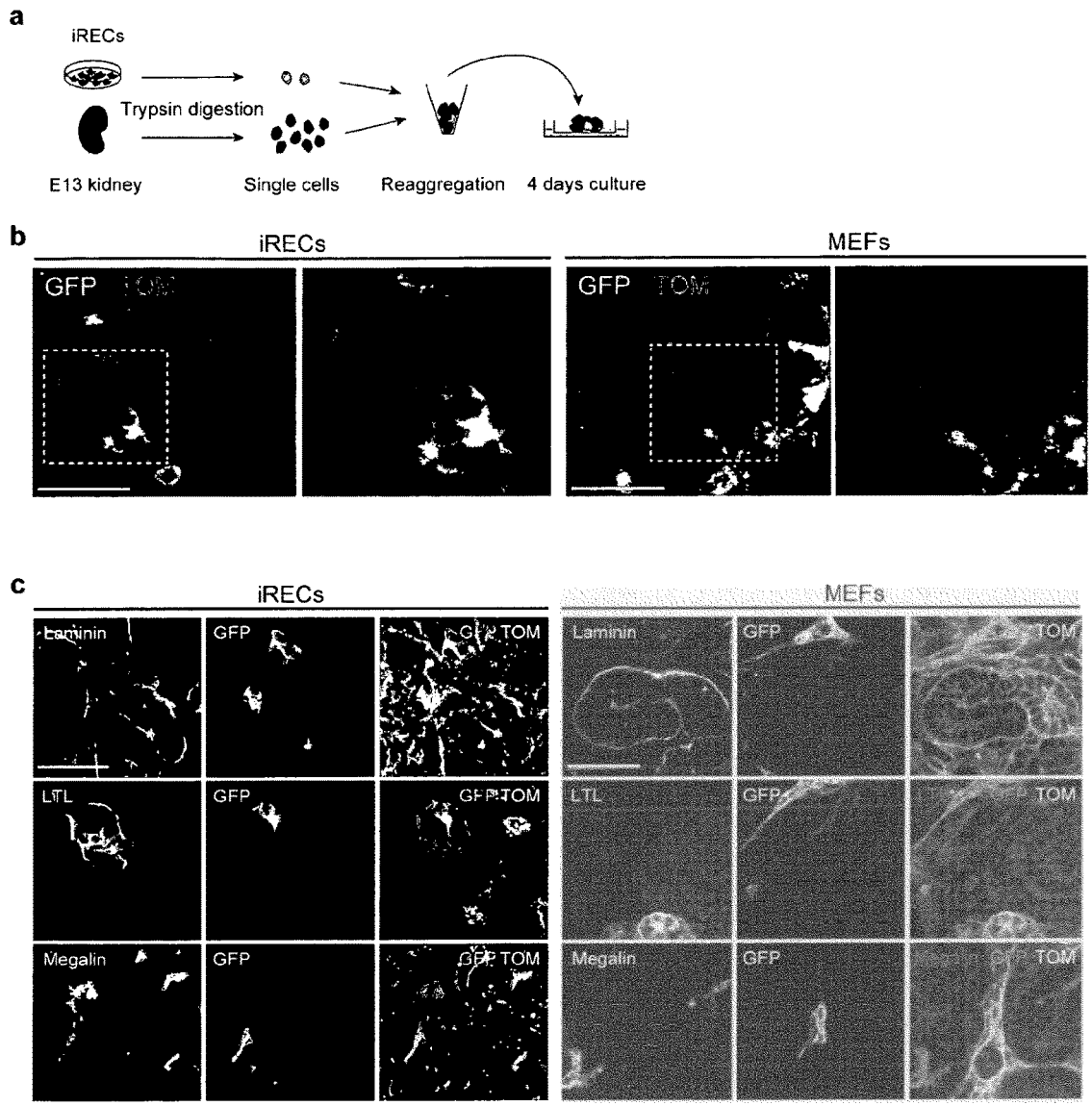
Figure 6:
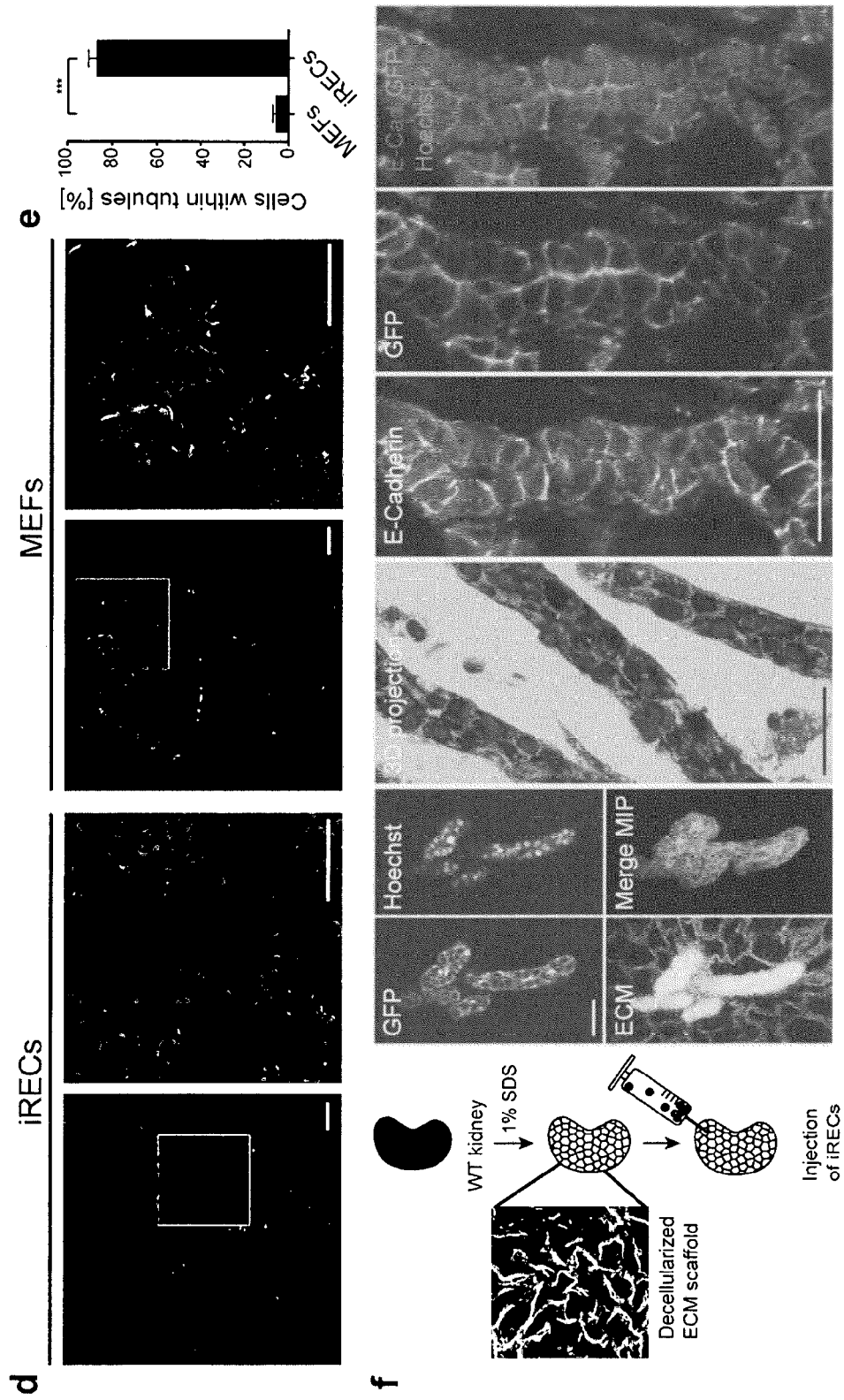

FIG. 6: iRECs integrate into reaggregated renal organoids and repopulate decellularized kidneys.
(a) Schematic illustration of the reaggregation assay. GFP$^+$ iRECs and E13 TOM$^+$ kidneys were trypsin digested, mixed in a 1:10 ratio and grown on an air-liquid interface culture. (b) Confocal live-imaging of renal organoids reaggregated with either KSP-Cre GFP$^+$ iRECs or GFP transduced control MEFs. The white boxed area is shown enlarged in the right panel. (c) Immunostaining of kidney organoids reaggreagated with MEFs or iRECs for the indicated proteins. (d) Tile scanned confocal images of entire reaggregates after staining for Laminin and enlargement of the white boxed area. (e) Quantification of GFP$^+$ iRECs and MEFs detected inside or outside the Laminin stained basement membrane of reaggregated tubules. Error bars: SEM, Student's unpaired t-test, n=3, *** p<0.001 (f) Schematic illustration of the repopulation assay. Wild type kidneys were decellularized with 1% SDS and injected with iRECs; confocal images and 3D reconstructions of deceullarized kidneys repopulated with KSP-Cre GFP$^+$ iRECs and immunostained for E-cadherin. Nuclei were stained with Hoechst. ECM: extra cellular matrix, MIP: Maximum intensity projection of confocal z-stacks. Scale bars, 50 µm (b,c,f), 200 µm (d).

Figure 7:
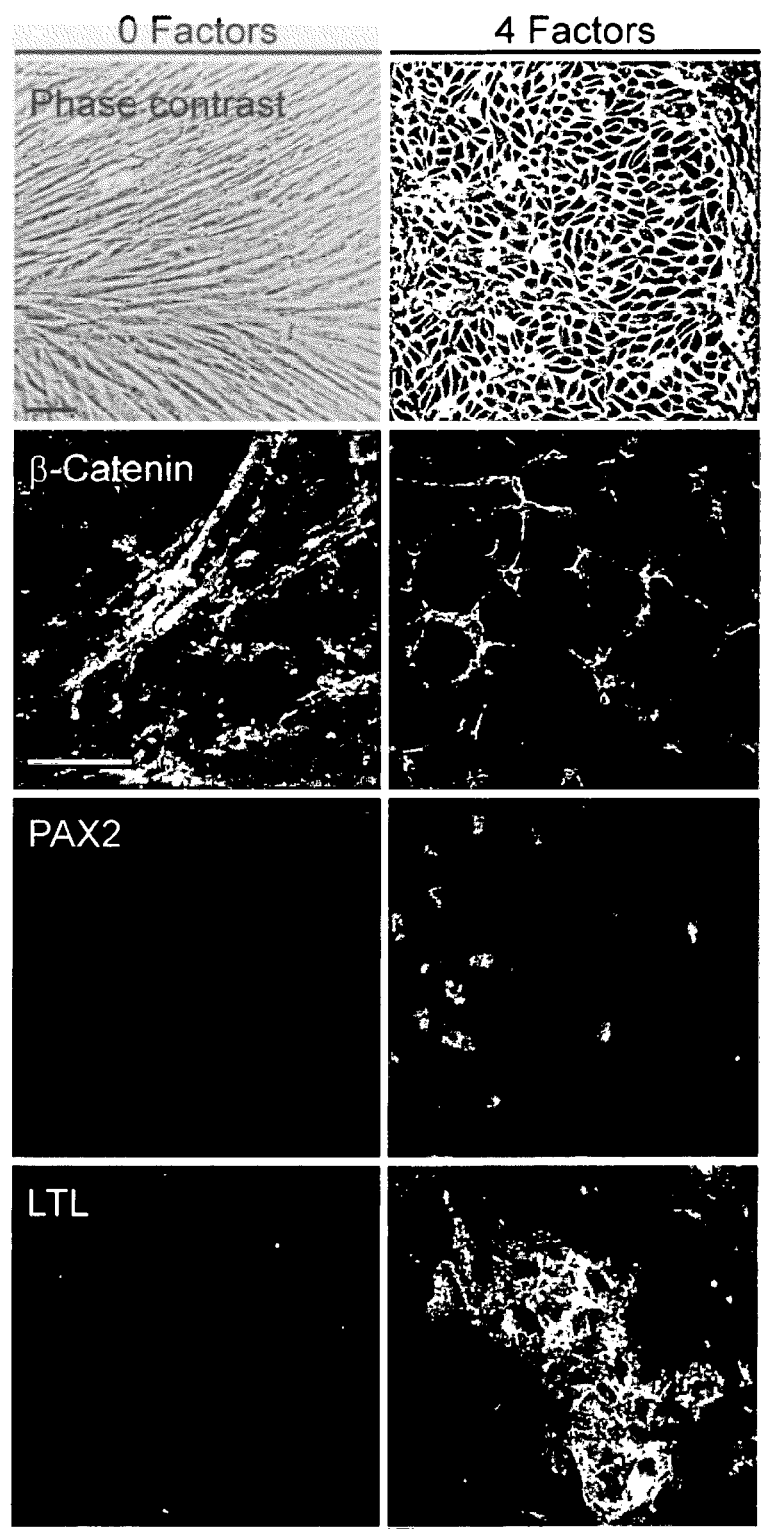
Figure 7:
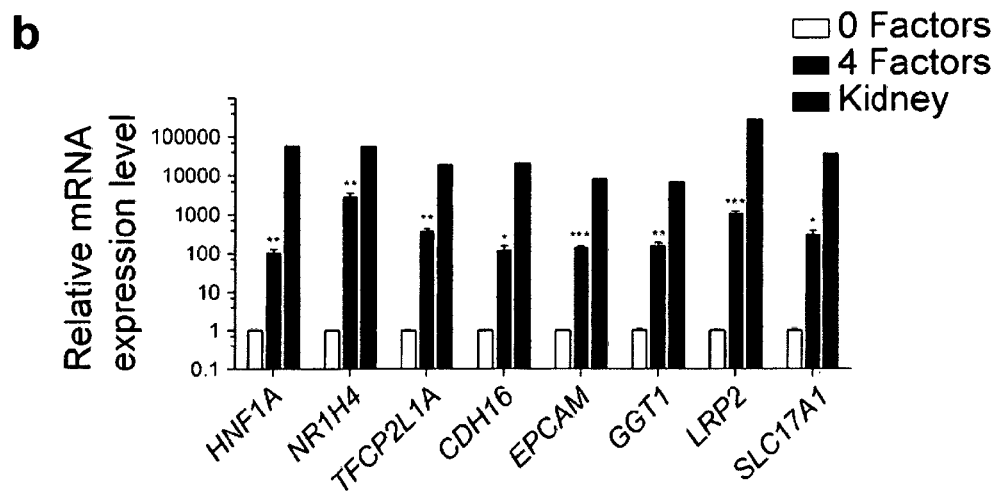
Figure 7:
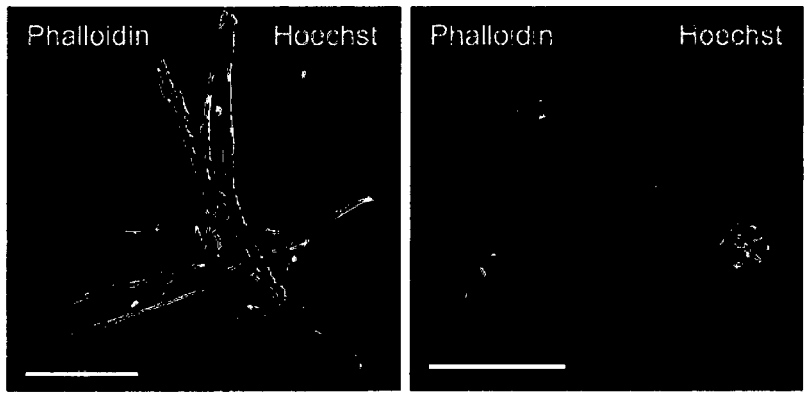
Figure 7:
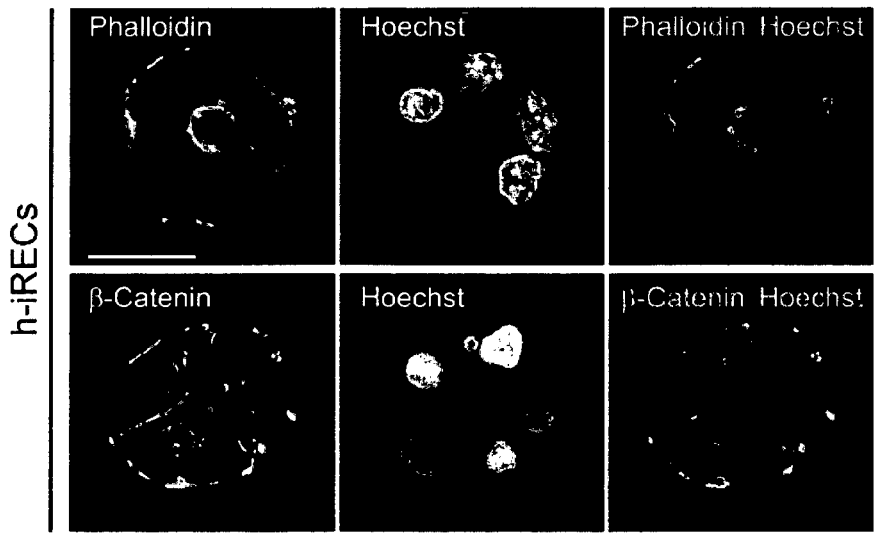
Figure 7:
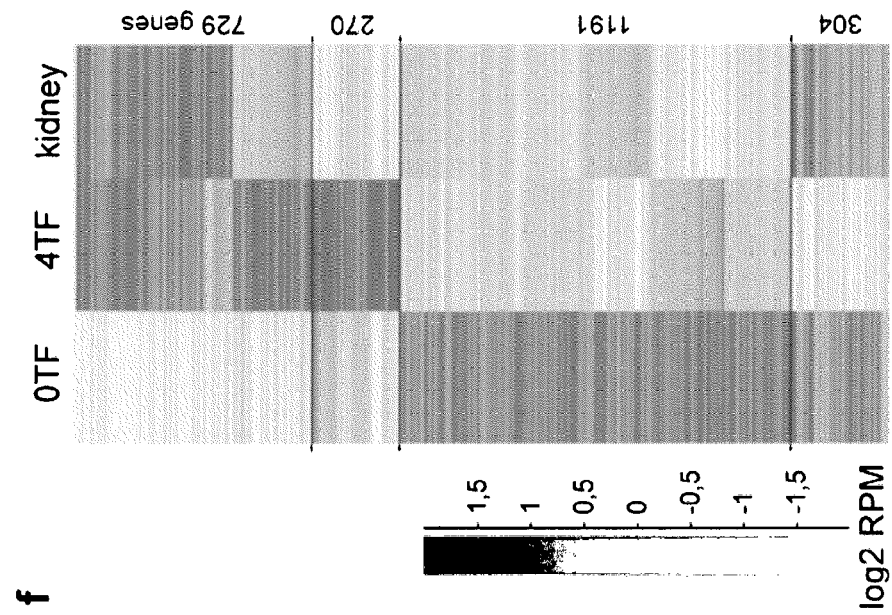
Figure 7:
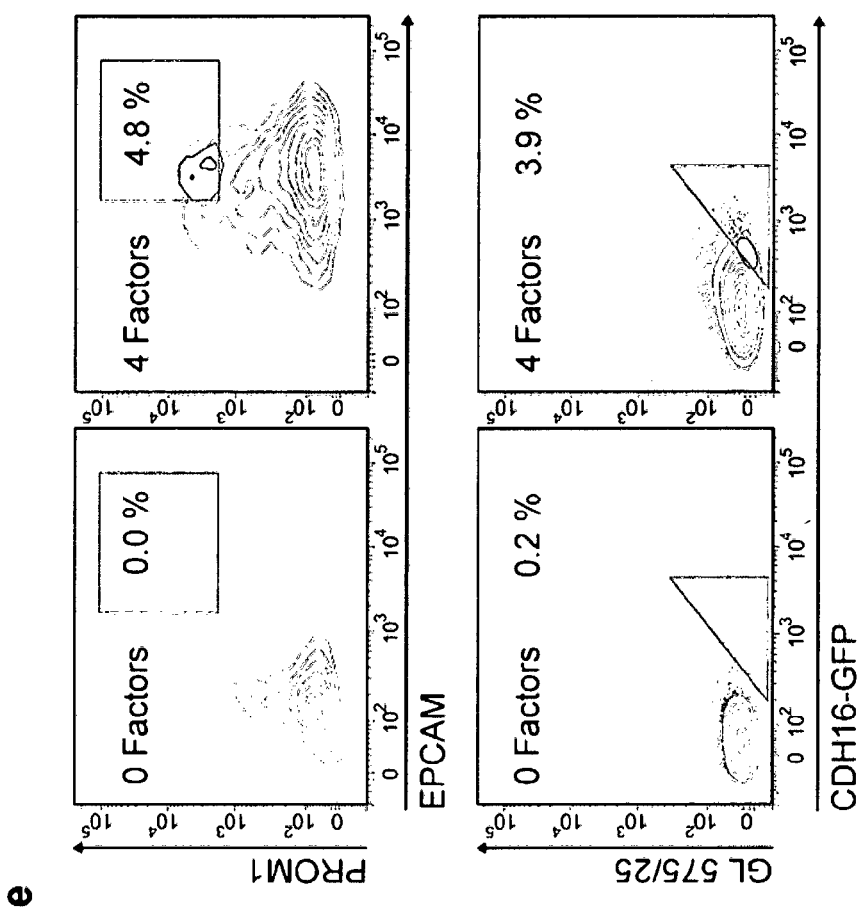

FIG. 7: Reprogramming of human fibroblasts.
(a) Phase contrast image and immunostaining for the indicated proteins in untreated and 4TF treated human fibroblasts. (b) Relative mRNA expression level of the indicated genes as determined by qRT-PCR. Significant differences were assessed by Student's unpaired t-test, n=3, * p<0.001,  p<0.01, * p<0.05; Error bars: SEM. (c) Untreated human fibroblasts and human induced renal epithelial cells (h-iRECs) cultured in 3D Matrigel. Shown are maximum intensity projections of confocal z-Stacks. (d) Matrigel grown h-iREC spheres stained for actin (phalloidin) and β-Catenin. (e) Percentage of PROM1$^+$/EPCAM$^+$ double positive human fibroblasts after treatment with 4TF and SV40 or SV40 alone (top panel) and percentage of CDH16-GFP$^+$ cells (bottom panel) as determined by flow cytometry. (f) Heatmap of RNA-Seq expression analysis in human fibroblast (0TF), CH16-GFP$^+$ sorted h-iRECs (4TF) and human kidney. Differentially regulated genes (0TF vs. 4TFs, p<0.0001) were hierarchically clustered. The number of genes in each cluster is shown on the right (Pearson's correlation coefficient 0.7). Scale bars, 50 µm (a), 100 µm (c), 20 µm (d).

Figure 8:
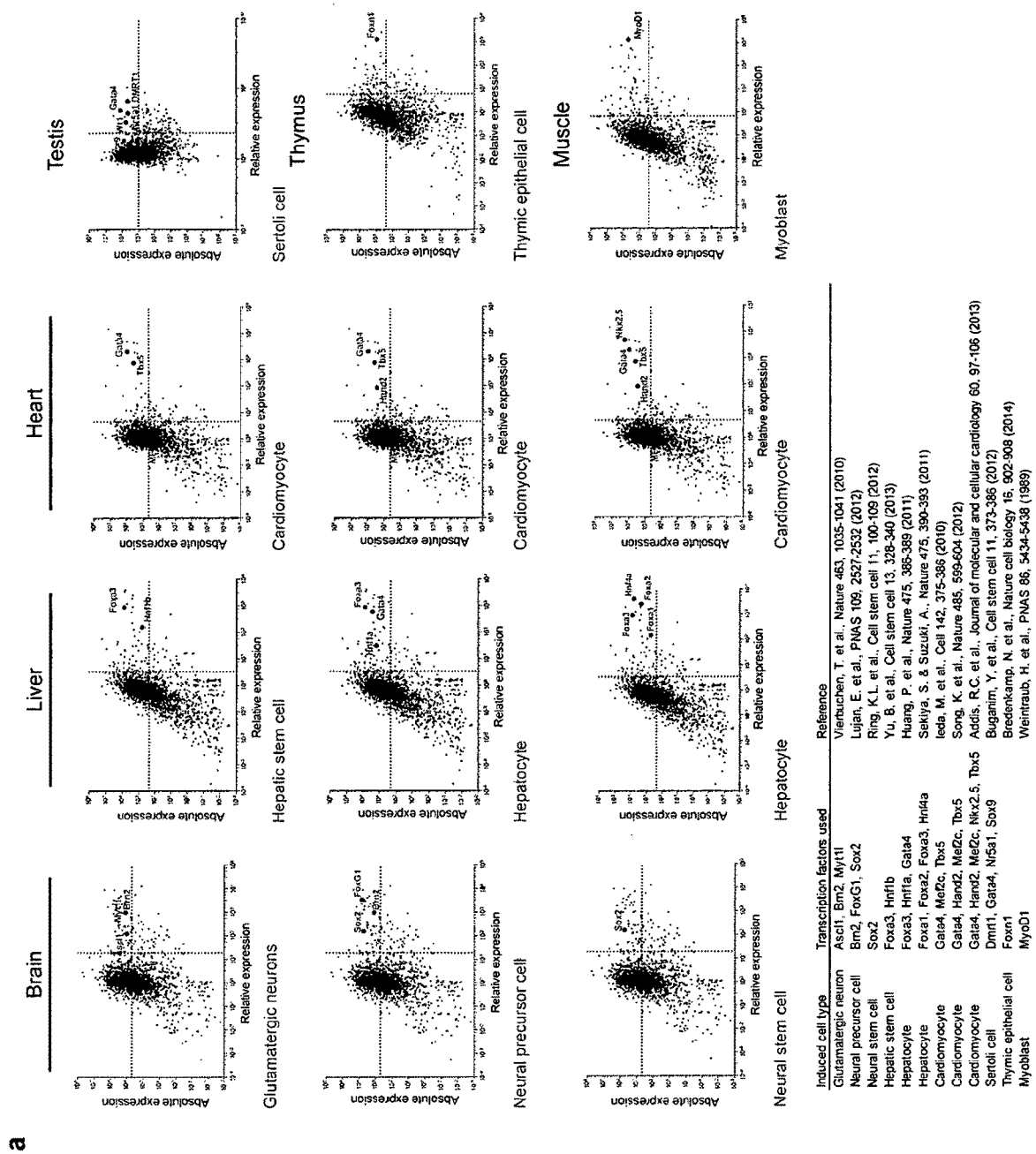
Figure 8:
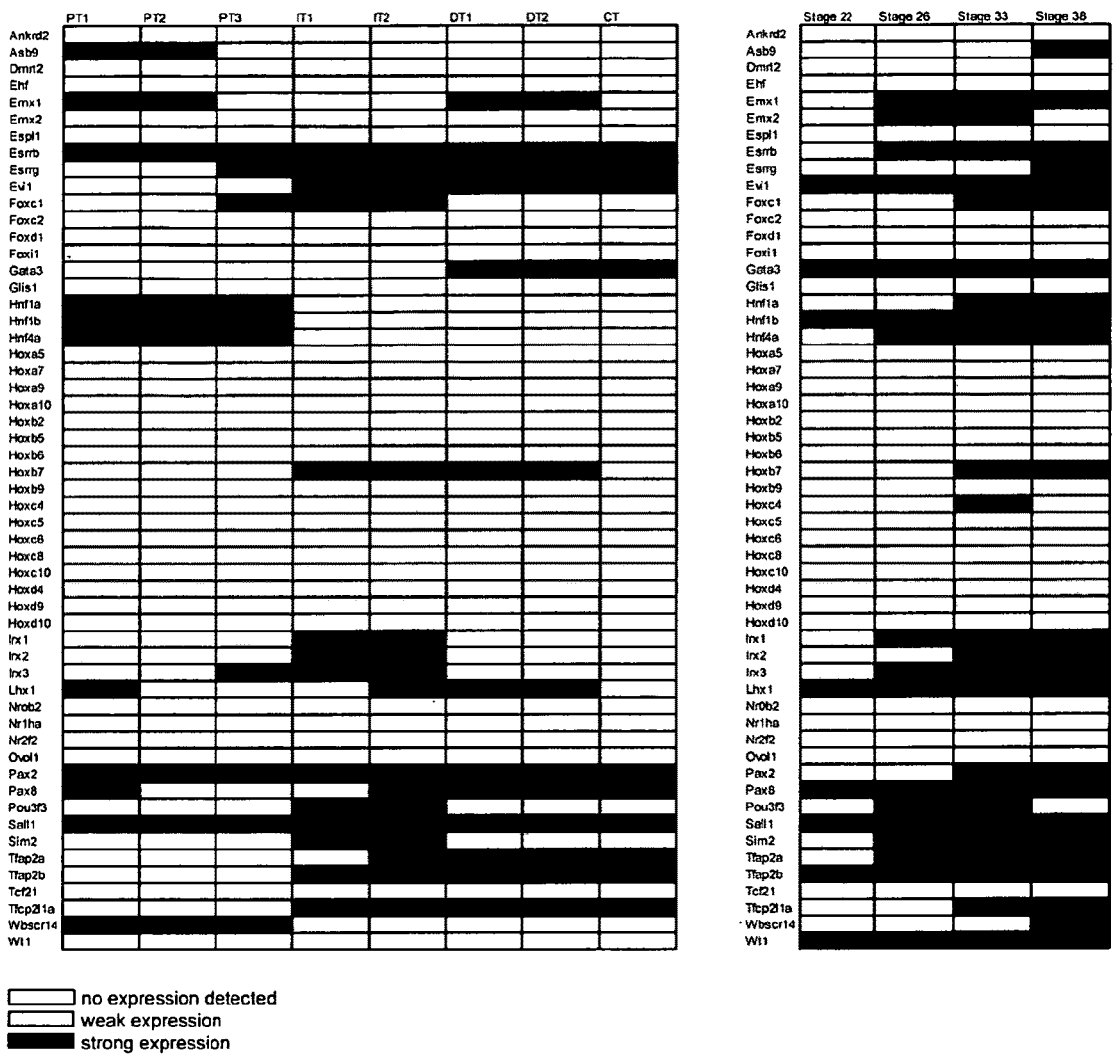

FIG. 8: Distribution of known reprogramming factors in quantitative expression data.
(a) Scatter-plots depicting the absolute and relative expression levels of transcription factors (TFs) in brain, liver, heart, testis, thymus and muscle tissue. TFs successfully used for reprogramming into the indicated cell type (blue) are highlighted in red. Dashed lines indicate the level of the 50$^{th}$ percentile of absolute expression and the 95$^{th}$ percentile of relative expression. Combinations of TFs are according to the studies referenced below.
(b) Summary of Xenopus whole mount in situ hybridization experiments: Spatial expression pattern at stage 38. White, grey and black colored boxes indicate undetectable, weak and strong gene expression within the different segments of the *Xenopus* pronephros. PT1, PT2, PT3: proximal tubule segment 1, 2 and 3. IT1, IT2: intermediate tubule segment 1 and 2. DT1, DT2: distal tubule segment 1 and 2. CT: connecting tubule (left panel). Temporal expression pattern at stages 22, 26, 33 and 38 of *Xenopus* development (right panel). (c) Summary of transcription factor expression in E12-E17 mouse embryonic kidney. E12-E17 embryonic kidneys were serially sectioned and analyzed by in situ hybridization for indicated genes. Spatial expression patterns were determined within the kidney anlagen and sections analyzed for expression within the ureteric bud (ub) and metanephric mesenchyme (mm) at E12, and nephrogenic mesenchyme (nm), stroma/interstitium (str), renal vesicle/glomerulus (rv/g) and tubular epithelium (te) from E13 to E17.

Figure 9:

FIG. 9: Whole mount in situ hybridization of candidate reprogramming factors in *Xenopus* embryos.

Whole mount in situ hybridization (WISH) of the indicated genes. WISH was performed on *Xenopus* embryos at stages 22, 26, 33, and 38. Enlarged views show the pronephric region. Scale bars, 500 µm.

Figure 10:
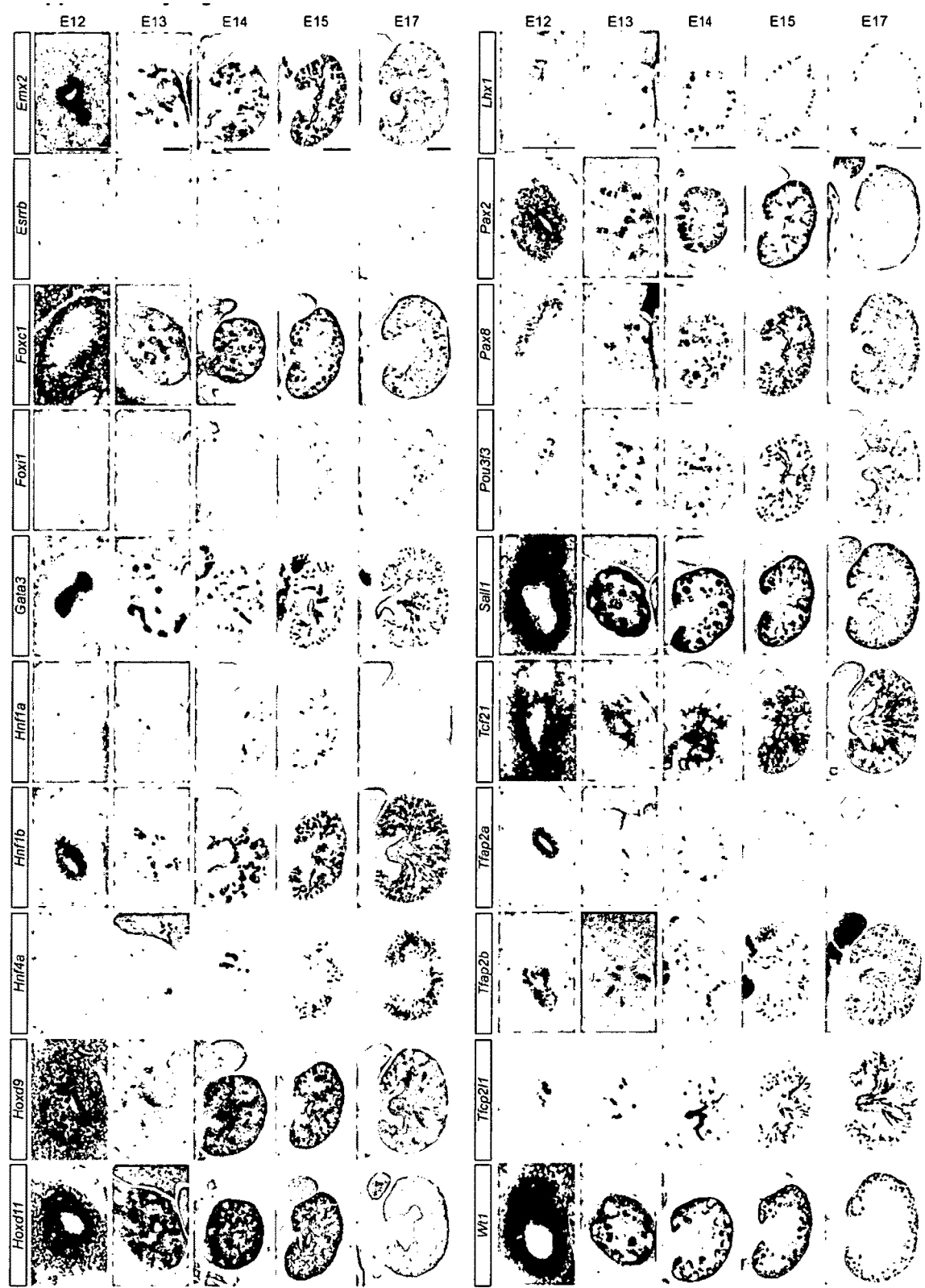

FIG. 10: Expression of candidate reprogramming transcription factors during kidney development in mouse.

mRNA expression of the indicated 20 transcription factors was visualized by in situ hybridization on paraffin sections of mouse nephrogenic anlagen and embryonic kidneys from E12 to E17 on consecutive sections from the same embryos ensuring increased comparability between expression of different transcription factors. Scale bars, 200 µm (E12, E13), 500 µm (E14-E17).

Figure 11:
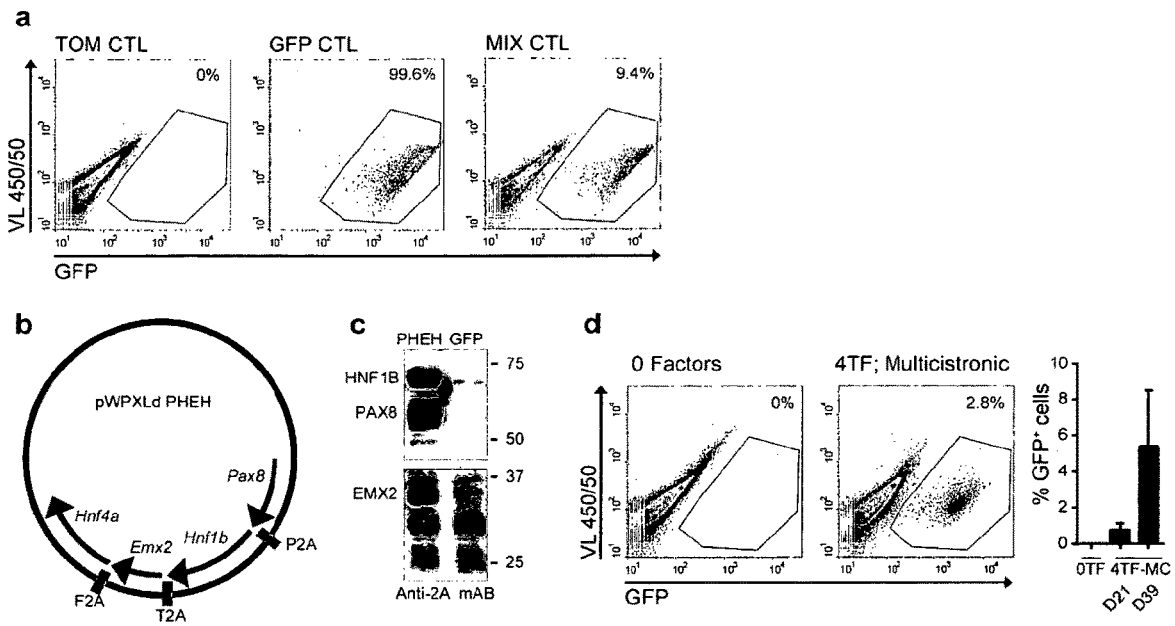
Figure 11:
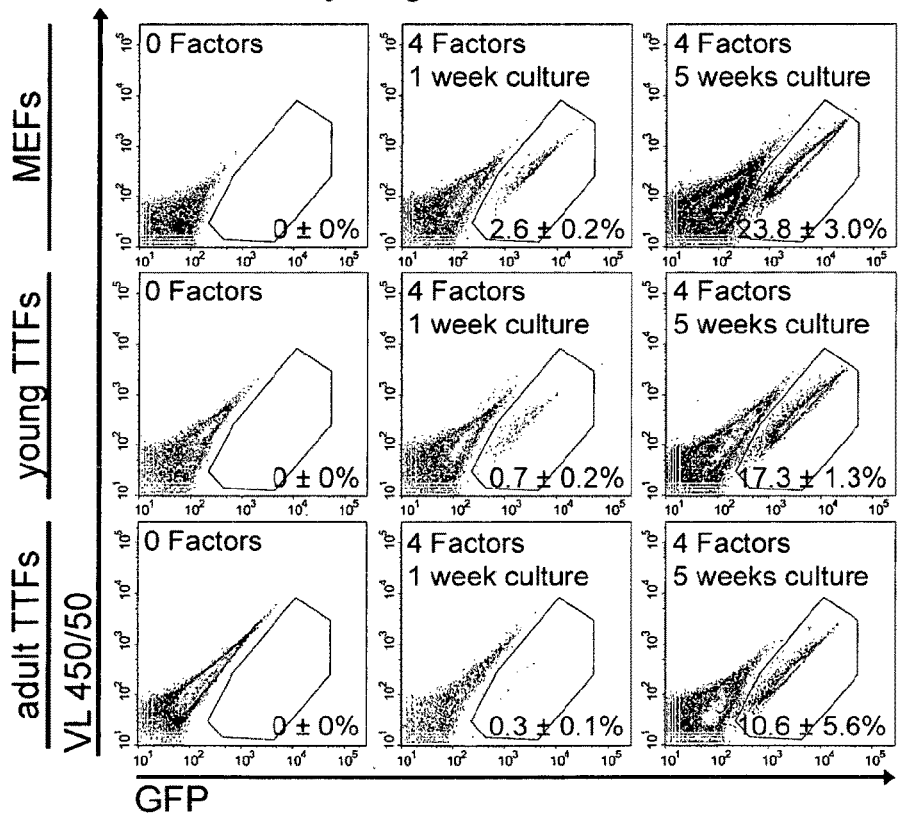
Figure 11:
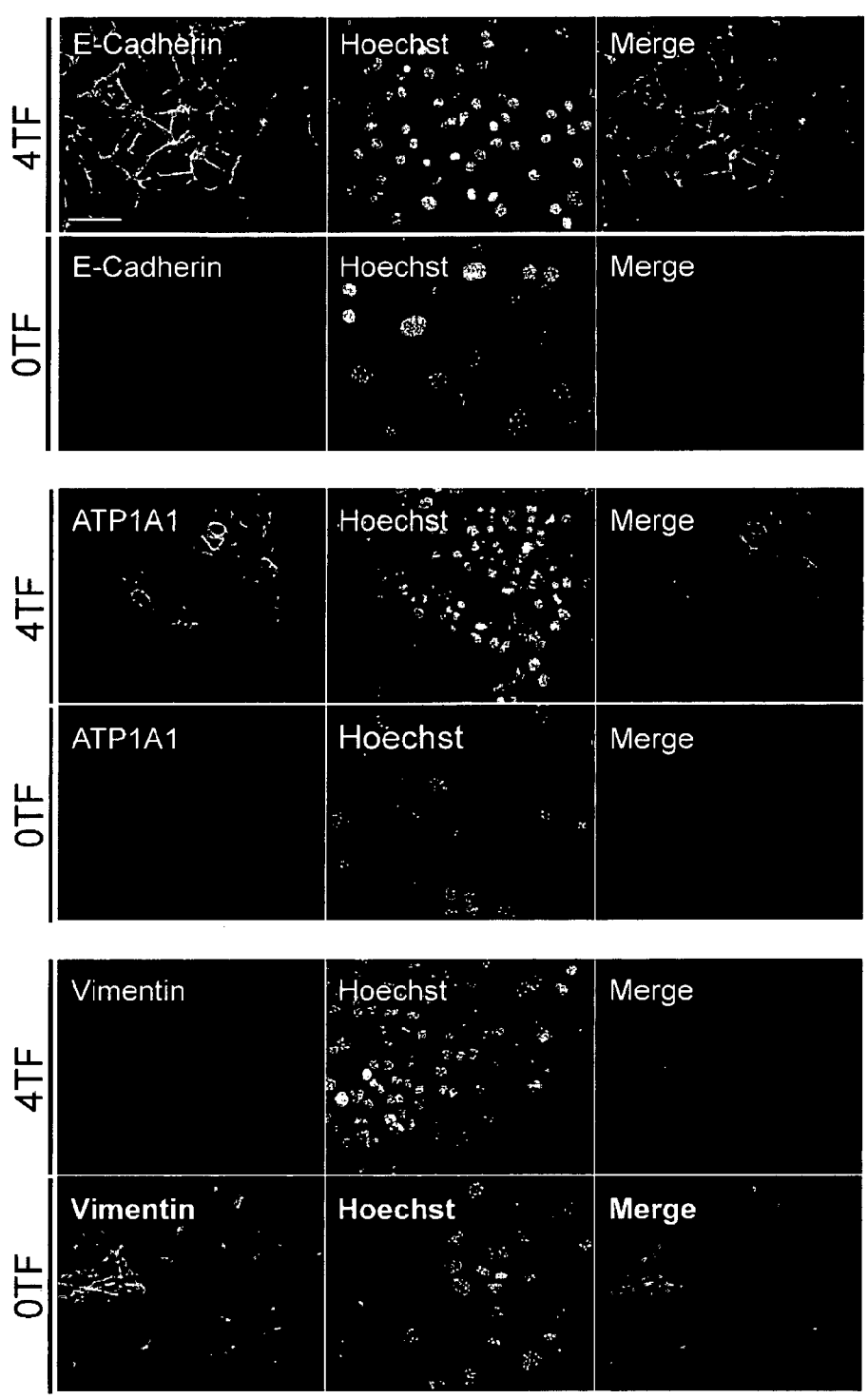

FIG. 11: iRECs can be induced by a multicistronic lentiviral vector and can be generated from adult tail tip fibroblasts.

(a) Flow cytometry (FC) analysis of control MEFs obtained from membrane-tomato red mice (TOM CTL) and from membrane-GFP mice (GFP CTL) used for FC gate setting. MIX CTL: mixture of membrane-tomato red MEFs and membrane-GFP MEFs. (b) Vector map of the multicistronic construct showing the four reprogramming factors (Pax8, Hnf1b, Emx2, Hnf4a) separated by 2A peptide sequences. pWPXLd was used as lentiviral backbone. (c) Expression of 2A-tagged TFs was controlled using an antibody against the 2A consensus peptide motif. GFP transfected cells served as a control. (d) FC analysis of GFP$^+$ cells in KSP-Cre reporter MEFs treated with a lentivirus harboring the multicistronic vector after 39 days of culture. (e) FC analysis for the presence of GFP+ cells in MEFs, young TTFs (P7) and adult TTFs (P60) 1 and 5 weeks after high titer lentiviral infection with 4TFs (Pax8, Emx2, Hnf4a and Hnf1b); representative FC plots are shown, percentage of GFP$^+$ cells is indicated with standard error for the respective experiment. (f) Immunostaining of 0TF or 4TF treated adult TTFs for the indicated proteins. Scale bar, 50 µm (f).

FIG. 12. Transcriptome analysis of iRECs.
(a) Median RPKM (Reads per kilobase per million mapped reads) in human (left diagrams) and mouse (middle and right diagrams) global gene expression profiles of 10-fold upregulated and downregulated genes in iRECs compared to MEFs or primary RECs[30, 31] Error bars: quantile range. (b) Median RPKM in global gene expression across renal tubular segments[39] of differentially regulated genes as indicated. Error bars: quantile range. (c) Gene ontology term analysis of 10-fold upregulated genes in iRECs compared to MEFs.

Figure 13:
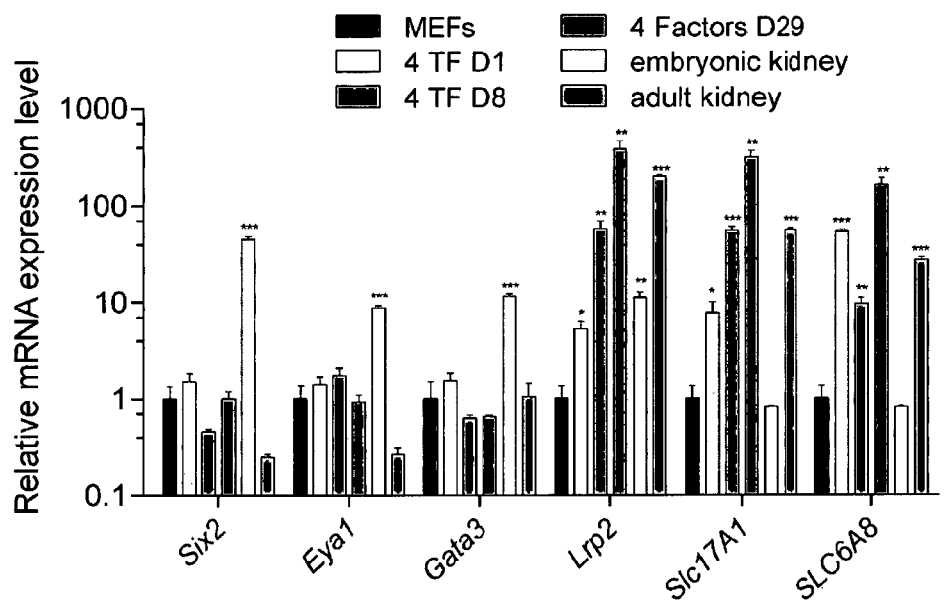
Figure 13:
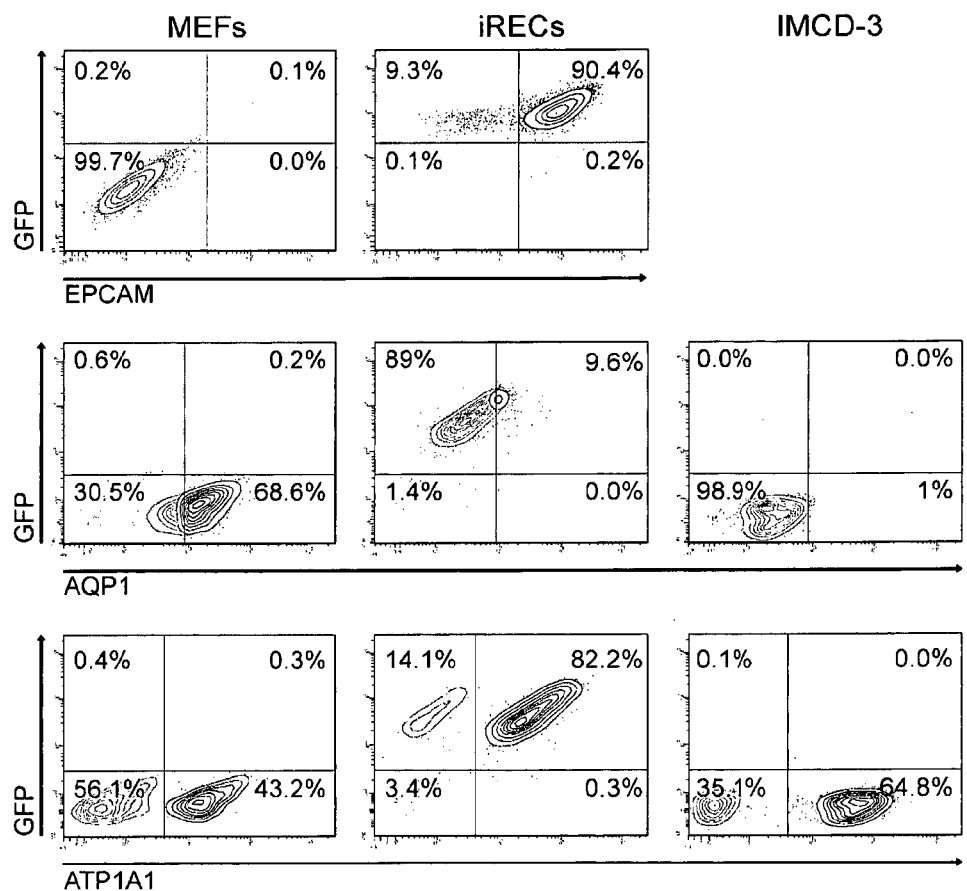
Figure 13:
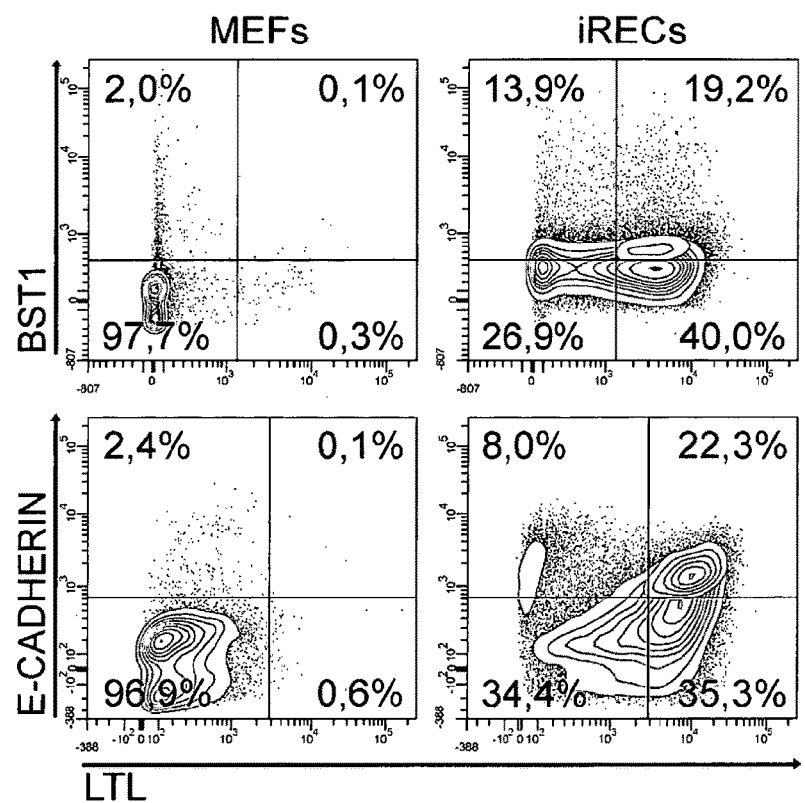
Figure 13:
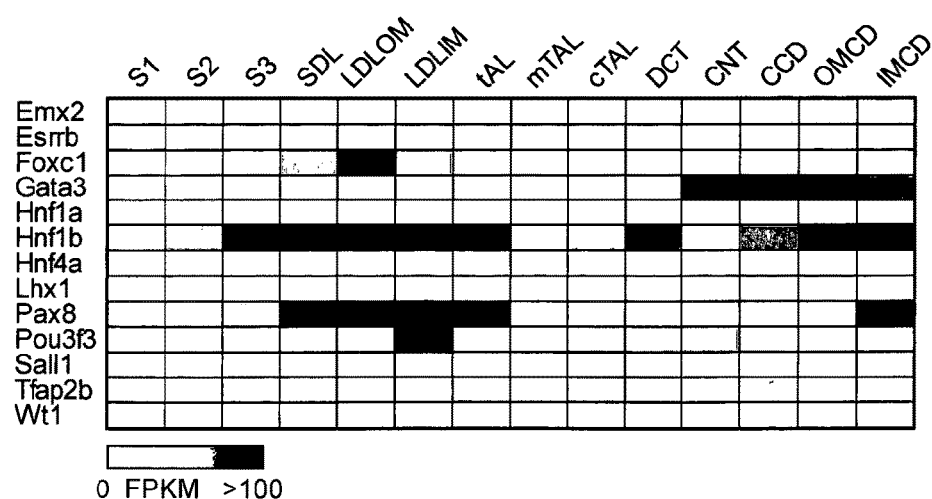

FIG. 13. Segment identity and stability of iRECs
(a) qPCR time course analysis of progenitor and differentiation markers in untreated MEFs and 4TF treated MEFs at day 1, 8 and 29 after infection. Embryonic and adult kidneys served as controls. (b) FC of MEFs, iRECs and IMCD-3 cells analyzed for expression of GFP and EPCAM, AQP1, and ATP1A1. The percentage of cells within each quadrant is given. (c) Co-immunostaining of iRECs for proteins with segment restricted expression as detected by FC. Proximal tubule cells were detected by LTL (Lotus tetragonolobus) staining. (d) Expression levels of the 13 candidate reprogramming factors in microdissected tubule segments of adult rats[39] (e) RNA sequencing based expression analysis of genes regulated by Hnf4a or Emx2. The left panel shows an expression intensity heatmap of differentially upregulated genes in 4TF treated vs. untreated MEFs by at least one $\log_2$ change (replicate set statistics, p<0.0001) and in MEFs treated with only 3 factors (omitting either Emx2 or Hnf4a). The right panel shows a heatmap of the expression of the same genes across tubular segments[39]. Genes in both heatmaps are sorted according to the median expression difference between proximal segments S1-3 (top) and collecting duct tissues (bottom). (f) qRT-PCR analysis for detection of exogenous reprogramming factors. iRECs EX: generated with a LoxP containing provirus for removal of the exogenous reprogramming factors after CRE expression. iRECs: generated with a provirus lacking loxP sites for constitutive expression. (g) Immunostaining of iRECs and iRECsEX for the indicated proteins. (h) mRNA expression levels of the indicated genes as determined by qRT-PCR in MEFs and iRECs EX. (i) Relative proportion of Ki-67 positive iRECs and MEFs after 10 (P10), 20 (P20) and 40 (P40) passages. Different letters indicate significant differences as assessed by One-way ANOVA followed by Tukey's post-hoc test (p<0.05). (j) Relative levels of p16 mRNA as determined by qPCR in P20 and P40 iRECs and MEFs. ns, not significant, Student's t-test. (k) qPCR analysis of renal differentiation makers in iRECs after one and three months of culture. Error bars: SEM, Student's unpaired t-test, n=3, * p<0.001,  p<0.01, * p<0.05.

Figure 14:
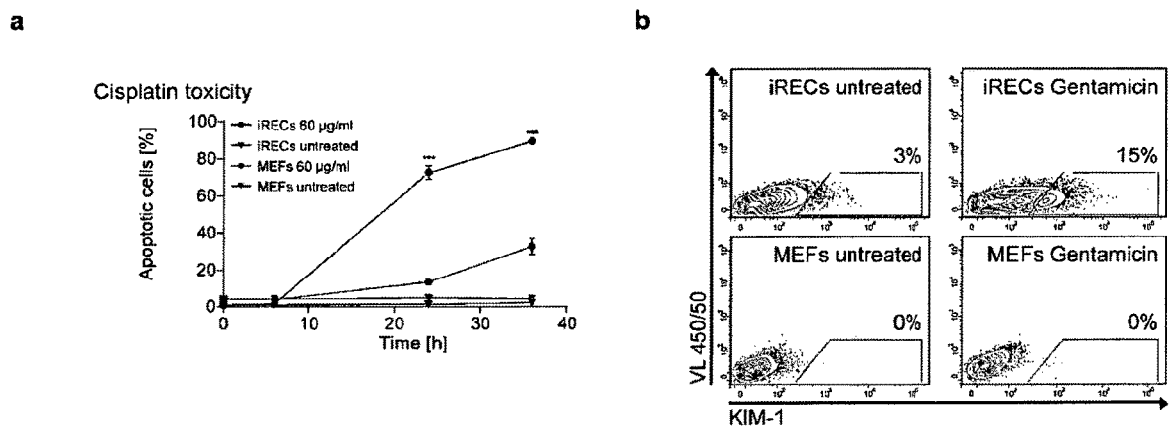
Figure 14:
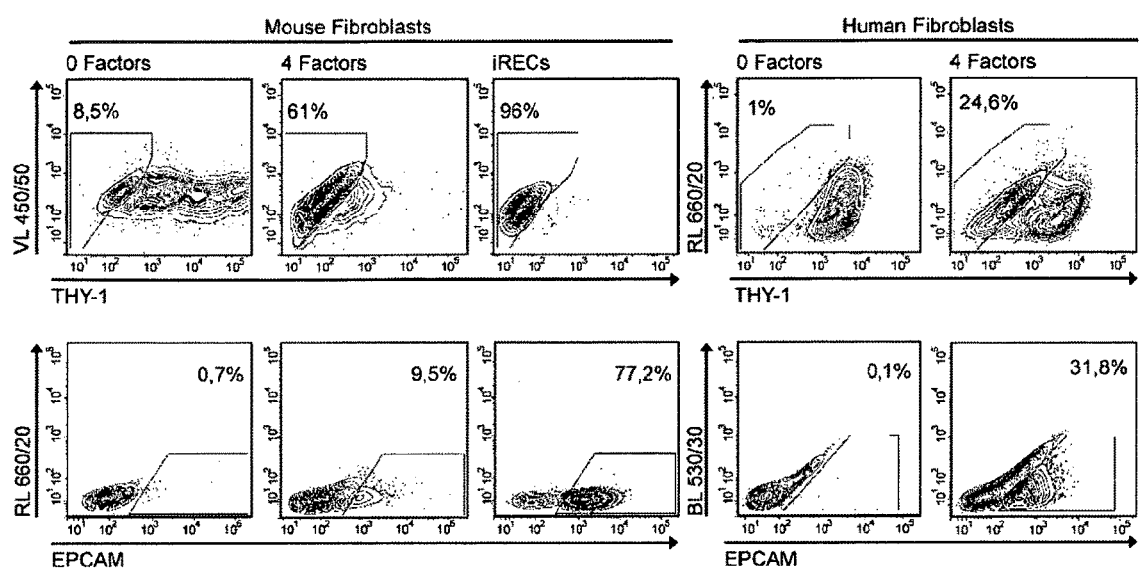
Figure 14:
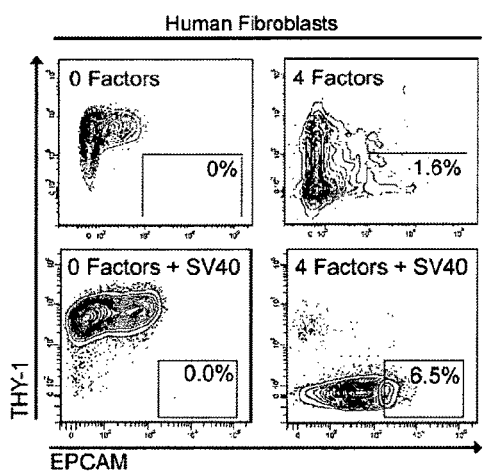
Figure 14:
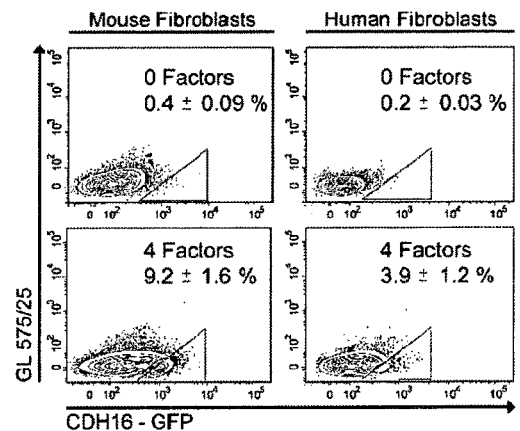

FIG. 14. Cytotoxicity testing in murine iRECs and improvement of human iREC induction efficiency and specificity.
(a) Quantification of apoptotic cells (%) in cisplatin treated MEFs (red line) and iRECs (black line) or untreated controls. Error bars: SEM, Student's unpaired t-test, n=3, * p<0.001,  p<0.01, * p<0.05. (b) FC analysis for KIM1 expression in iRECs and MEFs treated with gentamicin (1 mg/ml). (c) Percentage of THY-1$^-$ or EPCAM$^+$ cells in mouse and human fibroblasts after treatment with 4TF as determined by FC. (d) Percentage of THY-1$^-$ and EPCAM$^+$ human fibroblasts after treatment with SV40 (large T antigen), 4TF or SV40 and 4TF as determined by flow cytometry. (e) Percentage of CDH16-GFP$^+$ reporter mouse and human fibroblasts after treatment with 4 TFs as determined by flow cytometry. Fibroblasts were transduced with a CDH16-GFP reporter plasmid and SV40, selected for GFP$^-$ cells with stable integration of the reporter and infected with 4TFs.

Figure 15:
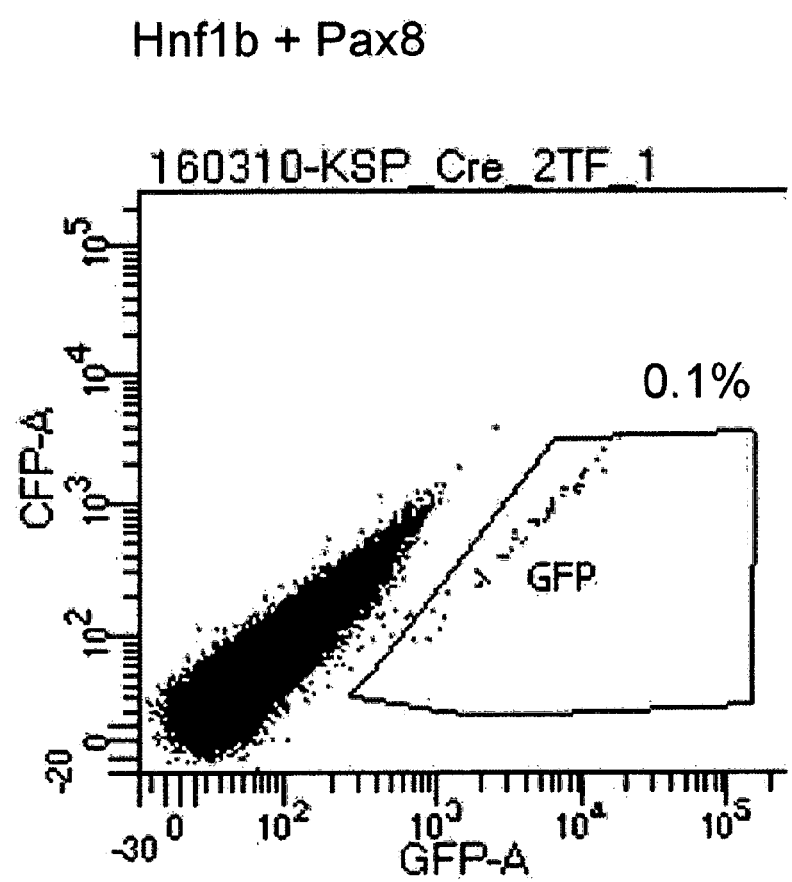

FIG. 15. Overexpression of Hnf1b and Pax8 is sufficient for reprogramming.
Experiments were carried out as described for FIG. 2b, but with overexpression of Pax8 and Hnf1b only. Ksp-Cre positive cells were detected after 3 weeks of culture.

Figure 16:
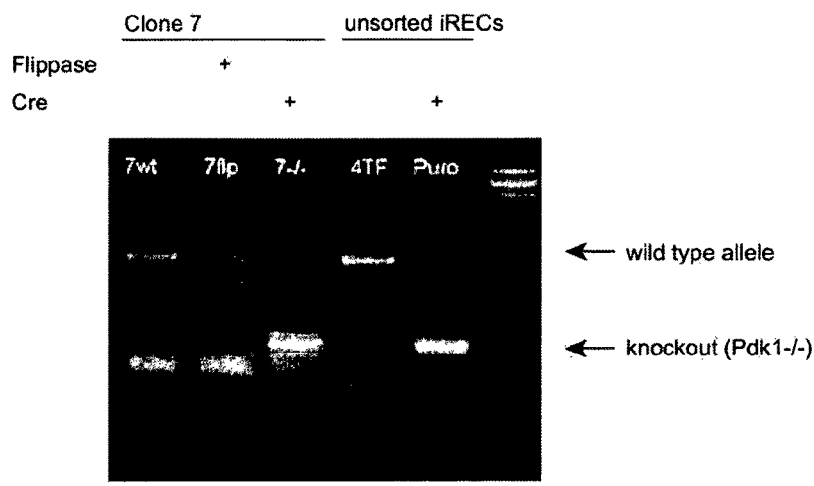
Figure 16:
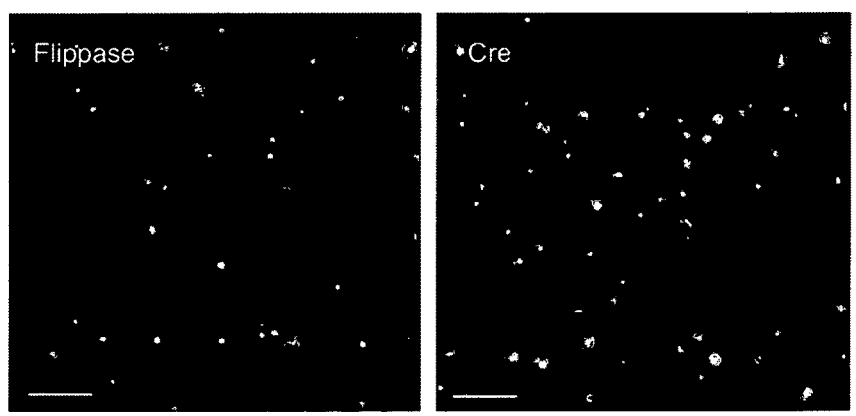
Figure 16:
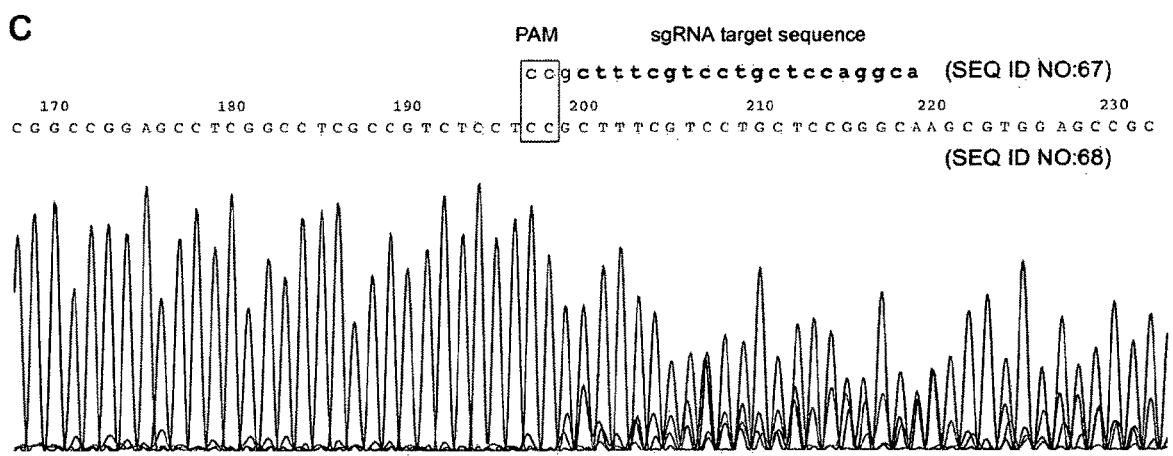

FIG. 16:
(a) MEFs isolated from Pdk1fl/fl mice were reprogrammed to iRECs by expression of 4TFs. Clones derived after single cell sorting (lanes 1-3), and the unsorted cell population (lanes 4,5) were treated with Cre for excision of the floxed allele, or Flippase or untreated as controls. A representative gel image of clone 7 is shown, exemplarily. The unsorted population was puromycin treated to select for Cre expressing cells. The lower band indicates the excised allele ($Pkd1^{-/-}$), the upper band is the wild type allele.

(b) Clonally expanded iRECs, treated with Flippase or Cre, were seeded into matrigel, grown for one week and stained with phalloidin (green) and DAPI (blue). Images are maximum intensity projections of confocal z-stacks.

(c) Sanger sequencing chromatogram of wild-type iRECs after CRISPR/Cas9 targeting of the first exon of Pkd2. The PAM-sequence is indicated by a black box, the sequence in bold is the sgRNA target. Notice the scrambled chromatogram at the expected cleavage site, shortly 3' of the PAM, indicating successful indel formation in the unsorted cell population.

DETAILED DESCRIPTION

The present invention relates to a method for producing renal cells, comprising overexpressing at least Hnf1b and Pax8 and optionally Emx2 and/or Hnf4a in differentiated cells. The method of the invention requires overexpression of Hnf1b and Pax8 in differentiated cells. Preferably, Hnf1b, Pax8 and Hnf4a are overexpressed. More preferably, Hnf1b, Pax8 and Emx2 are overexpressed. Most preferably, Emx2, Hnf1b, Pax8 and Hnf4a are overexpressed.

The term "differentiated cell" as used herein refers to a cell in the process of differentiating into a somatic cell lineage or having terminally differentiated. For example, embryonic cells can differentiate into an epithelial cell lining the intestine. Differentiated cells can be isolated from a fetus or a live born animal, for example.

Preferably, the differentiated cells are fibroblasts. Other suitable types of differentiated cells include cells of the mononuclear phagocyte system (MPS) (=Reticuloenothelial system) and other renal cell types.

Fibroblasts

The term "fibroblast", as used herein, refers to a cell of mesenchymal origin. Fibroblasts are found in connective tissue. Fibroblasts synthesize actin-myosin filaments, the matrix elements (collagen, reticular and elastic fibers), and glycosaminoglycans and glycoproteins, which are secreted as amorphous intercellular substance. Fibroblasts include connective-tissue stem cells, matrix- and other protein-synthesizing cells, contractile cells, and phagocytic cells. Active fibroblasts are characterized by their abundant endoplasmic reticulum (ER), Golgi complex and ribosomes.

Fibroblasts play a particularly critical role during embryogenesis. Besides synthesizing proteins, they determine the structure of the skeleton, the location of muscle cells, the growth patterns of nerve fibers and the organization of the skin. Fibroblasts accomplish these organizational functions by attaching collagenous fibrils to embryonic cells and pulling them into the proper alignment to form parts of the developing organism. During human development and throughout adulthood, fibroblasts continue to synthesize and maintain both loose and dense types of connective tissue. They migrate in response to a number of chemoattractants such as lymphokines, cytokines and growth factors and constantly remodel and repair tissues by producing various degradative and synthetic enzymes, including collagenase, and products that may modulate the function of other cells including prostaglandins, tissue plasminogen activator (tPA), complement components and superoxide dismutase.

The importance of fibroblasts may be attributed to their production of collagen, the predominant extracellular component of connective tissue and the most abundant protein in the human body.

The biology of fibroblasts and matrix proteins is discussed by Postlethwaite and Kang, In: Inflammation: Basic Principles and Clinical Correlates, 2d ed, Gallin et al. (1992) Raven Press, New York, pp 747-773.

In one embodiment, the fibroblasts are embryonic fibroblasts. The term "embryonic" as used herein refers to the age when the fibroblasts are obtained, i.e. the fibroblasts are obtained from an embryo, preferably at the age of E11.5-E14.5.

In another embodiment, the fibroblasts are adult fibroblasts. The term "adult" as used herein refers to the age when the fibroblasts are obtained, i.e. the fibroblasts are obtained from an adult subject. An adult subject in accordance with this invention has an age of more than 8 weeks.

In yet another embodiment, the fibroblasts are postnatal fibroblasts. Postnatal fibroblast are typically obtained from newborn subjects shortly after birth, e.g. within one week after birth, or at about one week after birth.

The fibroblast may be identified by immunocytochemistry using one or more of the following antibodies: (i) an antibody capable of binding to vimentin, (ii) an antibody capable of binding to prolyl-4-hydroxylase, and (iii) the antibody TE-7 (commercially available from EMD Millipore, Catalog No. CBL271; see also Haynes, B. F., et al. (1984). J. Exp. Med. 159(4):1149-1168).

In embodiment A, the fibroblast carries a surface antigen that is recognized by the antibody TE-7. In embodiment B, the fibroblast expresses vimentin. In embodiment C, the fibroblast expresses prolyl-4-hydroxylase. Further aspects of the invention are combinations of embodiments A and B, A and C, B and C, and A, B and C.

Renal Cells

The term "renal cell", as used herein, refers to a cell having the characteristics of a kidney cell or residing within the kidney or originating from the metanephric mesenchyme or the ureteric bud.

The renal cells obtained in accordance with this invention preferably express the genes Pax2, Lhx1, Slc6a18, Slc17a1 and/or Lrp2, and/or they show upregulation of one or more of these genes relative to the fibroblasts from which they originated.

Preferably, the renal cell is a renal tubular cell. More preferably, the renal cell expresses the marker protein "kidney-specific Cadherin", also termed Cadherin-16 (see also Thomson et al. (1995) J Biol Chem 270 (29): 17594-17601; and Shen et al. (2005) Mod Pathol. 18(7): 933-940 and references cited therein). Antibodies against Cadherin-16 are commercially available.

Most preferably, the renal cell is an epithelial renal cell, e.g. a renal tubular epithelial cell. The epithelial renal cells are typically characterized by the presence of the poteins ZO-1, E-cadherin (CDH1) and EpCAM at the membrane of the epithelial renal cells.

The epithelial renal cells preferably express Cdh1, which encodes E-cadherin, and Cdh6, and/or the expression of these genes is greater than that in the fibroblasts from which they originated.

In addition, the renal cells are preferably negative for vimentin, or at least the expression of vimentin in the renal cells is significantly lower than that in the fibroblasts from which they originated.

Unless indicated otherwise, all references to expression levels herein refer to a determination by quantitative Real-time PCR, as defined in the examples.

Transcription Factors

The EMX2 gene encodes a homeobox-containing transcription factor that is the homolog to the 'empty spiracles' gene in *Drosophila*. Research on this gene in humans has focused on its expression in three tissues: dorsal telencephalon, olfactory neuroepithelium, and urogenetial system. It is expressed in the dorsal telencephalon during development in a low rostral-lateral to high caudal-medial gradient and is proposed to pattern the neocortex into defined functional areas. It is also expressed in embryonic and adult olfactory neuroepithelia where it complexes with eukaryotic translation initiation factor 4E (elF4E) and possibly regulates mRNA transport or translation. In the developing urogenital system, it is expressed in epithelial tissues and is negatively regulated by HOXA10. Alternative splicing results in multiple transcript variants encoding distinct proteins.

The human ortholog of EMX2 protein has the amino acid sequence deposited under UniProtKB/Swiss-Prot accession number Q04743. Isoform 1 has the accession number Q04743-1, whereas isoform 2 has the accession number Q04743-2.

Isoform 1 is encoded by a cDNA sequence with the following details:

| LOCUS | NM_004098 2908 bp |
|---|---|
| DEFINITION | Homo sapiens empty spiracles homeobox 2 (EMX2), transcript variant 1, mRNA. |
| ACCESSION | NM_004098 |
| VERSION | NM_004098.3 GI:164607120 |

Isoform 2 is encoded by a cDNA sequence with the following details:

| LOCUS | NM_001165924 2723 bp |
|---|---|
| DEFINITION | Homo sapiens empty spiracles homeobox 2 (EMX2), transcript variant 2, mRNA. |
| ACCESSION | NM_001165924 |
| VERSION | NM_001165924.1 GI:260064071 |

Any nucleotide sequence encoding human EMX2, an ortholog thereof, or a functional fragment thereof, can be used in accordance with this invention. The nucleic acid encoding EMX2 may have a sequence identity of at least 80%, preferably of at least 90%, to the nucleotide sequence as shown in SEQ ID NO:1 [accession number NM_004098]; For reprogramming mouse fibroblasts the nucleotide sequence as shown under accession number NM_010132.2 can be used.

The Hnf1b gene encodes a member of the homeodomain-containing superfamily of transcription factors. The protein binds to DNA as either a homodimer, or a heterodimer with the related protein hepatocyte nuclear factor 1-alpha. The gene has been shown to function in nephron development, and regulates development of the embryonic pancreas. Mutations in this gene result in renal cysts and diabetes syndrome and noninsulin-dependent diabetes mellitus, and expression of this gene is altered in some types of cancer. Multiple transcript variants encoding different isoforms have been found for this gene.

The human ortholog of HNF1B has the amino acid sequence as defined under UniProtKB/Swiss-Prot accession number P35680. This includes the isoforms defined under accession numbers P35680-1, P35680-2, P35680-3, and P35680-4.

Corresponding mRNA sequences include, but are not limited to, the nucleotide sequences defined under accession numbers:
BC017714.1, XM_011546821.1, NM_006481.1, NM_000458.3, XM_011546819.1, XM_011546822.1, XM_011525162.1, NM_001165923.3, XM_011525163.1, XM_011525160.1, XM_011546823.1, XM_011546820.1, NM_001304286.1, XM_011525161.1, and XM_011525164.1

Any nucleotide sequence encoding human HNF1B, an ortholog thereof, or a functional fragment thereof, can be used in accordance with this invention. The nucleic acid encoding HNF1B may have a sequence identity of at least 80%, preferably of at least 90%, to the nucleotide sequence as shown in SEQ ID NO:2 [accession number BC017714.1]. For reprogramming mouse fibroblasts the nucleotide sequence as shown under accession number NM_009330.2 can be used.

The HNF4A protein is a nuclear transcription factor which binds DNA as a homodimer. The encoded protein controls the expression of several genes, including hepatocyte nuclear factor 1 alpha, a transcription factor which regulates the expression of several hepatic genes. Mutations in this gene have been associated with monogenic autosomal dominant non-insulin-dependent diabetes mellitus type I. Alternative splicing of this gene results in multiple transcript variants encoding several different isoforms.

The human ortholog of HNF4A has the amino acid sequence as defined under UniProtKB/Swiss-Prot accession number P41235. This includes the isoforms defined under accession numbers P41235-1, P41235-2, P41235-3, P41235-4, P41235-5, P41235-6 and P41235-7.

Corresponding mRNA sequences include, but are not limited to, the nucleotide sequences defined under accession numbers:
NM_001287182.1, NM_001030003.2, NM_175914.4, XM_005260407.2, NM_001030004.2, NM_001287183.1, NM_178849.2, XM_011528797.1, NM_000457.4, NM_001287184.1, NM_178850.2, NM_001258355.1 and XM_011528798.1.

Any nucleotide sequence encoding human HNF4A, an ortholog thereof, or a functional fragment thereof, can be used in accordance with this invention. The nucleic acid encoding HNF1B may have a sequence identity of at least 80%, preferably of at least 90%, to the nucleotide sequence as shown in SEQ ID NO:3 [accession number NM_000457.4]. For reprogramming mouse fibroblasts the nucleotide sequence as shown under accession number NM_008261.2 can be used.

The Pax8 gene encodes a member of the paired box (PAX) family of transcription factors. Members of this gene family typically encode proteins that contain a paired box domain, an octapeptide, and a paired-type homeodomain. This nuclear protein is involved in thyroid follicular cell development and expression of thyroid-specific genes. Mutations in this gene have been associated with thyroid dysgenesis, thyroid follicular carcinomas and atypical follicular thyroid adenomas. Alternatively spliced transcript variants encoding different isoforms have been described.

The human ortholog of PAX8 has the amino acid sequence as defined under UniProtKB/Swiss-Prot accession number Q06710. This includes the isoforms defined under accession numbers Q06710-1, Q06710-2, Q06710-3, Q06710-4 and Q06710-5.

Corresponding mRNA sequences include, but are not limited to, the nucleotide sequences defined under accession numbers:
BC001060, XM_011511792.1, NM_013951.3, NM_013952.3, NM_013953.3, XM_011511790.1, XM_011511793.1, NM_013992.3, NM_003466.3, XM_011511794.1 and XM_011511791.1.

Any nucleotide sequence encoding human PAX8, an ortholog thereof, or a functional fragment thereof, can be used in accordance with this invention. The nucleic acid encoding PAX8 may have a sequence identity of at least 80%, preferably of at least 90%, to the nucleotide sequence as shown in SEQ ID NO:4 [accession number BC001060]. For reprogramming mouse fibroblasts the nucleotide sequence as shown under accession number NM_011040.4 can be used.

The term "overexpression" as used herein means that the expression level of a given gene in a host cell transfected with a nucleic acid encoding the gene is greater than the endogenous expression level of the gene in the non-transfected host cell. For example, if the fibroblasts transfected with an expression vector encoding Emx2 show a higher expression level of Emx2 nucleic acid than the non-transfected fibroblasts, there is overexpression of Emx2 in the transfected cells.

The expression level is preferably determined by quantitative Real-Time-PCR.

Fibroblasts may be obtained from the following sources:
Mouse embryonic Fibroblasts may be obtained from the limbs of E11.5-E14.5 embryos.
Postnatal mouse Fibroblasts may be obtained from the tail tips of about 1 week old mice.
Adult mouse fibroblasts may be obtained from the tail tips of about 8 week old mice.
Human Foreskin Fibroblasts may be obtained from the foreskin of a healthy boy, e.g. a 6 year old boy.
Human Fetal Fibroblasts may be obtained from fetal skin (commercially obtainable e.g. from ScienCell Research Laboratories)

In a certain embodiment, the method of the invention comprises only steps carried out in vitro and/or ex vivo. Accordingly, no step is carried out on the living human or animal body according to this embodiment.

The method of the invention preferably comprises the steps (a) providing one or more nucleic acids encoding HNF1b and PAX8 and optionally EMX2 and/or HNF4a; (b) introducing said one or more nucleic acids into the fibroblasts so as to obtain transduced fibroblasts; and (c) culturing said transduced fibroblasts under conditions that allow overexpression of Hnf1b and Pax8 and optionally of Emx2 and/or Hnf4a.

The nucleic acids encoding EMX2, HNF1b, HNF4a and/or PAX8 can be non-circular nucleic acids. Preferably, however, the nucleic acids encoding EMX2, HNF1b, HNF4a and/or PAX8 are comprised in a circular nucleic acid, more preferably in a plasmid or a vector. The nucleic acids are typically operably linked to a promoter sequence which is capable of inducing gene expression in fibroblasts. Suitable promoters include, but are not limited to, CMV, EF1a, SV40, PGK1, Ubc, human beta actin, CAG, and TRE.

The nucleic acids encoding EMX2, HNF1b, HNF4a and/or PAX8 can be on four separate plasmids or vectors. Preferably, however, a plasmid or vector to be used in accordance with this invention comprises nucleotide sequences encoding at least two proteins selected from the group consisting of EMX2, HNF1b, HNF4a and PAX8. In another embodiment, a plasmid or vector to be used in accordance with this invention comprises nucleotide sequences encoding at least three proteins selected from the group consisting of EMX2, HNF1b, HNF4a and PAX8. In yet another embodiment, the plasmid or vector to be used in accordance with this invention comprises nucleotide sequences encoding the proteins EMX2, HNF1b, HNF4a and PAX8. That is, the plasmid or vector comprises coding sequences for all of the four genes Emx2, Hnf1b, Hnf4a and Pax8 or functional equivalent thereof.

The nucleic acid, plasmid or vector can be introduced into the fibroblasts or differentiated cells using techniques that are known per se.

Methods suitable for introducing nucleic acids sufficient to achieve expression of a protein of interest into mammalian host cells are known in the art. See, for example, Gething et al., Nature, 293:620-625, 1981; Mantei et al., Nature, 281:40-46, 1979; Levinson et al. EP 117,060; and EP 117,058. For mammalian cells, common methods of introducing genetic material into mammalian cells include the calcium phosphate precipitation method of Graham and van der Erb (Virology, 52:456-457, 1978) or the Lipofectamine™ (Gibco BRL) Method of Hawley-Nelson (Focus 15:73, 1993). General aspects of mammalian cell host system transformations have been described by Axel in U.S. Pat. No. 4,399,216. For various techniques for introducing genetic material into mammalian cells, see Keown et al., Methods in Enzymology, 1989, Keown et al., Methods in Enzymology, 185:527-537, 1990, and Mansour et al., Nature, 336:348-352, 1988.

In some embodiments of the methods of the invention, the step of introducing nucleic acid comprises delivering the nucleic acid into the cell (e.g., a human or other animal somatic cell) with a transfection reagent. However, the invention is not limited by the nature of the transfection method utilized. Indeed, any transfection process known, or identified in the future that is able to deliver nucleic acid into cells in vitro or in vivo, is contemplated, including methods that deliver the nucleic acid into cells in culture or in a life-supporting medium, whether said cells comprise isolated cells or cells comprising a eukaryotic tissue or organ, or methods that deliver the nucleic acid in vivo into cells in an organism, such as a human, animal, plant or fungus. In some embodiments, the transfection reagent comprises a lipid (e.g., liposomes, micelles, etc.). In some embodiments, the transfection reagent comprises a nanoparticle or nanotube. In some embodiments, the transfection reagent comprises a cationic compound (e.g., polyethylene imine or PEI). In some embodiments, the transfection method uses an electric current to deliver the mRNA into the cell (e.g., by electroporation).

The nucleic acid can be introduced by transfection or transduction into the cells using a vector, such as an integrating- or non-integrating vector. Of particular interest herein are retroviral vectors. Retroviral vectors, particularly lentiviral vectors, are transduced by packaging the vectors into virions prior to contact with a cell. After introduction, the DNA segment(s) encoding the potency-determining factor(s) can be located extra-chromosomally (e.g., on an episomal plasmid) or stably integrated into cellular chromosome(s).

A viral-based gene transfer and expression vector is a genetic construct that enables efficient and robust delivery of genetic material to most cell types, including non-dividing and hard-to-transfect cells in vitro or in vivo. Viral-based constructs integrated into genomic DNA result in high expression levels. In addition to a DNA segment that encodes a transcription factor of interest, the vectors include a transcription promoter and a polyadenylation signal operatively linked, upstream and downstream, respectively, to the DNA segment. The vector can include a single DNA segment encoding a single potency-determining factor or a plurality of potency-determining factor-encoding DNA segments. A plurality of vectors can be introduced into a single cell. The vector can optionally encode a selectable marker to identify cells that have taken up and express the vector. As an example, when the vector confers antibiotic resistance on the cells, antibiotic can be added to the culture medium to identify successful introduction of the vector into the cells. Integrating vectors can be employed, as in the examples, to demonstrate proof of concept. Retroviral (e.g., lentiviral) vectors are integrating vectors; however, non-integrating vectors can also be used. Such vectors can be lost from cells by dilution after reprogramming, as desired. A suitable non-integrating vector is an Epstein-Barr virus (EBV) vector. Ren C, et al., Acta. Biochim. Biophys. Sin. 37:68-73 (2005); and Ren C, et al., Stem Cells 24:1338-1347 (2006), each of which is incorporated herein by reference as if set forth in its entirety.

The vectors described herein can be constructed and engineered using art-recognized techniques to increase their safety for use in therapy and to include suitable expression elements and therapeutic genes. Standard techniques for the construction of expression vectors suitable for use in the present invention are well-known to one of ordinary skill in the art and can be found in such publications such as Sambrook J, et al., "Molecular cloning: a laboratory manual," (3rd ed. Cold Spring Harbor Press, Cold Spring Harbor, N.Y. 2001), incorporated herein by reference as if set forth in its entirety.

After transfection or transduction, the cells are typically cultured under suitable conditions to allow overexpression of the transfected genes. The culture period from introduction of the gene into the fibroblasts until conversion of the cells into renal cells is typically at least 5 days, preferably at least 10 days, or 5 to 30 days, preferably 10 to 20 days, e.g. 10 days, 11 days, 12 days, 13 days, 14 days, 15 days, 16 days, 17 days, 18 days, 19 days or 20 days.

Suitable culture conditions include, but are not limited to, those described in the examples.

The renal cells obtained by the methods described herein can then be collected or recovered for further use as shown in the examples.

Possible uses include, but are not limited to, nephrotoxicity testing, pharmacological screening or disease modeling. The diseases which can be modeled using the renal cells of the present invention include, but are not limited to, conditions affecting the renal tubules, transport deficiencies (e.g. Bartter syndrome), metabolic syndromes affecting renal tubules (e.g. cytinosis), ciliopathies (e.g. nephronophthisis), end stage renal disease, cystic kidney disease, polycystic kidney disease, Congenital anomalies of the kidney and urinary tract (CAKUT), Renal cystic diseases, interstitial diseases and tumorous kidney diseases; Renal tubular diseases, metabolic diseases, and nephrolithiasis.

Reprogramming in accordance with this invention and/or the renal cells obtained thereby can be used to develop in vitro disease models from genetically altered animal models.

Direct disruption of genes associated with human kidney disease can be achieved in renal cells obtained in accordance with the invention. The cells of the invention can be used to generate novel in vitro disease models, e.g. by direct targeting disease associated genes. This is not limited to cystic kidney disease, but can easily be applied to any condition that affects the renal tubules, including transport deficiencies (e.g. Bartter syndrome), metabolic syndromes that affect renal tubules (e.g. cystinosis), or ciliopathies (e.g. nephronophthisis), among others.

EXAMPLES

Results

Identification of Renal Cell Fate Inducing Transcription Factors

Figure 1:
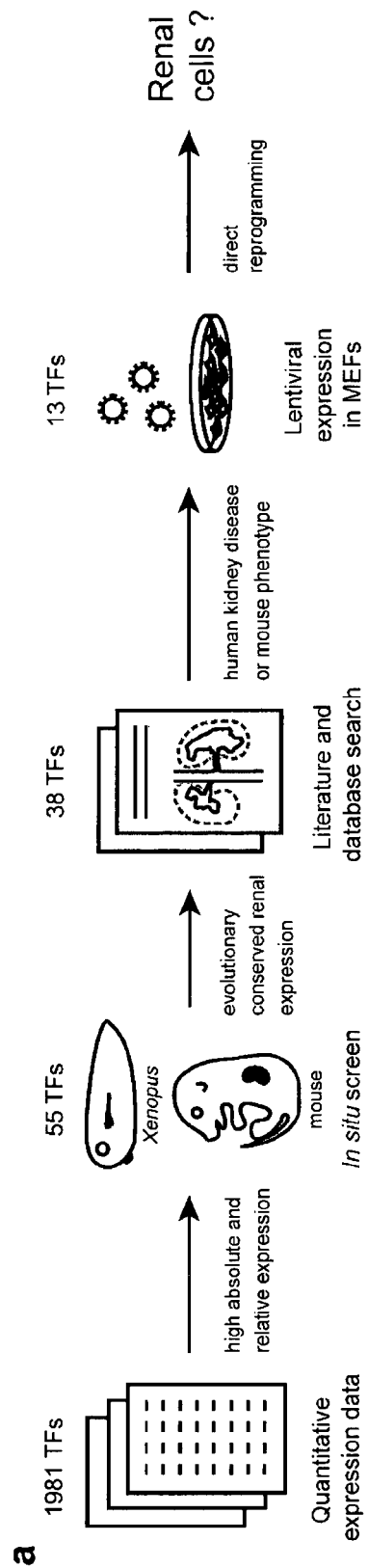
FIG. 1: Systematic selection criteria identify candidate reprogramming factors.
(a) Schematic illustrating the strategy and criteria used to identify renal reprogramming factors. TFs: transcription factors. (b) Scatter-plots depicting the absolute and relative expression levels of transcription factors in liver, brain and kidney tissue[23]. Factors used for successful reprogramming to hepatocytes and neurons are highlighted in red. Dashed lines indicate the level of the 50th percentile of absolute expression and the 95th percentile of relative expression. The area boxed in red includes the 55 candidate reprogramming factors for renal cell types. (c) Representative images of in situ hybridizations of the indicated genes on E14 mouse kidney sections and stage 26 Xenopus whole-mount embryos. The full set of images is contained in FIGS. 8-9. Scale bars, 500 µm (c).
Figure 1:
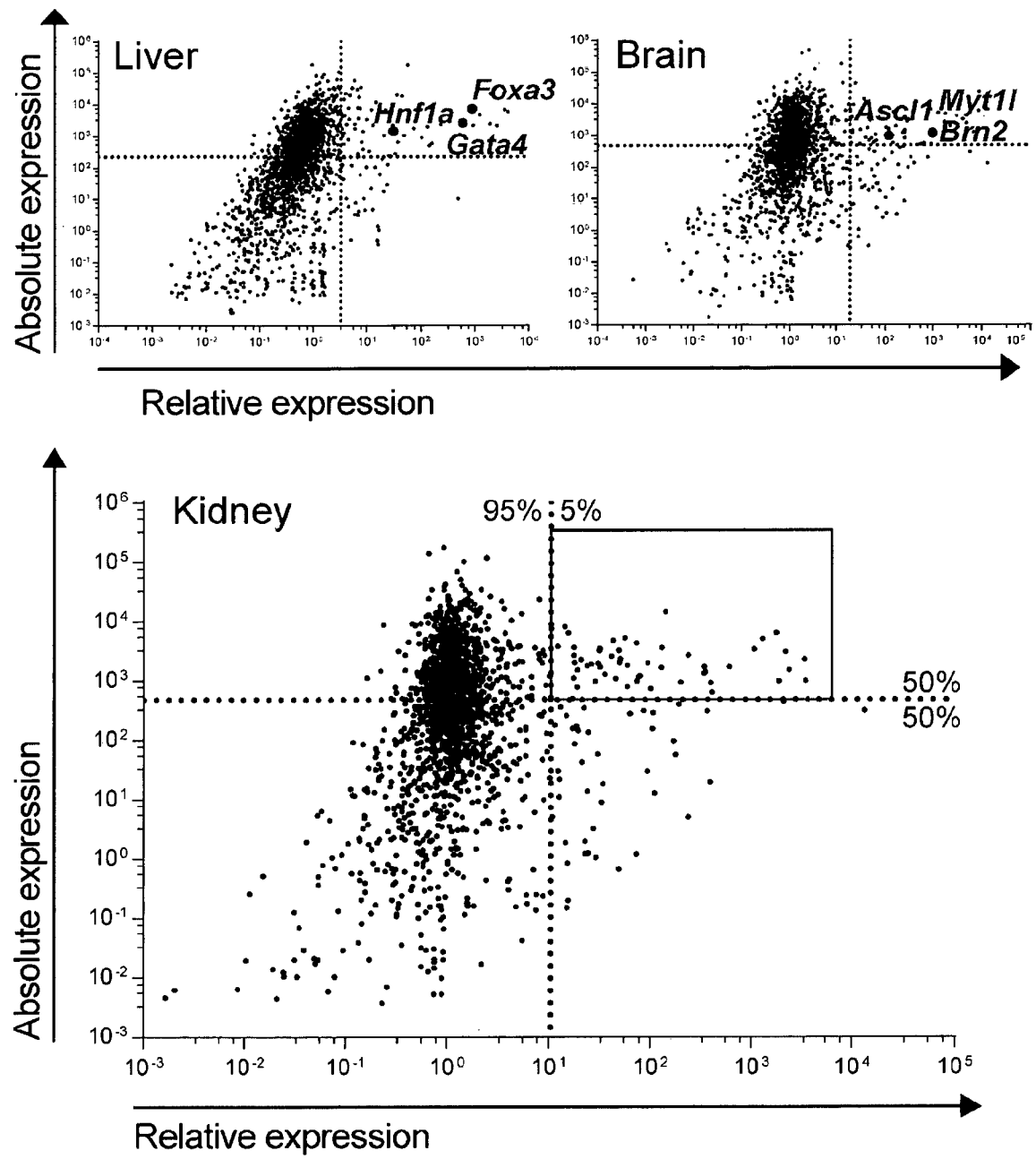
Figure 1:
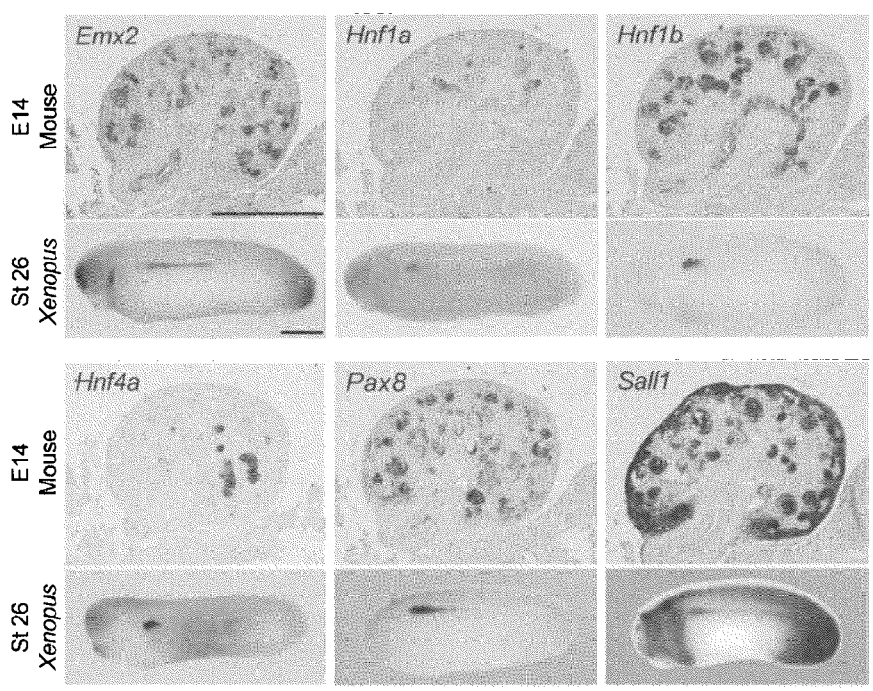

To define criteria for the unbiased selection of candidate kidney reprogramming factors (FIG. 1a), we analyzed quantitative mRNA expression data of all known transcription factors across different adult human tissues[23] (FIG. 1b and FIG. 8a). A feature of previously identified reprogramming factors is their high absolute expression in their target tissue and high relative expression in comparison to other tissues. Based on these criteria a set of 55 candidate kidney reprogramming factors could be defined.

Core regulators of renal identity are likely to have an evolutionary conserved function during early nephrogenesis. Central aspects of Xenopus laevis pronephros development and function exhibit remarkable similarities to mammalian kidney development[24]. Therefore, we performed a comparative in situ hybridization screen of orthologous genes to the 55 human candidate factors in Xenopus (FIG. 1c and FIGS. 8b,9). 38 genes showed a distinct expression in the pronephros; 18 were detected at the earliest time point (stage 22). Similar early and tissue-restricted expression during mouse metanephros development was detected in embryonic day 12 (E12) to E17 kidney anlagen (FIG. 1c and FIG. 10)[25-27].

As a third selection criterion for potential reprogramming factors, genes associated with congenital renal disease in humans, or renal loss-of-function phenotypes in mouse were considered essential for renal development and further investigated. This stepwise selection reduced the number of potential reprogramming factors to 13 candidates that were functionally tested for their potency to induce renal cell fate.

Emx2, Hnf1b, Hnf4a and Pax8 Convert Fibroblasts into iRECs

First, we tested if individual or combinations of candidate reprogramming factors could direct mammalian cells towards renal cell fate. Because candidate factors were predicted based on expression data from whole kidneys, we aimed to induce tubule epithelial cells that constitute the major cell type of the kidney.

Figure 2:
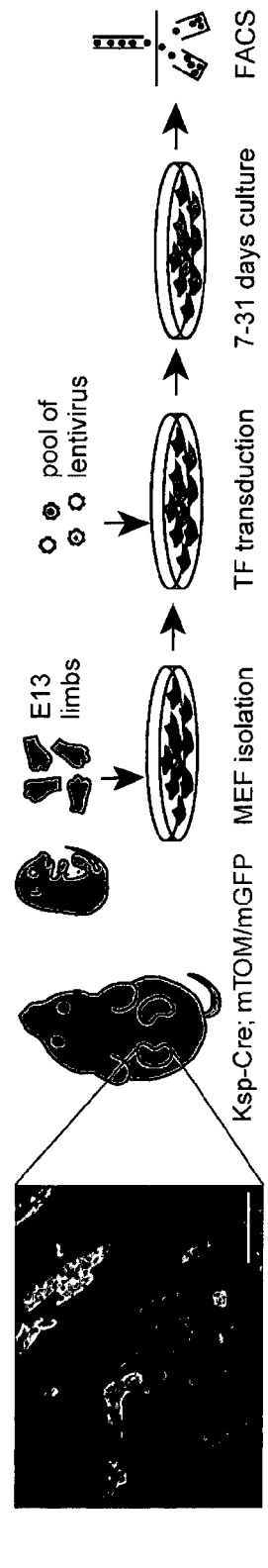
FIG. 2: Four transcription factors can induce renal cell fate in mouse embryonic fibroblasts (MEFs).
(a) Schematic of the experimental procedure used to identify renal reprogramming factors. A kidney section from adult KSP-Cre; mTOM/mGFP reporter mice shows membrane-GFP expression (mGFP) in the renal tubules and membrane-tomato red fluorescence (mTOM) in the remaining tissue. (b) MEFs derived from limbs of reporter mice were left untreated (0 factors) or transduced with the pool of 13 transcription factors (13TF) and analyzed by flow cytometry (FC) for the presence of GFP positive (GFP$^+$) cells 7 days after viral transduction. Confocal images show GFP$^+$ cells (green), mTOM$^+$ cells (red), and nuclear staining with Hoechst (blue) (c) Percentages of GFP$^+$ cells in different 13TF-1 combinations were assessed by FC; 0TF: untreated MEFs; CFP: cyan fluorescent protein. The broken line marks the average percentage of GFP$^+$ cells in the pool of 13TFs. (d) Percentage of GFP$^+$ cells in different 8TF-1 combinations as assessed by FC. (e) FC analysis and representative confocal image of GFP$^+$ cells transduced with the pool of 4 TFs (Emx2, Hnf1b, Hnf4a, Pax8). (f) FC analysis of GFP$^+$ cells in MEFs overexpressing the 4TFs, combinations of three TFs, or single factors. (g) FC analysis and representative confocal image of 4TF treated cells after 31 days of culture. (h) Reprogramming efficiency in MEFs 1 week after lentiviral infection. LV: low virus concentration; HV: high virus concentration; MC: multicistronic vector; CHIR: CHIR99021; VITC: Vitamin C; VA: valproic acid; AZA: 5-azacytidine; FORS: forskolin. The broken line marks the average percentage of GFP$^+$ cells in 4TF HV treated cells. Error bars: standard error of the mean (SEM), Asterisks indicate significant differences to the positive control (13TF (c), 8TF(d) 4TF(f) and 4TF HV(h)) as assessed by Student's unpaired t-test, n=3, * $p<0.001$,  $p<0.01$, * $p<0.05$, Scale bars, 100 µm (a,b,e,g)
Figure 2:
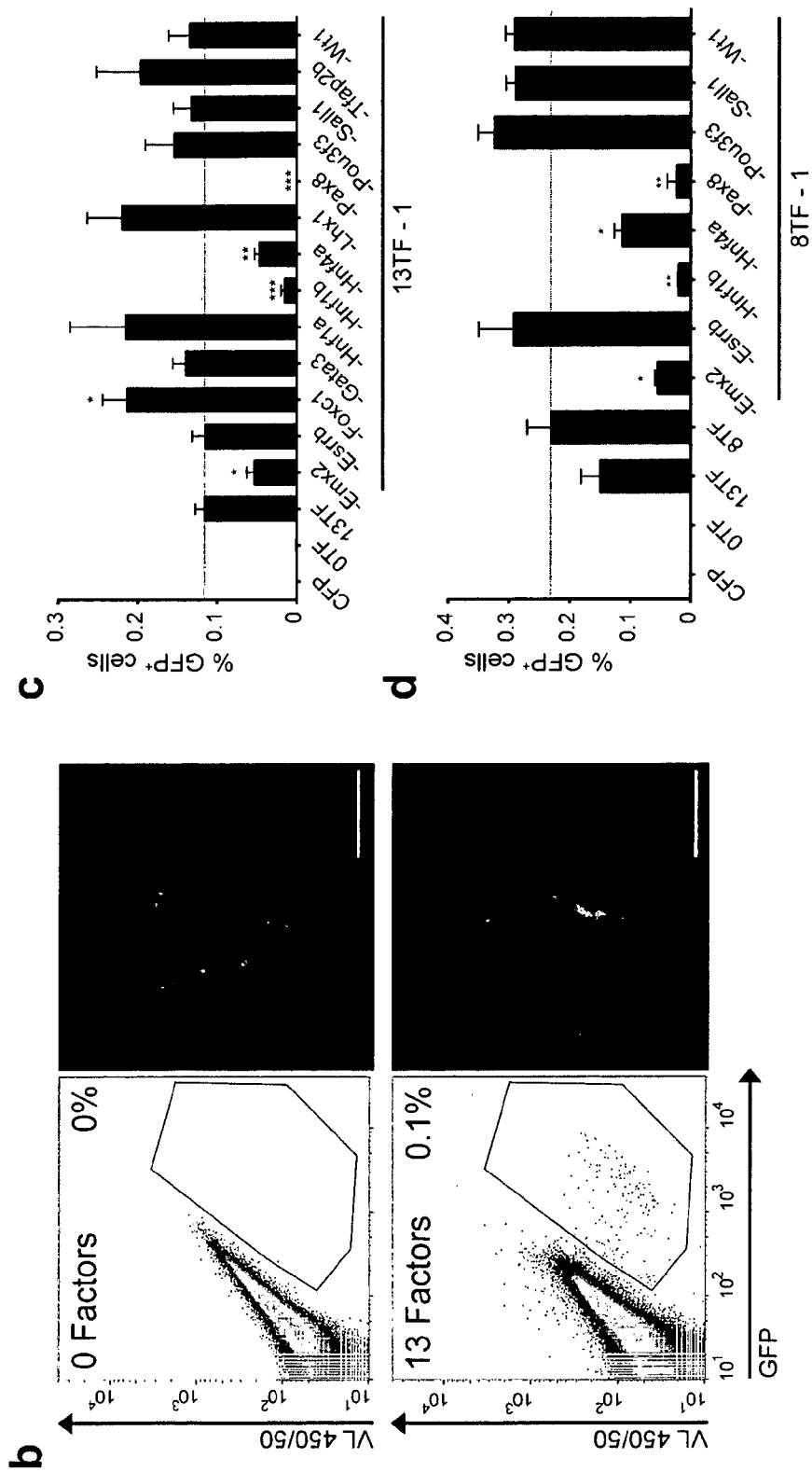
Figure 2:
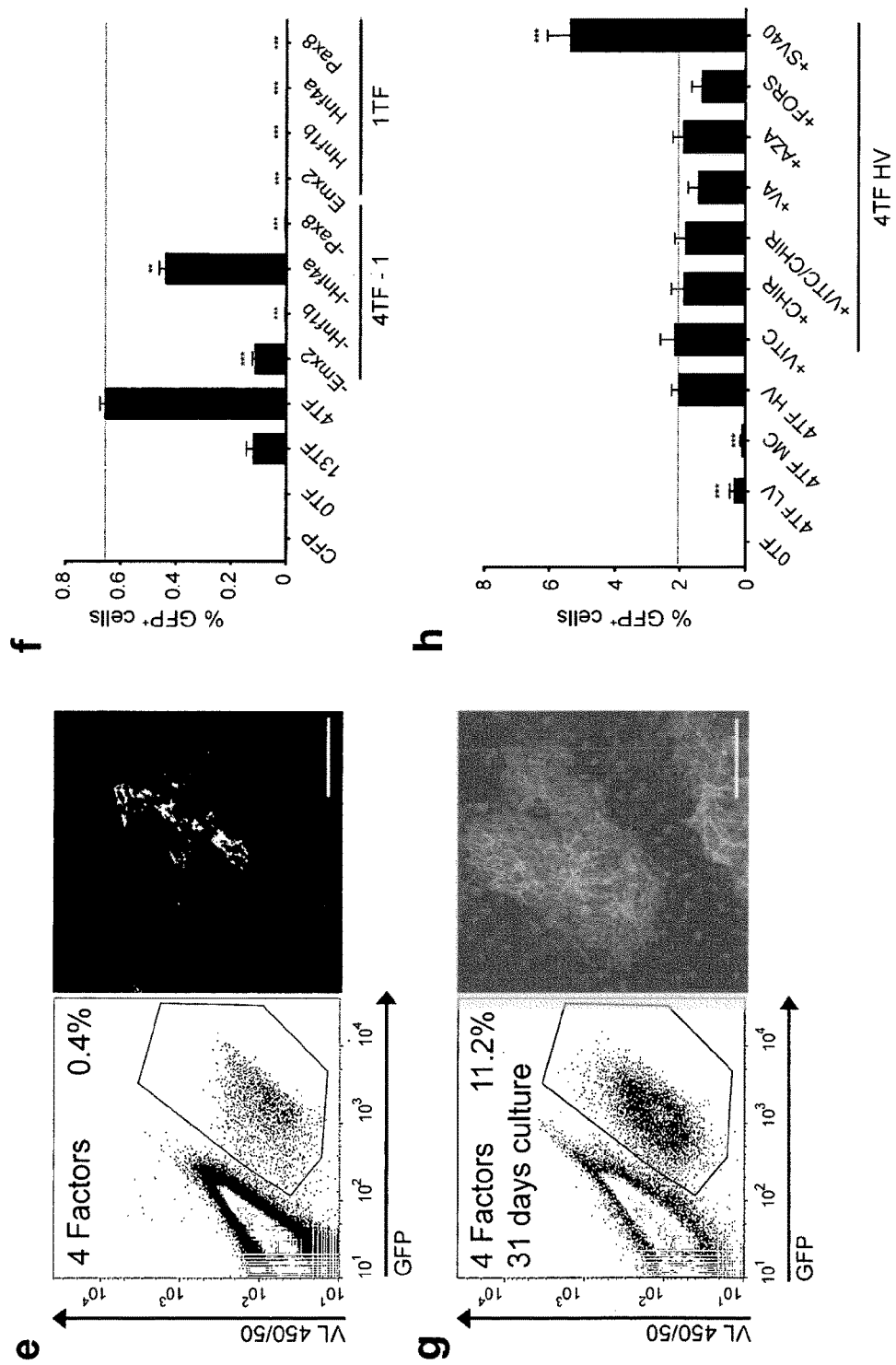

To detect fate conversion towards tubule cell identity, we crossed mice harboring Cre-recombinase under control of the renal tubule-specific cadherin-16 promoter (Cdh16/Ksp-Cre (kidney specific protein)) to mice with a membrane-tandem dimer tomato red/membrane-GFP (mTOM/mGFP) dual fluorescent reporter[28]. In resulting mice Cre-mediated recombination induces the expression of membrane GFP specifically in renal tubular epithelial cells, while non Cre-expressing cells maintain red fluorescence (FIG. 2a). We isolated mouse embryonic fibroblasts (MEFs) from limbs of E13 embryos carrying the reporter system to exclude potential contamination with renal precursor cells. Next, we expressed candidate transcription factors in isolated MEFs by lentiviral transduction and analyzed GFP reporter-expression by flow cytometry (FIG. 2a and FIG. 11a).

When a cocktail of all 13 candidate factors was transduced, 0.1% of cells expressed GFP one week after transduction (FIG. 2b). To determine the minimal set of factors required for kidney-fate induction, we systematically removed individual candidates from the pool of 13 transcription factors (13TF-1; FIG. 2c). Withdrawal of Foxc1, Gata3, Hnf1a, Lhx1, and Tfap2b increased the percentage of GFP-positive cells. Consequently, these factors were excluded from the following experiments (8TF-1; FIG. 2d). Removal of each of the four factors Emx2, Hnf1b, Hnf4a, and Pax8, either from the pools of 13 or 8 factors significantly reduced the percentage of GFP-positive cells (FIGS. 2c,d). Conversely, the combined expression of these four factors significantly increased the average percentage of GFP-positive cells to 0.6%. Importantly, none of the four factors could induce reporter activity when overexpressed individually (FIGS. 2e,f). 31 days after lentiviral transduction the percentage of GFP-positive cells increased to 11.2% (FIG. 2g).

Next, we systematically tested which conditions would enhance reprogramming efficiency. Increasing the virus titers resulted in a 3-fold higher rate of reporter activation after one week of culture (FIG. 2h) and up to 23.8% GFP+ cells after 5 weeks (FIG. 11e). Vitamin C, CHIR99021, valproic acid, 5 azacytidine, or forskolin, substances previously shown to facilitate reprogramming[29, 30, 31] did not have an effect on the percentage of GFP-positive cells. Similar, expression of all four transcription factors from a single, multicistronic vector did not increase conversion efficiency (FIG. 2h and FIGS. 11b,c,d). However, co-expression of the SV40 large T antigen[32] further increased reprogramming efficiency to 5.4% one week after infection (FIG. 2h).

To evaluate if postnatal fibroblasts could similarly be used for reprogramming, tail-tip fibroblasts from postnatal day 7 (P7) or from adult (P60) mice were transduced with four factors. The detection of GFP-positive cells indicated that reprogramming towards renal epithelial fate was not limited to embryonic fibroblasts (FIGS. 11e,f).

In conclusion, a combination of four factors (i.e. Emx2, Hnf1b, Hnf4a, Pax8) is sufficient to activate renal tubule specific reporter expression in embryonic, and postnatal fibroblasts. Resulting cells were subsequently referred to as induced renal tubular epithelial cells (iRECs).

iRECs Show Epithelial Characteristics

Figure 3:
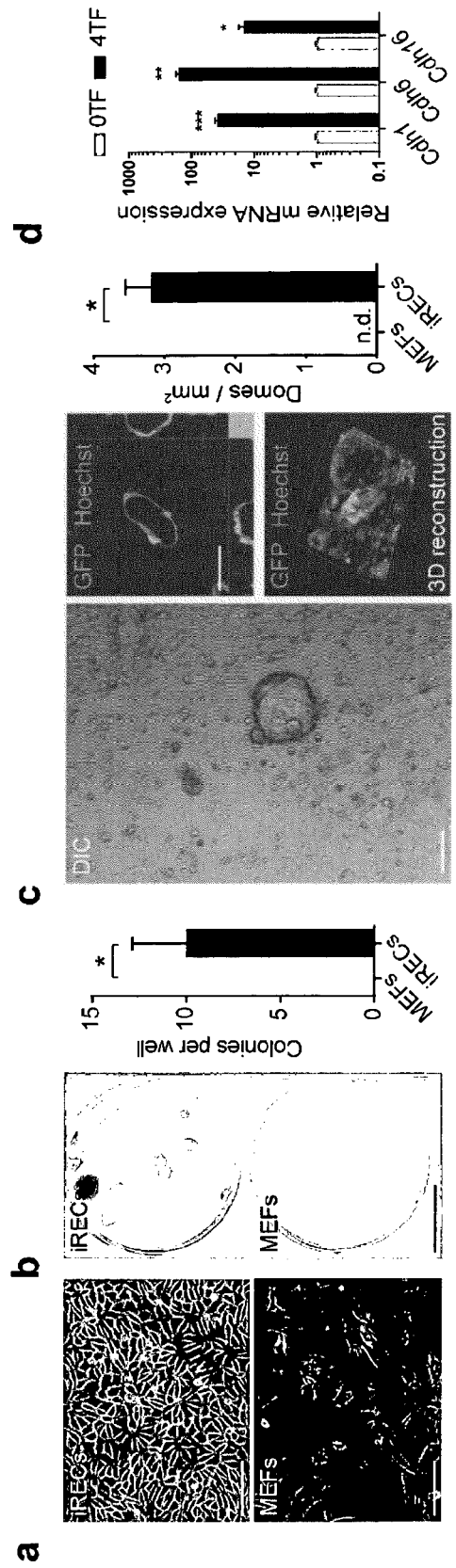
FIG. 3: iRECs exhibit epithelial properties.
(a) Phase contrast images of iRECs and MEFs show epithelial and mesenchymal cell morphologies, respectively. (b) Colony formation of iRECs and MEFs was assessed by crystal violet staining; Quantification of colonies formed by MEFs and iRECs after 2 weeks of culture. (c) Differential interference contrast (DIC) and confocal imaging: densely seeded iRECs display dome formation as observed in orthogonal view (upper right panel) and by 3D reconstruction of confocal z-stacks (lower right panel); Quantification of domes per mm$^2$ of densely seeded iRECs. (d) Relative mRNA expression levels of indicated genes as determined by qRT-PCR in untreated and 4TF treated MEFs. (e) Immunofluorescence staining of the epithelial (ZO-1, E-Cadherin, Epcam) and mesenchymal (Vimentin) marker proteins in iRECs and MEFs.
Figure 3:
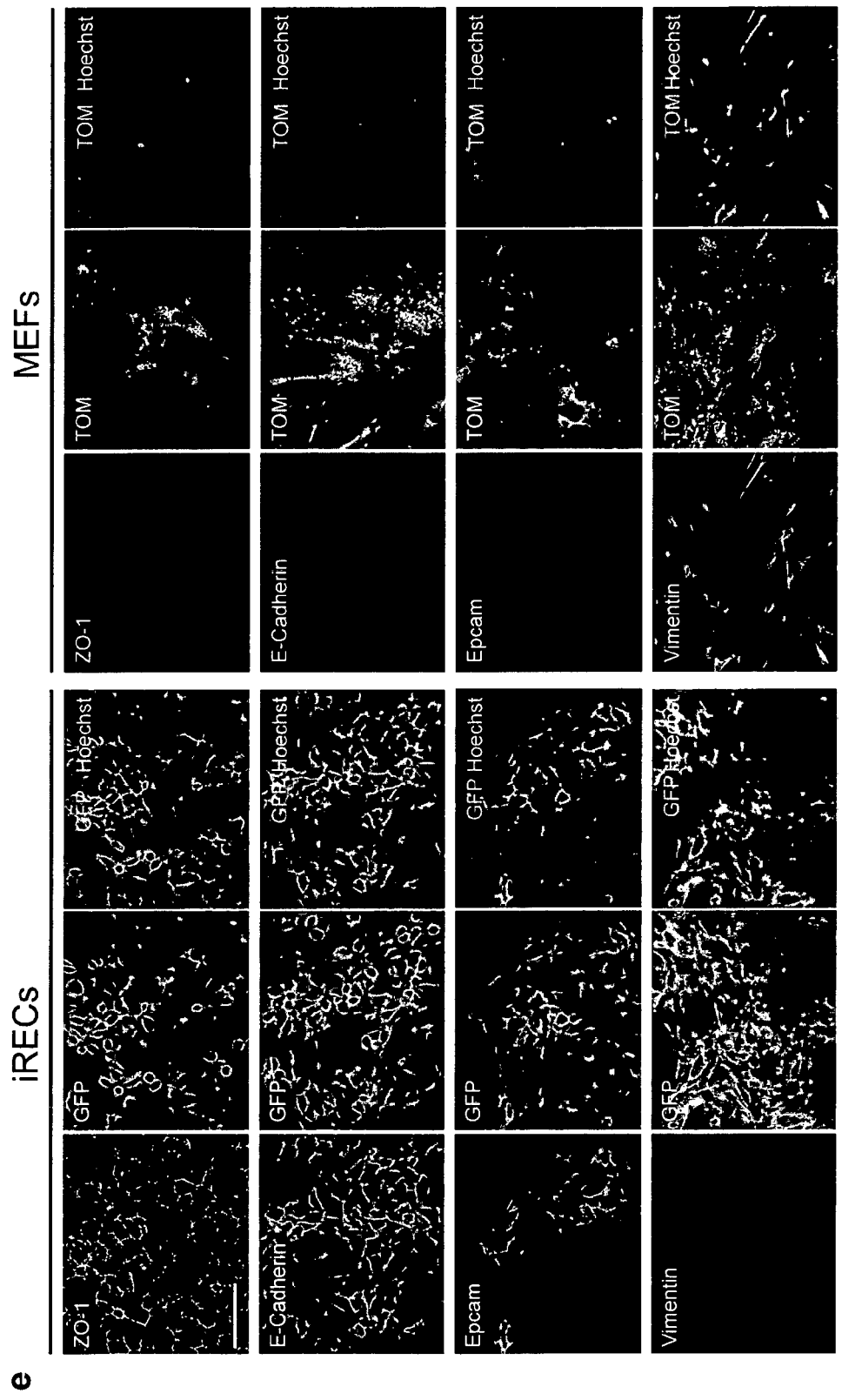

To characterize iRECs, GFP-positive cells were isolated by fluorescence-activated cell sorting (FACS) and expanded in culture. iRECs exhibited a characteristic epithelial morphology and formed a tight epithelial layer when grown to confluency (FIG. 3a). Sparsely seeded cells formed colonies after 2 weeks of culture, suggesting that iRECs have the capacity of clonogenic expansions[17] (FIG. 3b). Densely grown iRECs frequently exhibited dome-like structures (FIG. 3c), a characteristic feature of renal epithelial cells indicative of directed transport of solutes and water influx[33].

Next, we analyzed mRNA levels of epithelial cell adhesion molecules with a strong expression in renal tubule cells. Both Cdh1 and Cdh6 transcripts, and as expected from Ksp-Cre reporter activation, Cdh16 (Ksp) were robustly expressed in iRECs (FIG. 3d).

In addition, immunostaining for ZO-1, E-cadherin (CDH1) and EPCAM demonstrated membrane localization of these epithelial marker proteins in iRECs, but not in MEFs (FIG. 3e). In contrast, the intermediate filament protein vimentin, marking mesenchymal cells, was present in MEFs, but absent in iRECs. Thus, iRECs acquired epithelial cell identity during reprogramming, and had lost their mesenchymal phenotype.

iRECs Resemble Primary Tubule Cells in their Expression Profile

Next, we assessed the global transcriptional profile of iRECs in comparison to FACS-isolated primary renal tubule cells from P7 Ksp-Cre mTOM/mGFP mice and MEFs. Hierarchical clustering analysis of microarray data indicated that primary renal tubular epithelial cells more closely resembled iRECs than MEFs (FIG. 4a).

Recently, a quantitative measure for the degree to which engineered cells resemble their target tissue was introduced (CellNet)[34]. Calculation of this classification score is based on gene regulatory network activation and extends from 0 (no similarity) to 1 (indistinguishable). CellNet analysis revealed that iRECs most closely resemble kidney tissue in comparison to any other cell type (FIG. 4b). However, a residual fibroblast signature was also detected. iRECs possessed a mean classification score of 0.30, similar to the score of directly converted neurons (0.34) and cardiomyocytes (0.27) (FIG. 4c). Thus, the degree of similarity of iRECs to the kidney signature matches other previous reprogramming approaches.

We further assessed the expression of kidney-specific marker genes by qRT-PCR. Confirming the microarray data, we detected strong upregulation of transcriptional regulators of kidney development, such as Pax2 or Lhx1, the highly kidney specific amino acid transporter Slc6a18, the organic anion transporter Slc17a1 and the receptor protein Lrp2 among other kidney-enriched transcripts (FIG. 4d).

Figure 12A:
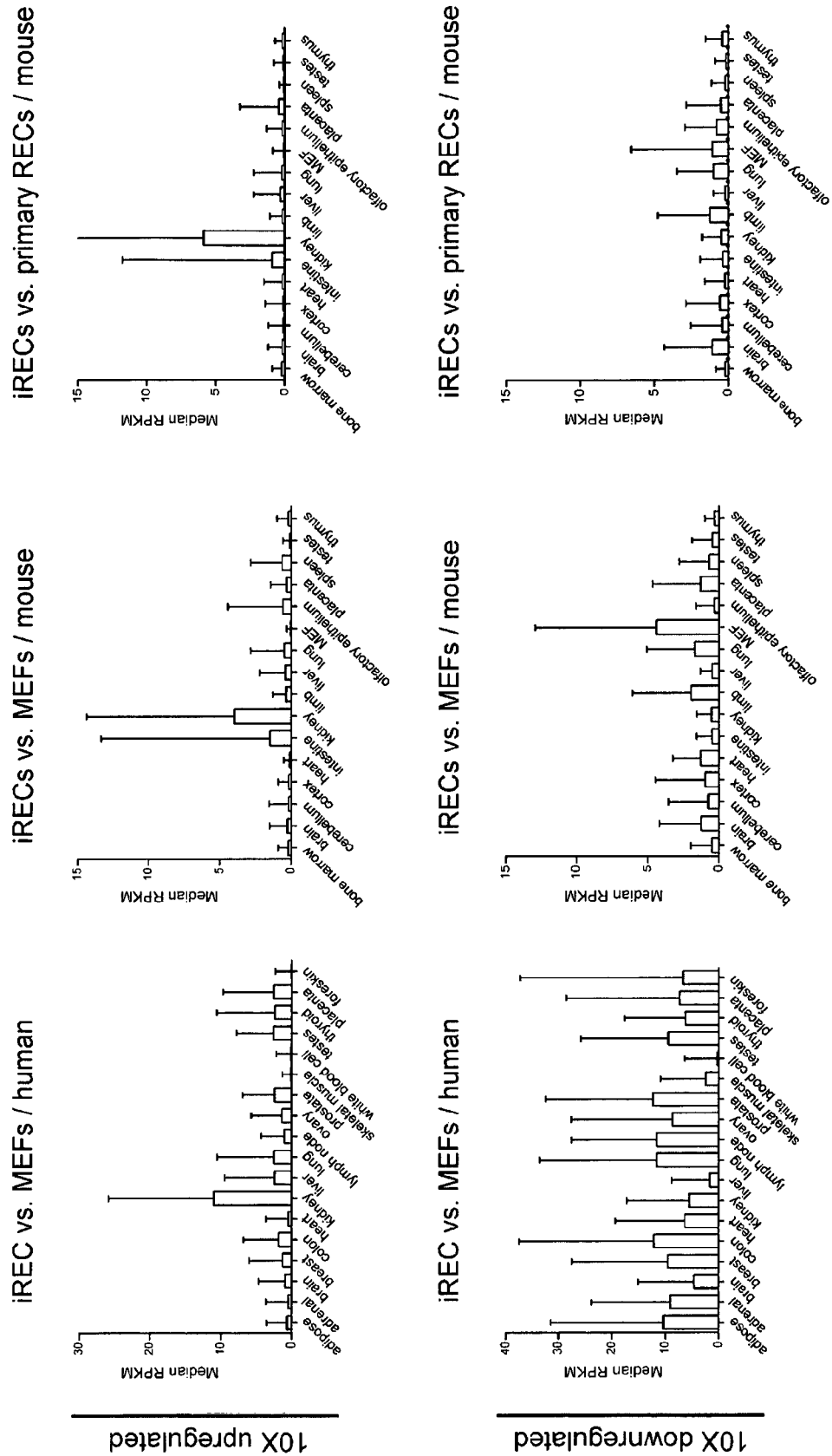

To investigate the main transcriptional changes upon reprogramming to iRECs, expression levels of genes that were differentially regulated in our dataset were related to various mouse and human tissues using published RNA-sequencing expression datasets[35, 36]. Genes that were 10-fold upregulated in iRECs versus MEFs were most abundantly expressed in kidney, while down-regulated genes were strongly expressed in MEFs (FIG. 12a). Genes upregulated in iRECs, compared to primary tubule cells were predominantly expressed in the proximal tubules (FIG. 12b). Gene ontology (GO) analysis revealed that categories associated with transmembrane transport activity were significantly enriched in 10-fold upregulated genes (FIG. 12c), consistent with the elevated expression of tubular expressed ion channels and transporters in iRECs (FIG. 4d). We concluded that the mRNA expression profile of iRECs is most similar to that of renal tissue.

To explore how the combinatorial actions of the 4TFs regulate target gene expression and initiate the transcriptional circuitry of iRECs, we retrieved 164 putative direct target genes of the four reprogramming factors[37] and analyzed their expression levels in iRECs in comparison to MEFs (FIG. 4e). Interestingly, prominent regulators of renal tubule development, such as Pax2, Lhx1, and Hnf1a were strongly induced targets of at least one of the four reprogramming factors. The nephron progenitor marker Osr1 was down-regulated in iRECs and primary tubule cells compared to MEFs. qRT-PCR analysis confirmed that developmentally important progenitor markers, such as Six2, Eya1 or Gata3 were not significantly upregulated one day, one or four weeks after transduction suggesting that iRECs represent differentiated cells rather than renal progenitors (FIG. 13a). Collectively, these analyses indicate that the combinatorial action of the four reprogramming factors regulate the expression of a limited set of downstream transcription factors that may contribute to the reprogramming and maintenance of iREC identity.

Next, we sought to determine if high mRNA transcript levels of renal tubular genes in iRECs were also reflected by protein expression. The alpha1 subunit of the Na+/K+-ATPase (ATP1A1) contributes to blood pressure regulation by controlling sodium excretion[38]. ATP1A1 was detected at the lateral membrane in iRECs, consistent with its subcellular localization and function in vivo (FIG. 4f and FIG. 13b). Immunostaining for the transcription factor PAX2 showed nuclear staining, and Aquaporin 1 (AQP1) was detected at the membrane (FIG. 4f). Thus, iRECs showed correct subcellular localization of the analyzed proteins.

iRECs Represent Multiple Tubule Segments

Global profiling of iRECs detected the expression of genes representative of different nephron segments (FIG. 12b). Immunostaining and flow cytometry confirmed the heterogeneous expression of segment specific proteins, suggesting that iRECs encompass cells with various tubular segment identities (FIG. 4g and FIG. 13c).

Figure 13E:
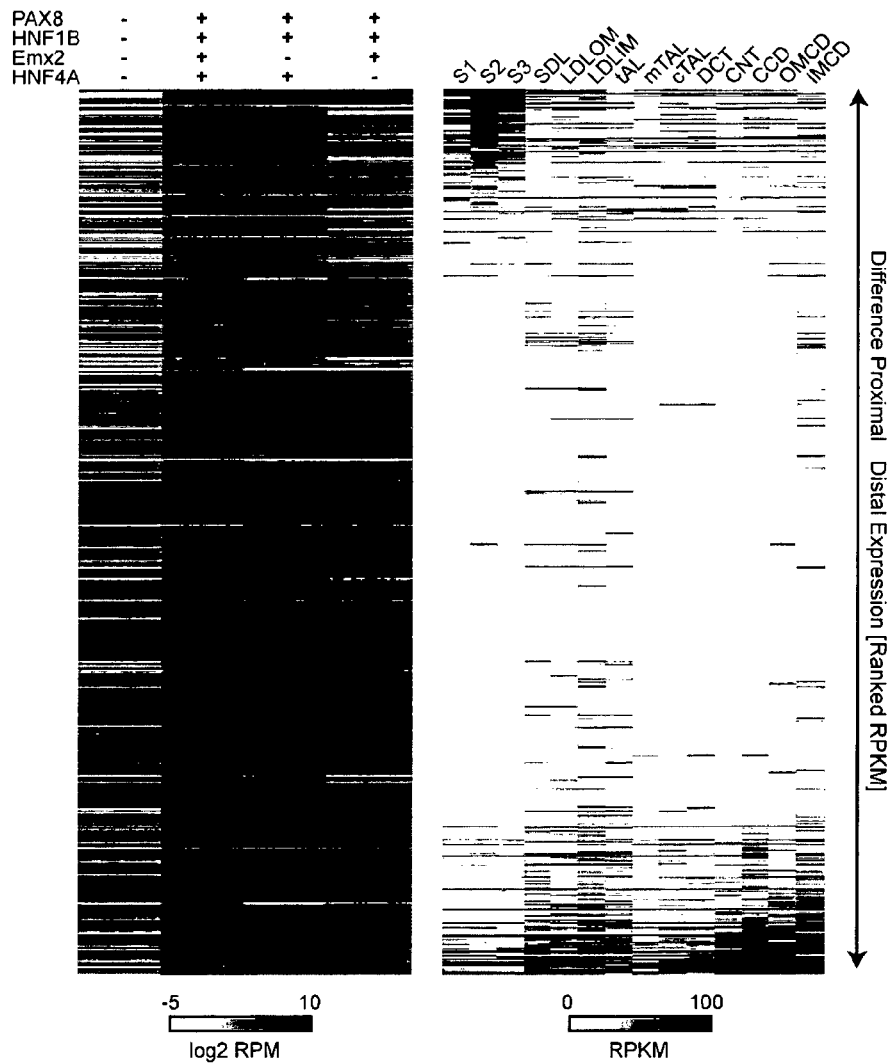

Two of the four reprogramming factors have distinct, non-overlapping segment-specific expression, namely Hnf4a in the proximal tubule and Emx2 in the collecting duct[39] (FIG. 13d). Interestingly, Pax8 and Hnf1b, two broadly expressed factors, were essential facilitators of iREC reprogramming (FIG. 2f), while omission of Emx2 or Hnf4a still enabled reporter activation at reduced frequencies. We speculated that the latter two factors may act instructively towards distinct tubule segment identities. Analysis of the global gene expression profile of cells transduced with only three instead of four factors confirmed that omission of Hnf4a, but not Emx2, decreased the expression of proximal tubule enriched genes (FIG. 4h and FIG. 13e). We conclude that tubule segment identity can be modulated by the precise composition of the reprogramming cocktail, and that Hnf4a contributes to the specification of a proximal tubule cell signature.

iRECs are Stably Reprogrammed and can be Expanded in Culture

Figure 13F:
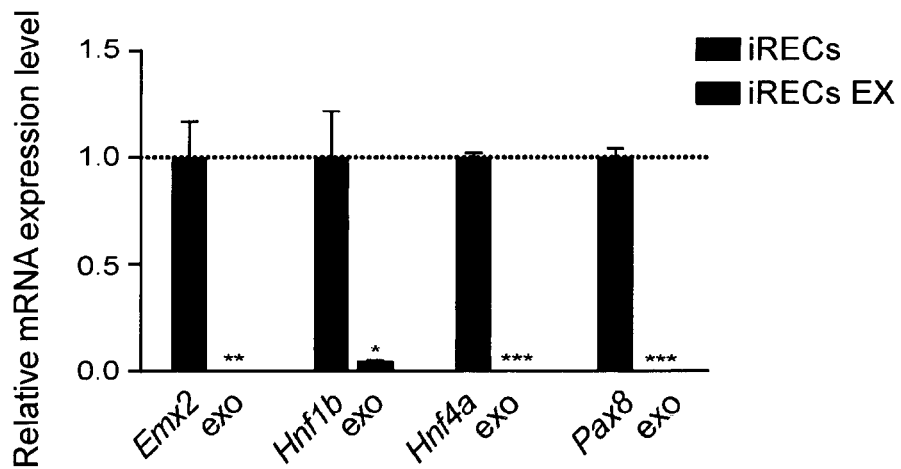
Figure 13G:
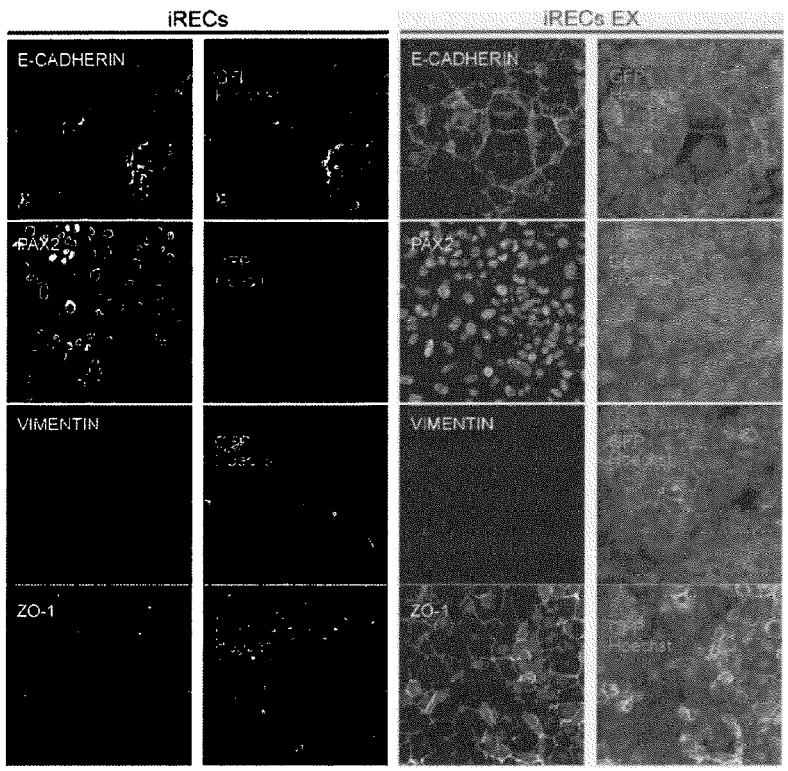
Figure 13G:
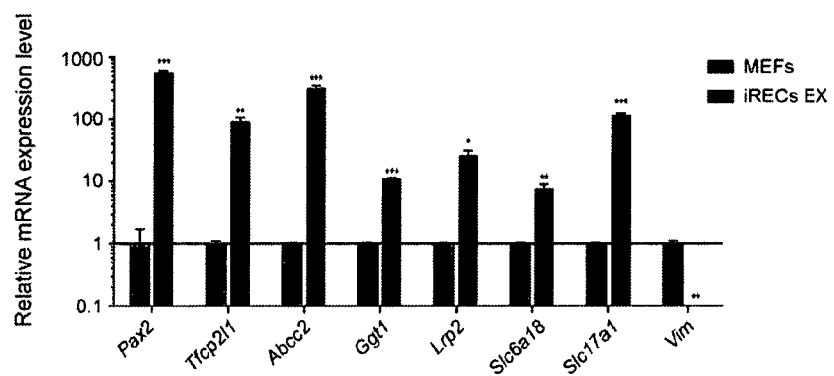
Figure 13G:
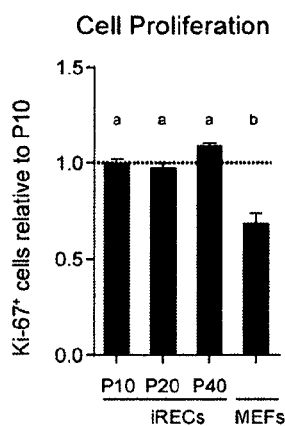
Figure 13G:
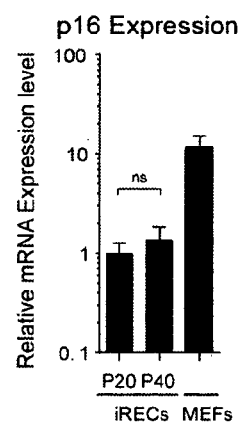
Figure 13K:
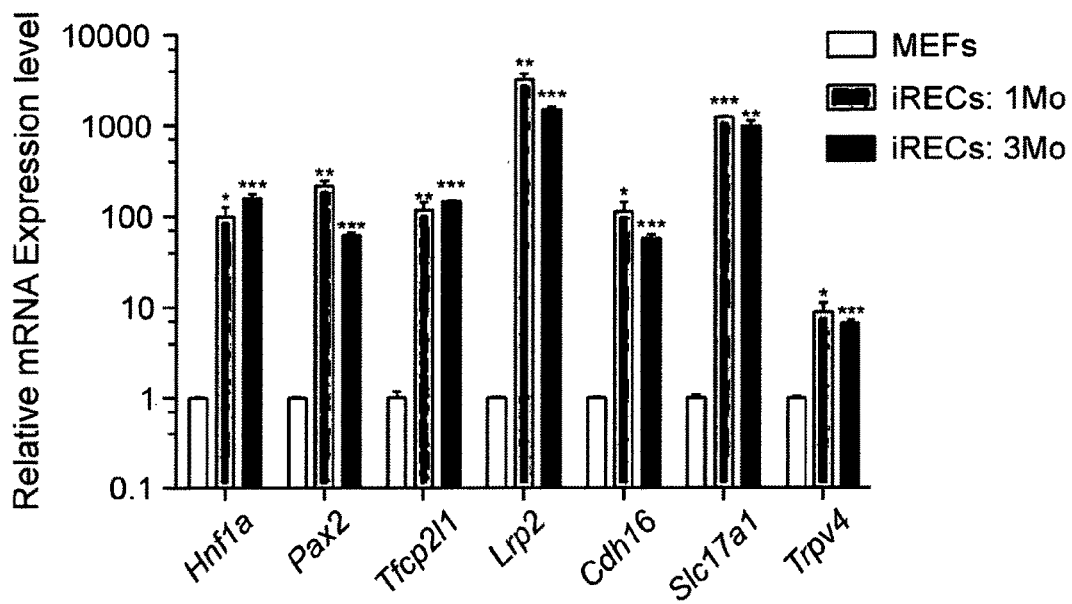

To determine if iREC cell identity is maintained after removal of the exogenous reprogramming factors, we introduced the four factors by a loxP-site containing provirus, which can be efficiently deleted upon expression of Ksp-Cre. These iRECs, retained their epithelial morphology, and expression of renal marker genes after 5 weeks of culture despite absence of exogenous expression of the four reprogramming factors (FIGS. 13f,g,h).

Next, we determined to what extent iRECs could be expanded in culture, an important feature for potential in vitro applications. iRECs could be propagated for at least 40 passages without signs of cellular senescence or dedifferentiation as monitored by Ki67, p16 and renal marker gene expression (FIGS. 13i,j,k). We conclude that iRECs are stably reprogrammed, do not depend on the continuous expression of exogenous transcription factors and can be expanded in-vitro.

iRECs Display Morphological and Functional Characteristics of Renal Tubular Epithelial Cells Next, we characterized the behavior of iRECs in a three dimensional extracellular matrix. iRECs consistently formed spheres with a central lumen when grown in Matrigel 3D culture (FIGS. 5a,b,c). In contrast, MEFs only formed irregular and unstructured conglomerates without obvious organization. iREC-derived spheres exhibited a robust apico-basal polarization with apical localization of tight junction protein ZO-1, apical actin accumulation indicated by phalloidin staining, and basolateral localization of β-catenin (FIG. 5d). Similarly, the localization of Na$^+$/K$^+$-ATPase alpha1 was detected basolaterally in iRECs, while megalin (LRP2) showed apical localization (FIG. 5d), consistent with their subcellular localization in renal tubular epithelial cells. The mechanosensory channel TRPV4 was detected predominantly at the apical membrane. Staining for the mesenchymal marker vimentin was completely absent from iREC spheres (FIG. 5d).

In addition, we performed ultrastructural analysis of 3D spheres by transmission electron microscopy. iRECs appeared as polarized cuboidal epithelial cells, established complex tight junctions and extended multiple luminal microvilli from their apical surface (FIG. 5e). Spheres were surrounded by a tight and electron-dense extracellular matrix, reminiscent of basement membrane material (FIG. 5e). The apolipoprotein-receptor megalin (LRP2) mediates the endocytotic uptake of proteins, including albumin[40]. Based on its prominent expression, we tested iRECs for the uptake of fluorescently labeled albumin. Fluorescence intensity was significantly increased in iRECs compared to MEFs (FIGS. 5f,g), indicating that iRECs possess endocytotic activity.

iRECs are Sensitive to Nephrotoxic Substances

Acute renal injury results from damage to renal tubular cells as a frequent adverse effect of nephrotoxic substances, such as Cisplatin, Gentamicin and Tacrolimus. For all three drugs, the rate of apoptosis was significantly higher in treated iRECs compared to MEFs (FIG. 5h and FIG. 14a). Kidney injury molecule 1 (KIM1) is a specific biomarker for tubular injury[41] and was markedly increased in iRECs following Gentamicin treatment (FIG. 5i and FIG. 14b). Cisplatin uptake into renal tubular cells is mediated in part by the organic cation transporter 2 (Oct2)[42]. Notably, cisplatin induced toxicity in iRECs could be decreased by incubation with 1 mM of Cimetidine, a known inhibitor of Oct2[43] (FIG. 5j). Thus, iRECs respond to nephrotoxic substances similar to tubular epithelial cells and may be employed for renal toxicity testing.

iRECs Integrate into Renal Organoids and Form Tubular Structures in Decellularized Kidneys Single cell suspensions of embryonic kidney cells can reaggregate and self-organize into renal organoids including embryonic renal structures such as ureteric bud and early tubules[44]. To test if iRECs share this potential, E13 embryonic kidneys constitutively expressing mTomato were disintegrated to single-cell suspension, and mixed with GFP-expressing iRECs or MEFs, followed by reaggregation and culture (FIG. 6a). While MEFs failed to integrate into tubular structures and were predominantly found in the stroma or were even excluded from the aggregates, iRECs integrated into tubule epithelial structures (FIG. 6b). Immunostaining for laminin demonstrated that iRECs shared a continuous basement membrane layer with neighboring epithelial cells (FIG. 6c). The proximal tubule marker LTL and megalin were similarly found in iRECs and in native tubule cells demonstrating that iRECs were differentiated and polarized within the renal microenvironment (FIGS. 6c,d,e). Thus, iRECs can participate in the formation of self-organizing kidney organoids.

Next, we asked if iRECs would also assemble into tubules in the absence of other cell types, only guided by the structure of extracellular matrix (ECM). Thus, we used decellularized kidney scaffolds with intact three-dimensional ECM as guidance structure for iRECs[45]. Here, iRECs grew into long, and partially convoluted tubules within the decellularized kidneys (FIG. 6f). Recellularization occurred in 77% of grafts, resulting in tubules that exhibited organized apico-basal polarization. Thus, iRECs have the potential to repopulate a kidney scaffold along preformed guidance structures.

Induction of Human Renal Epithelial Cells

Next, we tested if human fibroblasts could also be reprogrammed towards renal epithelial cell fate. Combined overexpression of EMX2, HNF1B, HNF4A, and PAX8 in human fibroblasts resulted in cells with epithelial morphology similar to murine iRECs (FIG. 7a). 4TF treated human cells showed marker expression comparable to iRECs, including membranous β-Catenin, nuclear PAX2, and positive staining for proximal tubule specific LTL (FIG. 7a). mRNA levels of renal transcription factors, adhesion molecules and transporters were upregulated after 4TF treatment as compared to fibroblasts (FIG. 7b).

To increase the proportion of reprogrammed human fibroblasts, we first enriched reprogrammed cells by sorting for epithelial cells. 4TF expression upregulated the epithelial cell adhesion molecule EPCAM (CD326), but reduced expression of the fibroblast marker THY-1 (CD90), in both mouse and human fibroblasts (FIG. 14c). We therefore isolated human iRECs (h-iRECs) by sorting for CD326$^+$ CD90$^-$ cells three weeks after lentiviral infection (FIG. 14d). Sorted h-iRECs formed 3D spheroids, (FIG. 7c) and were polarized, as indicated by apical actin accumulation and basolateral 3-Catenin expression (FIG. 7d).

We further aimed to optimize the efficiency of reprogramming in human cells. Similar to our previous observations in MEFs, expression of SV40 large T antigen increased the percentage of CD326$^+$CD90$^-$ cells to 6.5% four weeks after transduction (FIG. 14d).

To enhance sorting specificity, cells with renal marker expression were enriched. Therefore, we sorted for Prominin-1 (Prom-1, CD133), a glycoprotein specifically found in proximal tubule cells[46] (FIG. 7e). Employing an additional strategy, we introduced a GFP-reporter plasmid under the control of the human kidney specific CDH16 promoter (FIG. 7e and FIG. 14e), which successfully distinguished reprogrammed cells.

Differential expression profiling by RNA sequencing of cells sorted for CDH16 reporter activation revealed that h-iRECs clustered more closely to human tissue than to fibroblasts (FIG. 7f). Thus, the expression of EMX2, HNF1B, HNF4A, and PAX8 could similarly reprogram human fibroblasts into human renal epithelial like cells.

Use of iRECs for Disease Modeling:

To assess if reprogramming of fibroblasts to iRECs can be utilized in developing in vitro models for human disease, we followed two strategies. First, we used MEFs derived from a mouse model of autosomal dominant polycystic kidney disease (ADPKD) for reprogramming into iRECs. These mice carry a floxed Pkd1 allele (Pkd1$^{tm2Ggg}$), which can be excised upon expression of Cre-recombinase[59]. While the constitutive knockout of Pkd1 is embryonically lethal, conditional induction of Cre in these mice has been shown to replicate the cystic kidney disease phenotype observed in humans[60].

Pkd1$^{fl/fl}$ MEFs were reprogrammed by forced expression of 4TF. Of some of the resulting iRECs, single cells were isolated by cell sorting and clonally expanded. Clones that were confirmed to retain the expression of tubule specific marker genes by qPCR were used for further analysis. Lentiviral expression of Cre-recombinase led to an excision of the floxed allele, while expression of Flippase or no viral transduction served as negative controls (FIG. 16 a). Reprogrammed cells developed polarized epithelial spheroids in 3D-matrigel culture (FIG. 16 b). This demonstrates that reprogramming into iRECs can be used to develop in vitro disease models from genetically altered animal models.

In a second approach, we tested if direct disruption of genes associated with human kidney disease can be achieved in iRECs. Therefore, we CRISPR/Cas9-targeted Pkd2, which can also cause ADPKD when mutated in patients, in iRECs derived from wild-type MEFs. Expression of Cas9 and a guide RNA targeting the first exon of Pkd2 led to a disruption of the genomic locus, as detected by Sanger sequencing (FIG. 16 c). Thus, iRECs can be used to generate novel in vitro disease models by direct targeting as disease associated genes. This is not limited to cystic kidney disease, but can easily be applied to any condition that affects the renal tubules, including transport deficiencies (e.g. Bartter syndrome), metabolic syndromes that affect renal tubules (e.g. cystinosis), or ciliopathies (e.g. nephronophthisis), among others.

Methods

Animals

Xenopus embryos were cultured and manipulated as described previously[50]. In brief, female frogs were injected with 700 units of human chorionic gonadotropin (Sigma). On the next morning, oocytes were collected and in vitro fertilized. Embryos were cultured in 0.3× Mark's modified Ringer (1 M NaCl; 20 mM KCl; 10 mM MgCl$_2$; 20 mM CaCl$_2$; 50 mM HEPES pH 7.5). Staging was according to Nieuwkoop and Faber (http://xenbase.org). Gt(ROSA) 26Sor$^{tm4(ACTB-tdTomato,-EGFP)Luo/J}$ mice were purchased from The Jackson Laboratory (#007676 Strain of origin: B6.129 (Cg)) and bred with KSP-Cre/+(#012237 B6.Cg) mice to label renal tubular epithelial cells. Mice were housed in a SPF facility with free access to chow and water and a 12 h day/night cycle. Breeding and genotyping was done according to standard procedures. All animal experiments were conducted according to the National Institutes of Health *Guide for the Care and Use of Laboratory Animals*, as well as the German law for the welfare of animals and were approved by local authorities (Regierungspräsidium Freiburg X12/08J and X13/08J).

Cell Culture

Murine embryonic fibroblasts (MEFs) were obtained from limbs of E13 embryos to exclude contamination with renal tissue. Tail tip fibroblasts (TTFs) were obtained from postnatal P7 and adult (P60) mice. Tissue was minced with a scalpel and digested with 0.25% Trypsin-EDTA for 30 min at 37° C. Trypsinization was stopped by addition of MEF Medium (MEFM: Dulbecco's modified Eagle's medium (DMEM), 10% fetal bovine serum (FBS), 2 mM L-glutamine, penicillin/streptomycin). After resuspension the cells were centrifuged and the pellet was resuspended in MEFM and plated on gelatine-coated 6-well plates for 3 days until they reached confluency. Postnatal human fibroblasts used for qRT-PCR analysis were derived from foreskin (HFoFs) (Ethics committee number 521/13). Fetal human dermal fibroblasts (HFeFs) used for FACS, 2D and 3D immunostainings were obtained from ScienCell Research Laboratories (2300). Human cells were cultivated in DMEM, high glucose, supplemented with 10% fetal bovine serum, 2 mM L-glutamine and penicillin/streptomycin. MEFs, TTFs and human fibroblasts were frozen in liquid nitrogen and used without further passaging for reprogramming experiments. For efficiency improvement experiments the following substances were added to the cell culture medium for 7 days: Vitamin C (Sigma, 50 µg/ml); CHIR99021 (Sigma, 3 µM); Forskolin (FocusBiomolecules, 10 µM); Valproic Acid (Sigma, 1 mM); 5-Azacytidine (Sigma, 2 µM).

To generate CDH16 reporter cells, MEFs and HFeFs were infected with SV40 (Addgene:12246) and a lentivirus containing the human CDH16 promoter-GFP together with a puromycin resistance cassette (Genecopoeia, HPRM12721-LvPF02). Reporter cells were selected for puromycin resistance and absence of GFP expression (as determined by FACS) prior to 4TF treatment.

Albumin Uptake Assay

Cells were incubated with Alexa647 labeled albumin (1 mg/ml, Life technologies, A34785) at 37° C. for 0, 2, 5, 10, 15, 30 and 60 min. After incubation cells were washed five times with ice-cold PBS to stop endocytosis. Cells were fixed with 4% PFA and imaged using a Zeiss Axiovert fluorescence microscope equipped with a 40× lens. The average fluorescence intensity from 5 visual fields per time-point was calculated using ImageJ software.

Cytotoxicity Assay

MEFs and iRECs were incubated with drugs as follows: (Cisplatin (Teva): 6 µg/ml for 24 h; Tacrolimus (Invivogen): 40 µM for 24 h; Gentamicin (Sigma): 1 mg/ml for 48 h) Cells were harvested by collecting the supernatants as well as attached cells (obtained by trypsinization). Drug treated cells and untreated controls were stained with 1 µg/ml DAPI (Invitrogen, D1306) for 5 minutes and fluorescence was measured via flow cytometry using the 405 nm laser for excitation. Dead cells were identified by comparing emission of DAPI stained cell and unstained controls using a 450/50 nm band pass filter. For Kim-1 expression analysis MEFs and iRECs were treated with Gentamicin (1 mg/ml for 48 h), stained for Kim-1 (Miltenyi Biiotec, 130-106-024) and analyzed by flow cytometry. For cisplatin uptake inhibition experiments MEFs and iRECs were left untreated or incubated with either 6 µg/ml cisplatin alone or 6 µg/ml cisplatin and 1 mM cimetidine (Sigma-Aldrich, C4522). Cells were harvested and analyzed as described above. Experiments were performed in triplicates and repeated three times.

3D Cell Culture 3D cell culture was performed in Matrigel as described previously[51]. In brief, cells were trypsinized, passed through a 50 µm cell strainer and counted. 10,000 cells were resuspended in 100 µl growth factor reduced Matrigel (Corning, 354230) and seeded in 8-well µ-Slides (Ibidi, 80826). Matrigel was allowed to polymerize for 15 min at 37° C. followed by addition of renal epithelial growth medium (Lonza, CC-3190). Cells were imaged after 7 days or when spheroid formation was apparent. For immunofluorescent stainings cells were fixed in 4% PFA.

Quantitative Real-Time PCR

Total RNA was isolated using RNeasy Universal Plus Kit (Qiagen, 73404). 1 µg of RNA was reversely transcribed using QuantiTect Reverse Transcription Kit (Qiagen, 205311). qRT-PCR was performed using 1/500 to 1/50 of the reverse transcription reaction, gene specific primers and SYBR green Takyon mastermix (Eurogentec, UF-NSCT-B0210) or SYBR green I master (Roche, 04707516001) on a ROCHE LC480 light cycler. For each gene three biological replicates were analyzed. Every replicate was measured three times. For data analysis the 2(-Delta C(T)) method was used to calculate relative expression levels followed by statistical analysis using Student's t-test as described previously[52]. The sequences of primers used are included in Table 1.

TABLE 1

List of oligonucleotides used for quantitative RT-PCR analysis

| Primer name | Sequence | SEQ ID NO: |
| --- | --- | --- |
| Esrrg Forward | CTATGGGGTTGCATCATGTGAA | 5 |
| Esrrg Reverse | CGTCTGCGCTTTGTGATCTC | 6 |
| Hnf1a Forward | GACCTGACCGAGTTGCCTAAT | 7 |
| Hnf1a Reverse | CCGGCTCTTTCAGAATGGGT | 8 |
| Lhx1 Forward | CCCATCCTGGACCGTTTCC | 9 |
| Lhx1 Reverse | CGCTTGGAGAGATGCCCTG | 10 |
| Nr1h4 Forward | GCTTGATGTGCTACAAAAGCTG | 11 |
| Nr1h4 Reverse | CGTGGTGATGGTTGAATGTCC | 12 |
| Pax2 Forward | AAGCCCGGAGTGATTGGTG | 13 |
| Pax2 Reverse | CAGGCGAACATAGTCGGGTT | 14 |
| Tfcp2l1 Forward | GCTGGAGAATCGGAAGCTAGG | 15 |
| Tfcp2l1 Reverse | AAAACGACACGGATGATGCTC | 16 |
| Vdr Forward | GTGCAGCGTAAGCGAGAGAT | 17 |
| Vdr Reverse | GGATGGCGATAATGTGCTGTTG | 18 |
| Abcc2 Forward | GTGTGGATTCCCTTGGGCTTT | 19 |
| Abcc2 Reverse | CACAACGAACACCTGCTTGG | 20 |
| Ggt1 Forward | TTTGTCATCATCGGCCTCTGT | 21 |
| Ggt1 Reverse | CCCGTCCAATCTCTGAGCAG | 22 |
| Lrp2 Forward | ACACTTGTGGGCATTCTC | 23 |
| Lrp2 Reverse | GCAGTCATTATCACCATCAC | 24 |
| Slc6a18 Forward | TGCTTTGCCTGTTTCCTCTCA | 25 |
| Slc6a18 Reverse | ATGTCATCACAGAACCGTTTCAT | 26 |

TABLE 1-continued

List of oligonucleotides used for quantitative RT-PCR analysis

| Primer name | Sequence | SEQ ID NO: |
|---|---|---|
| Slc17a1 Forward | CCAAGGACCACCCGTATATGA | 27 |
| Slc17a1 Reverse | CTTTGATTGGCAGGGATTGTCT | 28 |
| Slc23a1 Forward | AAAGCAGCATGAGGTCGTGG | 29 |
| Slc23a1 Reverse | ACTGAAGCACGTCAGGTAATG | 30 |
| Trpv4 Forward | GCCGATTGAAGACTTTGAGG | 31 |
| Trpv4 Reverse | CTACGGCACTTACCGTCACC | 32 |
| Cdh1 Forward | AAGTACATCCTCTATTCTCA | 33 |
| Cdh1 Reverse | ATTCTGATCTGTCACTGT | 34 |
| Cdh6 Forward | GCAACGGAGATTAATAACC | 35 |
| Cdh6 Reverse | TCATAGAACTCAGCAAACT | 36 |
| Cdh16 Forward | ATACCAACTACAGGTCAC | 37 |
| Cdh16 Reverse | GTCATTCTCATCTTTCACAT | 38 |
| Actb Forward | CCTTCTTGGGTATGGAATC | 39 |
| Actb Reverse | CACTGTGTTGGCATAGAG | 40 |
| Tbp Forward | AGAACAATCCAGACTAGCAGCA | 41 |
| Tbp Reverse | GGGAACTTCACATCACAGCTC | 42 |
| HNF1A Forward | AACACCTCAACAAGGGCACTC | 43 |
| HNF1A Reverse | CCCCACTTGAAACGGTTCCT | 44 |
| NR1H4 Forward | GACTTTGGACCATGAAGACCAG | 45 |
| NR1H4 Reverse | GCCCAGACGGAAGTTTCTTATT | 46 |
| TFCP2L1 Forward | CGTTTAAGCAGAACGAGAATGGG | 47 |
| TFCP2L1 Reverse | TTTCATAGGACGGCTGGTATTTC | 48 |
| CDH16 Forward | AGAATGACAACGTGCCTATCTG | 49 |
| CDH16 Reverse | GCTGACAGTCTAGTCACTTCAGT | 50 |
| EPCAM Forward | ATAACCTGCTCTGAGCGAGTG | 51 |
| EPCAM Reverse | TGCAGTCCGCAAACTTTTACTA | 52 |
| GGT1 Forward | CTGGGGAGATCCGAGGCTAT | 53 |
| GGT1 Reverse | GATGACGGTCCGCTTGTTTTC | 54 |
| LRP2 Forward | GGCCTGCTATAACACCAGTCA | 55 |
| LRP2 Reverse | ACTCATTGTGCAAGCATATCTCA | 56 |
| SLC17A1 Forward | TCTGTTCCTTTCGCTATGGATTG | 57 |
| SLC17A1 Reverse | TTGGGCAAACCATGTGGATCT | 58 |
| HSPCB Forward | TCTGGGTATCGGAAAGCAAGCC | 59 |
| HSPCB Reverse | GTGCACTTCCTCAGGCATCTTG | 60 |
| p16 Forward | CGGTCGTACCCCGATTCAG | 61 |
| p16 Reverse | GCACCGTAGTTGAGCAGAAGAG | 62 |

Whole-Mount In Situ Hybridization

Whole-mount in situ hybridization of *Xenopus* embryos was performed at stages 22, 26, 33 and 38. Digoxigenin-UTP labeled antisense probes were used as described before[50]. To generate in situ probes, plasmids were linearized and transcribed with T7 or SP6 (Roche, DIG labeling kit). Antibody against digoxigenin conjugated to alkaline phosphatase was used to detect bound probes (Roche, 11093274910). In situ hybridization of paraffin-embedded mouse kidney sections was performed as described previously[53]. In brief, embryos, or dissected kidney anlagen were fixed in 4% paraformaldehyde (PFA)/phosphate buffered saline (PBS), dehydrated through ethanol series and embedded in paraffin for sectioning at 10 µm. Digoxigenin-UTP labeled antisense probes were used for in situ hybridization and Eosin counterstaining was performed according to standard protocols[53]. Plasmids used for probe synthesis are available upon request from the authors. Specific staining was detected on more than 5 embryos per stage. As WISH was part of the screen to identify reprogramming factors, this experiment was performed once.

Colony Formation Assay

Fifty cells from MEFs or iRECs were seeded in 6-well plates and allowed to grow for 14 days prior to fixation and staining with 0.1% crystal violet in a 10% ethanol solution for 15 min at room temperature. Colonies were counted by macroscopic visual inspection of cells from 3 independent experiments.

Microarray Analyses

Total RNA from CFP treated control MEFs, GFP sorted iRECs and GFP sorted primary renal KSP-Cre tubule cells extracted from P6 mTOM/mGFP transgenic mice was isolated using RNeasy Universal Plus Kit (Qiagen, 73404). All cells were subjected to sorting prior to RNA extraction. Total RNA samples were processed with the Affymetrix WT Plus kit (Ambion, Austin Tex., USA) as described by the manufacturer. Labeled fragments were hybridized to Affymetrix WT Mouse Gene ST 1.0/2.0 arrays for 16 h at 45° C. and 60 rpm in an Affymetrix hybridization oven 645. After washing and staining using the Hybridization, Wash and Stain Kit (Affymetrix, USA), the arrays were scanned with the Affymetrix GeneChip Scanner 3000 7G resulting in signal intensity values for each individual probe. CEL files were generated from the raw data with Affymetrix GeneChip Command Console Software Version 4.0. We used Partek Genomics Suite software for further analysis (Partek, Inc.). CEL files were imported including control and interrogating probes. Pre-background adjustment was set to adjust for GC Content and probe sequence and RMA background correction was performed. Arrays were normalized using Quantile normalization and probeset summarization was done using Median Polish. Probe values were log 2 transformed. In order to identify differentially expressed genes between the groups we performed a 1-way ANOVA in Partek. We used Fisher's Least Significant Difference (LSD) as Contrast method. The array results are deposited at ArrayExpress (E-MTAB-3648).

RNA Sequencing Analysis

2 µg of RNA was isolated from human fibroblasts, h-iRECs (4TF, SV40 treated, sorted for GFP high CDH16-reporter activity) without prior puromycin treatment or selection for low background or MEFs, MEFs treated with 4TF, 3TF(minus Pax8), or 3TF(minus Hhnfa) without prior sorting. Library preparation and sequencing (Illumina HiSeq single read) was performed by GATC Biotech AG (Konstanz, Germany). The human kidney sample was retrieved from EBI SRA (ERR030893). Sequence read alignment (TopHat) was done using the galaxy platform[54] and read counts were quantified using the SeqMonk software (http://www.bioinformatics.babraham.ac.uk/projects/seqmonk/). Significantly differential expression was calculated by ANOVA between groups before hierarchical clustering. For analysis of 4-1 treated cells, genes significantly upregulated (p<0.0001, ANOVA) and with one $\log_2$ difference in expression between MEFs and 4TF treated cells were considered. Genes were mapped to RPKM expression data of rat tubule segments[39] and sorted according to the difference between median expression in proximal segments (S1-3) and collecting ducts (CNT, CCD, OMCD, and IMCD). All relevant RNA-Seq data are available from the authors and will be deposited to the European Nucleotide Archive.

Molecular Cloning and Lentiviral Transduction

Full-length or fragments of *Xenopus* and mouse transcription factors were cloned from cDNA of reverse transcribed total RNA isolates from stage 39 *Xenopus* and E15 mouse embryonic kidneys. Gene specific primers were used to amplify the coding sequences of the transcription factors. PCR products were cloned into pWPXLd, (Addgene (#12258)). To produce lentiviruses, plasmid DNA of pWPXLd, pMD2.G (Addgene #12559), and psPax2 (Addgene #12260) were co-transfected into 293T cells using Calcium Phosphate. Two days after transfection cell supernatants were harvested and virus was concentrated using polyethylene glycol precipitation as described previously[55]. Concentrated virus was frozen at −80° C. and thawed directly before transduction of cells. For the infection of MEFs, TTFs, HFoFs and HFeFs virus concentrate was diluted 1:100 (high viral titers) to 1:1000 (low viral titers) in MEFM containing 10 µg/ml Polybrene and cells were incubated for 12 h. Viral infection was repeated five to seven times. After cultivation in MEFM for 7 days, MEFs and TTFs were analyzed for GFP expression by flow cytometry. GFP positive iRECs were isolated by fluorescence activated cell sorting (FACS) 14 days after the last virus transduction and expanded for further analysis. Reprogrammed HFeFs were identified 21-28 days after the last transduction by sorting for $CD326^+CD90^-$, $CD326^+CD133^+$ or CDH16-$GFP^+$ cells.

Western Blot Analysis

Proteins were fractionated by SDS/PAGE and anti 2A-peptide antibody (ABS31, Merck Millipore) was used for protein detection by Western blot.

Immunofluorescent Stainings

Cells were washed twice with PBS and fixed in 4% paraformaldehyde for 15 min at room temperature. For permeabilization the cells were incubated with PBST (0.1% Triton-X-100 in PBS) for 10 min at room temperature. After blocking for 1 h with 2% horse serum, 5% BSA, 1% goldfish gelatin in PBS cells were incubated with primary antibody for 60 min at room temperature and subsequently with a secondary fluorescence-conjugated antibody for 60 min at room temperature in the dark. DNA was stained with Hoechst 33342 diluted 1:2,000 in PBS. Primary and secondary antibodies were diluted in PBS containing 10% of the blocking solution. Antibodies used for immunofluorescent staining were as follows: β-Catenin (Santa-Cruz, sc7199, 1:100), E-Cadherin (Invitrogen, 13-1900, 1:100), Epcam (Abcam, ab71916, 1:100), Laminin (Sigma, L9393, 1:100), tetragonolobus lectin (LTL) (Biozol, B-1325, 1:100), Megalin (Santa-Cruz, sc16478, 1:100), $Na^+K^+$-ATPase (Abcam, ab7671, 1:100), PAX2 (Abcam, ab37129, 1:100), Phalloidin (Mol. Probes, A22287, 1:100), TRPV4 (Alomone, acc-034, 1:100), Vimentin (Sigma, V2258, 1:100), ZO-1 (Santa-Cruz, sc33725, 1:100), PDZK1 (Sigma Aldrich/Atlas Antibodies, HPA006155m, 1:100), Bst1 (BioLegend, BP-3, 1:100), FETUB (GeneTex, GTX112260, 1:100).

The following secondary antibodies were used: Goat anti rat Alexa-633 (Life Technologies, A-21094, 1:500), Goat anti rabbit Alexa-647 (Life Technologies, A-21245, 1:500), Goat anti mouse Alexa-647 (Life Technologies, A-21235, 1:500), Donkey anti goat Alexa-647 (Life Technologies, A-21447, 1:500). Biotinylated tetragonolobus lectin (LTL) (Biozol, B-1325, 1:100) was labeled with streptavidin Alexa 657 (Invitrogen, S-32357, 1:500). Experiments were successfully repeated three times.

Flow Cytometry

For flow cytometry analyses, cells were harvested, resuspended in FACS buffer (PBS supplemented with 3% FBS and 5 mM EDTA), filtered through a 50 μm cell strainer and analyzed using the 13-color LCR Fortessa FACS analyzer (Becton Dickinson). For the selection of GFP positive cells the ARIA III or ARIAFusion cell sorters (Becton Dickinson) were used. Data were analyzed by FlowJo (FlowJo LLC) or FACS DIVA (Becton Dickinson) software. For sorting or analysis of mouse and human cells the following antibodies were used according to the manufacturer's instructions: anti-mouse CD90 Alexa 647 (Biolegend, 105317), anti-mouse CD326 BV421 (BD Bioscience, 563214), anti-mouse CD324 Alexa 647 (Biolegend, 147308), anti-mouse CD157 APC (Biolegend, 140207), anti-mouse Ki-67 APC (Biolegend, 652406), anti-human CD90 FITC (MACS Miltenyi Biotec, 130-097-930), anti-human CD326 BV421 (BD Bioscience, 563180), anti-human CD133 PE (Miltenyi Biotec, 130-098-046). Prior to staining for E-Cadherin cells were grown on Nunc Up Cell Surface cell culture plates (Sigma, Z688800-6CS) and harvested without trypsin digestion. Experiments were successfully repeated at least three times.

Kidney Reaggregation

Kidney reaggregation was performed as described previously[56]. In brief, 20 E13 embryonic mouse kidneys were harvested and digested. 80,000 embryonic kidney cells were mixed with 8,000 iRECs or control cells and pelleted by centrifugation. The pellet was transferred to a low-binding PCR tube and allowed to aggregate overnight at 37° C. Next day the cell aggregates were transferred to a transwell filter (Costar, 3450) and cultured for 4 days at 37° C., 5% $CO_2$. Reaggregates were fixed in 4% PFA, stained and imaged by confocal microscopy.

Recellularization of Decellularized Kidneys

For recellularization experiments[45] cadaveric kidneys from adult wild-type rats or mice were flushed 10 times with heparinized PBS (10 U/ml; Sigma H3393) followed by incubation in 1% SDS (Roth 2326.3) in PBS for three to five days until decellularization was observed. During this time kidneys were repeatedly washed with 1% SDS in PBS every 6 to 12 h. Subsequently, decellularized kidneys were rinsed 5 times with PBS containing penicillin/streptomycin and 100 μg/ml Normocin (Invivogen). Seeding of iRECs into the organ scaffolds was performed by injection of $10^6$ trypsinized cells with a 25G needle and subsequent cultivation in MEFM for 14 days. Extracellular matrix was visualized by excitation of autofluorescence with a two-photon laser at 740 nm with high detector sensitivity.

Imaging

Confocal imaging was performed using a LSM-I-NLO2 510 META microscope equipped with a 25x/0.8 LD LCI-Plan-Apochromat objective (both Carl Zeiss). Excitation of the fluorophores (Hoechst 33342, GFP, Tomato, Alexa647) was performed with a two photon laser at 740 nm, and a single photon laser at 488 nm, 561 nm and 633 nm, respectively. Image analysis was performed using ZEN (Zeiss) and Imaris (Bitplane) software.

Transmission Electron Microscopy 3D cultures of MEFs and iRECs were fixed in 4% PFA and 1% glutaraldehyde in 0.1 M phosphate buffer for 1 h at room temperature. After washing in 0.1 M PB cultures were contrasted using 1% $OsO_4$ (Sigma-Aldrich, Germany) for 45 minutes and 1% uranyl acetate (Polysciences, Germany) in 70% ethanol. After dehydration cultures were flat embedded in Durcupan (Sigma-Aldrich, Germany). Ultrathin sections (40 nm thickness) were analyzed using a Philipps CM 100 transmission electron microscope.

Data Analysis

Quantitative expression data[23] for all transcription factors across various human tissues was analyzed to identify candidate reprogramming factors. Relative expression was determined as the absolute expression in the target tissue divided by the median of all other tissues. Transcriptional circuitry analysis was performed as previously described[37] and the online platform http://www.regulatorynetworks.org/ was used to retrieve predicted transcriptional targets of reprogramming factors. Differential expression values between MEFs and iRECs of the microarray experiments were mapped to each target and visualized using Cytoscape[57]. CellNet scores were calculated using the online platform http://cellnet.hms.harvard.edu/[34]. For comparison of differentially regulated genes to published RNAseq data, the raw data[35, 36] was mapped to 10 fold differentially regulated genes between iREC and MEFs based on microarray analysis. For GO-term analysis of molecular function, 10 fold differentially regulated genes were analyzed using the DAVID-platform[58]. Statistical analysis was performed using SigmaStat and graphs were made with GraphPadPrism. Data were normally distributed when using Student's t-test. Differences in variance were determined when multiple groups were compared by ANOVA. Data analysis was performed with Microsoft Excel.

No statistical method was used to predetermine sample size. No samples were excluded from analysis. No method of randomization was used to determine how samples were allocated. The experiments were not randomized. Investigators were not blinded during the experiment or analysis.

Use of iRECs for Disease Modeling:

$Pkd1^{fl/fl}$ MEFs were isolated from E13.5 embryos ($Pkd1^{tm2Ggg}$) and reprogramming was performed as described above. Cre recombinase, and Flippase were subcloned into pWPXLd and lenti-virally transduced. Clonal selection into 96-well plates was performed using an Aria Fusion Cell Sorter. For CRISPR/Cas9 targeting of Pkd2, the primers 5'-cac cgt gcc tgg agc agg acg aaa g-3' (SEQ ID NO:63) and 5'-cac cgt gcc tgg agc agg acg aaa g-3' (SEQ ID NO:64) were used to generate a lentiGuide-Puro construct targeting the first Exon of Pkd2. was used. Together with lentiCas9-Blast these constructs were lenti-virally expressed in iRECs. The genomic locus was amplified using the primers: 5'-gccatggttaactccagacg-3' (SEQ ID NO:65) and 5'-gcgcaggcagttgtcaag-3' (SEQ ID NO:66). The PCR product was Sanger-sequenced to detect irregular ans scrambled chromatograms after the target side, indicating successful indel formation.

REFERENCES

1. USRD United States Renal Data System. Annual Data Report: Epidemiology of Kidney Disease in the United States. National Institutes of Health, National Institute of Diabetes and Digestive and Kidney Diseases, Bethesda, Md. (2014).
2. Morizane, R. et al. Nephron organoids derived from human pluripotent stem cells model kidney development and injury. *Nat Biotechnol* 33, 1193-1200 (2015).
3. Taguchi, A. et al. Redefining the in vivo origin of metanephric nephron progenitors enables generation of complex kidney structures from pluripotent stem cells. *Cell Stem Cell* 14, 53-67 (2014).
4. Takasato, M. et al. Directing human embryonic stem cell differentiation towards a renal lineage generates a self-organizing kidney. *Nat Cell Biol* 16, 118-126 (2014).
5. Takasato, M. et al. Kidney organoids from human iPS cells contain multiple lineages and model human nephrogenesis. *Nature* 526, 564-568 (2015).
6. Xia, Y. et al. Directed differentiation of human pluripotent cells to ureteric bud kidney progenitor-like cells. *Nat Cell Biol* 15, 1507-1515 (2013).
7. Papadimou, E. et al. Direct Reprogramming of Human Bone Marrow Stromal Cells into Functional Renal Cells Using Cell-free Extracts. *Stem Cell Reports* (2015).
8. Knoepfler, P. S. Deconstructing stem cell tumorigenicity: a roadmap to safe regenerative medicine. *Stem cells* 27, 1050-1056 (2009).
9. Xu, J., Du, Y. & Deng, H. Direct lineage reprogramming: strategies, mechanisms, and applications. *Cell Stem Cell* 16, 119-134 (2015).
10. Vierbuchen, T. et al. Direct conversion of fibroblasts to functional neurons by defined factors. *Nature* 463, 1035-1041 (2010).
11. Najm, F. J. et al. Transcription factor-mediated reprogramming of fibroblasts to expandable, myelinogenic oligodendrocyte progenitor cells. *Nat Biotechnol* 31, 426-433 (2013).
12. Yang, N. et al. Generation of oligodendroglial cells by direct lineage conversion. *Nat Biotechnol* 31, 434-439 (2013).
13. Ieda, M. et al. Direct reprogramming of fibroblasts into functional cardiomyocytes by defined factors. *Cell* 142, 375-386 (2010).
14. Du, Y. et al. Human hepatocytes with drug metabolic function induced from fibroblasts by lineage reprogramming. *Cell Stem Cell* 14, 394-403 (2014).
15. Huang, P. et al. Induction of functional hepatocyte-like cells from mouse fibroblasts by defined factors. *Nature* 475, 386-389 (2011).
16. Sekiya, S. & Suzuki, A. Direct conversion of mouse fibroblasts to hepatocyte-like cells by defined factors. *Nature* 475, 390-393 (2011).
17. Buganim, Y. et al. Direct reprogramming of fibroblasts into embryonic Sertoli-like cells by defined factors. *Cell Stem Cell* 11, 373-386 (2012).
18. Hendry, C. E. et al. Direct transcriptional reprogramming of adult cells to embryonic nephron progenitors. *Journal of the American Society of Nephrology: JASN* 24, 1424-1434 (2013).
19. Heinaniemi, M. et al. Gene-pair expression signatures reveal lineage control. *Nat Methods* 10, 577-583 (2013).
20. Pereira, C. F., Lemischka, I. R. & Moore, K. Reprogramming cell fates: insights from combinatorial approaches. *Ann N Y Acad Sci* 1266, 7-17 (2012).
21. Rackham, O. J. et al. A predictive computational framework for direct reprogramming between human cell types. *Nature genetics* 48, 331-335 (2016).
22. Lang, A. H., Li, H., Collins, J. J. & Mehta, P. Epigenetic landscapes explain partially reprogrammed cells and identify key reprogramming genes. *PLoS Comput Biol* 10, e1003734 (2014).
23. Ravasi, T. et al. An atlas of combinatorial transcriptional regulation in mouse and man. *Cell* 140, 744-752 (2010).
24. Raciti, D. et al. Organization of the pronephric kidney revealed by large-scale gene expression mapping. *Genome Biol* 9, R84 (2008).
25. Harding, S. D. et al. The GUDMAP database—an online resource for genitourinary research. *Development* 138, 2845-2853 (2011).
26. McMahon, A. P. et al. GUDMAP: the genitourinary developmental molecular anatomy project. *Journal of the American Society of Nephrology: JASN* 19, 667-671 (2008).
27. Yu, J. et al. Identification of molecular compartments and genetic circuitry in the developing mammalian kidney. *Development* 139, 1863-1873 (2012).
28. Shao, X., Somlo, S. & Igarashi, P. Epithelial-specific Cre/lox recombination in the developing kidney and genitourinary tract. *Journal of the American Society of Nephrology: JASN* 13, 1837-1846 (2002).
29. Liu, M. L. et al. Small molecules enable neurogenin 2 to efficiently convert human fibroblasts into cholinergic neurons. *Nature communications* 4, 2183 (2013).
30. Bar-Nur, O. et al. Small molecules facilitate rapid and synchronous iPSC generation. *Nat Meth* 11, 1170-1176 (2014).
31. Huangfu, D. et al. Induction of pluripotent stem cells by defined factors is greatly improved by small-molecule compounds. *Nat Biotech* 26, 795-797 (2008).
32. Huang, P. et al. Direct Reprogramming of Human Fibroblasts to Functional and Expandable Hepatocytes. *Cell Stem Cell* 14, 370-384.
33. Valentich, J. D., Tchao, R. & Leighton, J. Hemicyst formation stimulated by cyclic AMP in dog kidney cell line MDCK. *J Cell Physiol* 100, 291-304 (1979).
34. Cahan, P. et al. CellNet: network biology applied to stem cell engineering. *Cell* 158, 903-915 (2014).
35. Cabili, M. N. et al. Integrative annotation of human large intergenic noncoding RNAs reveals global properties and specific subclasses. *Genes Dev* 25, 1915-1927 (2011).
36. Shen, Y. et al. A map of the cis-regulatory sequences in the mouse genome. *Nature* 488, 116-120 (2012).
37. Neph, S. et al. Circuitry and dynamics of human transcription factor regulatory networks. *Cell* 150, 1274-1286 (2012).
38. Jaitovich, A. & Bertorello, A. M. Salt, Na+,K+-ATPase and hypertension. *Life Sci* 86, 73-78 (2010).
39. Lee, J. W., Chou, C. L. & Knepper, M. A. Deep Sequencing in Microdissected Renal Tubules Identifies Nephron Segment-Specific Transcriptomes. *Journal of the American Society of Nephrology: JASN* 26, 2669-2677 (2015).
40. Cui, S., Verroust, P. J., Moestrup, S. K. & Christensen, E. I. Megalin/gp330 mediates uptake of albumin in renal proximal tubule. *Am J Physiol* 271, F900-907 (1996).
41. Vaidya, V. S. et al. Kidney injury molecule-1 outperforms traditional biomarkers of kidney injury in preclinical biomarker qualification studies. *Nat Biotech* 28, 478-485 (2010).
42. Ciarimboli, G. et al. Cisplatin nephrotoxicity is critically mediated via the human organic cation transporter 2. *The American journal of pathology* 167, 1477-1484 (2005).

43. Yonezawa, A. et al. Association between tubular toxicity of cisplatin and expression of organic cation transporter rOCT2 (Slc22a2) in the rat. *Biochemical pharmacology* 70, 1823-1831 (2005).
44. Unbekandt, M. & Davies, J. A. Dissociation of embryonic kidneys followed by reaggregation allows the formation of renal tissues. *Kidney Int* 77, 407-416 (2010).
45. Song, J. J. et al. Regeneration and experimental orthotopic transplantation of a bioengineered kidney. *Nat Med* 19, 646-651 (2013).
46. Legouis, D. et al. Ex vivo analysis of renal proximal tubular cells. *BMC cell biology* 16, 12 (2015).
47. Nam, Y. J. et al. Induction of diverse cardiac cell types by reprogramming fibroblasts with cardiac transcription factors. *Development* 141, 4267-4278 (2014).
48. Wernig, M. et al. A drug-inducible transgenic system for direct reprogramming of multiple somatic cell types. *Nat Biotechnol* 26, 916-924 (2008).
49. Yoo, A. S. et al. MicroRNA-mediated conversion of human fibroblasts to neurons. *Nature* 476, 228-231 (2011).
50. Lienkamp, S. et al. Inversin relays Frizzled-8 signals to promote proximal pronephros development. *Proc Natl Acad Sci USA* 107, 20388-20393 (2010).
51. Giles, R. H., Ajzenberg, H. & Jackson, P. K. 3D spheroid model of mlMCD3 cells for studying ciliopathies and renal epithelial disorders. *Nat Protoc* 9, 2725-2731 (2014).
52. Schmittgen, T. D. & Livak, K. J. Analyzing real-time PCR data by the comparative C(T) method. *Nat Protoc* 3, 1101-1108 (2008).
53. Nagy, A. G., M.; Vintersten, K.; Behringer, R. [Production of chimeras]. Manipulating the mouse embryo. A laboratory manual. 3rd edition., in Cold Spring Harbor Laboratory Press 453-506 (2003).
54. Afgan, E. et al. The Galaxy platform for accessible, reproducible and collaborative biomedical analyses: 2016 update. *Nucleic acids research* (2016).
55. Kutner, R. H., Zhang, X. Y. & Reiser, J. Production, concentration and titration of pseudotyped HIV-1-based lentiviral vectors. *Nat Protoc* 4, 495-505 (2009).
56. Xia, Y. et al. The generation of kidney organoids by differentiation of human pluripotent cells to ureteric bud progenitor-like cells. *Nat Protoc* 9, 2693-2704 (2014).
57. Shannon, P. et al. Cytoscape: a software environment for integrated models of biomolecular interaction networks. *Genome Res* 13, 2498-2504 (2003).
58. Huang da, W., Sherman, B. T. & Lempicki, R. A. Systematic and integrative analysis of large gene lists using DAVID bioinformatics resources. *Nat Protoc* 4, 44-57 (2009).
59. Piontek, K. B. et al. A functional floxed allele of Pkd1 that can be conditionally inactivated in vivo. *J Am Soc Nephrol* 15, 3035-43 (2004).
60. Raphael, K. L. et al. Inactivation of Pkd1 in principal cells causes a more severe cystic kidney disease than in intercalated cells. Kidney Int 75, 626-33 (2009).

The invention claimed is:

1. A method of inducing the conversion of differentiated cells into induced renal tubular epithelial cells (iRECs), said method comprising the step of engineering said differentiated cells to overexpress Hnf1b and Pax8 by introducing into said differentiated cells one or more nucleic acids encoding the genes Hnf1b and Pax8 and overexpressing said genes so as to induce conversion of said differentiated cells into said iRECs, wherein said iRECs exhibit an mRNA-expression profile analogous to primary tubular cells, show morphological and functional features of kidney tubule epithelia, and are capable of integrating into kidney organoids and forming tubular structures in a decellularized kidney scaffold.

2. The method of claim 1, wherein said differentiated cells are further engineered to overexpress Emx2 or Hnf4a.

3. The method of claim 1, wherein said differentiated cells are further engineered to overexpress Emx2.

4. The method of claim 1, wherein said differentiated cells are further engineered to overexpress Hnf4.

5. The method of claim 1, wherein said differentiated cells are further engineered to overexpress Emx2 and Hnf4.

6. The method of claim 1, wherein said differentiated cells are fibroblasts.

7. The method of claim 6, wherein said fibroblasts are embryonic fibroblasts.

8. The method of claim 6, wherein said fibroblasts are adult fibroblasts.

9. The method of claim 1, wherein said differentiated cells are obtained from a non-human animal having a modification of a gene associated with a disorder affecting the kidney.

10. The method of claim 9, wherein said disorder affecting the kidney is selected from the group consisting of conditions affecting the renal tubules, transport deficiencies, metabolic syndromes affecting renal tubules, ciliopathies, end stage renal disease, cystic kidney disease, polycystic kidney disease, CAKUT, renal cystic diseases, interstitial diseases, tumorous kidney diseases, renal tubular diseases, metabolic diseases, and nephrolithiasis.

11. The method of claim 9, wherein said gene associated with a disorder affecting the kidney is Pkd1 or Pkd2.

12. The method of claim 6, wherein said one or more nucleic acids are plasmids or vectors comprising a nucleotide sequence encoding the genes, operably linked to a promoter capable of inducing overexpression of the encoded genes.

13. The method of claim 2, wherein said Emx2 comprises the nucleotide sequence as shown in SEQ ID NO:1 or a functional fragment thereof.

14. The method of claim 1, wherein said Hnf1b comprises the nucleotide sequence as shown in SEQ ID NO:2 or a functional fragment thereof.

15. The method of claim 2, wherein said Hnf4a comprises the nucleotide sequence as shown in SEQ ID NO:3 or a functional fragment thereof.

16. The method of claim 1, wherein said Pax8 comprises the nucleotide sequence as shown in SEQ ID NO:4 or a functional fragment thereof.

17. The method of claim 1, wherein said method further comprises the step of modifying in said differentiated cells at least one gene associated with a disorder affecting the kidney.

18. The method of claim 17, wherein said step of modifying comprises disrupting said gene associated with a disorder affecting the kidney.

19. The method of claim 17, wherein said disorder affecting the kidney is selected from the group consisting of conditions affecting the renal tubules, transport deficiencies, metabolic syndromes affecting renal tubules, ciliopathies, end stage renal disease, cystic kidney disease, polycystic kidney disease, CAKUT, Renal cystic diseases, interstitial diseases, tumorous kidney diseases, renal tubular diseases, metabolic diseases, and nephrolithiasis.

20. The method of claim 17, wherein said gene associated with a disorder affecting the kidney is Pkd1 or Pkd2.

21. An induced renal tubular epithelial cell (iREC) obtained by the method of claim 1.

22. The renal tubular epithelial cell of claim 21, wherein said iREC has a modification in at least one gene associated with a disorder affecting the kidney.

23. The renal tubular epithelial cell of claim 22, wherein said modification is a constitutive or conditional knockout of said gene.

24. The renal tubular epithelial of claim 22, wherein said disorder affecting the kidney is selected from the group consisting of conditions affecting the renal tubules, transport deficiencies, metabolic syndromes affecting renal tubules, ciliopathies, end stage renal disease, cystic kidney disease, polycystic kidney disease, CAKUT, renal cystic diseases, interstitial diseases, tumorous kidney diseases, renal tubular diseases, metabolic diseases, and nephrolithiasis.

25. The renal tubular epithelial cell of claim 22, wherein said gene associated with a disorder affecting the kidney is Pkd1 or Pkd2.

* * * * *

UNITED STATES PATENT AND TRADEMARK OFFICE
CERTIFICATE OF CORRECTION

| | |
|---|---|
| PATENT NO. | : 11,046,932 B2 |
| APPLICATION NO. | : 16/072459 |
| DATED | : June 29, 2021 |
| INVENTOR(S) | : Soeren Lienkamp et al. |

Page 1 of 1

It is certified that error appears in the above-identified patent and that said Letters Patent is hereby corrected as shown below:

In the Claims

In Line 2 of Claim 4 (at Column 65, Line 37), replace the term "Hnf4" with the term -- Hnf4a --.

In Line 2 of Claim 5 (at Column 65, Line 39), replace the term "Hnf4" with the term -- Hnf4a --.

In Line 1 of Claim 12 (at Column 65, Line 59), replace the phrase "of claim 6" with the phrase -- of claim 1 --.

In Line 1 of Claim 24 (at Column 66, Line 55), insert the word -- cell -- after the phrase "renal tubular epithelial".

Signed and Sealed this
Seventh Day of December, 2021

Drew Hirshfeld
*Performing the Functions and Duties of the
Under Secretary of Commerce for Intellectual Property and
Director of the United States Patent and Trademark Office*